US009907844B2

(12) United States Patent
Cui et al.

(10) Patent No.: US 9,907,844 B2
(45) Date of Patent: Mar. 6, 2018

(54) HUMAN HERPESVIRUS TRIMERIC GLYCOPROTEIN B, PROTEIN COMPLEXES COMPRISING TRIMERIC GB AND THEIR USE AS VACCINES

(71) Applicant: The Henry M. Jackson Foundation for the Advancement of Military Medicine, Inc., Bethesda, MD (US)

(72) Inventors: Xinle Cui, Gaithersburg, MD (US); Clifford M. Snapper, Potomac, MD (US); James J. Mond, Silver Spring, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 15/103,427

(22) PCT Filed: Dec. 11, 2014

(86) PCT No.: PCT/US2014/069856
§ 371 (c)(1),
(2) Date: Jun. 10, 2016

(87) PCT Pub. No.: WO2015/089340
PCT Pub. Date: Jun. 18, 2015

(65) Prior Publication Data
US 2016/0303225 A1   Oct. 20, 2016

Related U.S. Application Data

(60) Provisional application No. 61/914,903, filed on Dec. 11, 2013.

(51) Int. Cl.
| | |
|---|---|
| A61K 39/245 | (2006.01) |
| C12N 7/00 | (2006.01) |
| C07K 7/08 | (2006.01) |
| C07K 14/005 | (2006.01) |
| A61K 39/12 | (2006.01) |
| A61K 39/00 | (2006.01) |

(52) U.S. Cl.
CPC ............ *A61K 39/245* (2013.01); *A61K 39/12* (2013.01); *C07K 7/08* (2013.01); *C07K 14/005* (2013.01); *C12N 7/00* (2013.01); *A61K 39/00* (2013.01); *A61K 2039/575* (2013.01); *A61K 2039/70* (2013.01); *C07K 2319/02* (2013.01); *C07K 2319/21* (2013.01); *C12N 2710/16122* (2013.01); *C12N 2710/16134* (2013.01); *C12N 2710/16222* (2013.01); *C12N 2710/16234* (2013.01)

(58) Field of Classification Search
CPC ............ C12N 7/00; C12N 2760/16134; C12N 2710/16634; C12N 15/869; C12N 2710/16034; C12N 2710/16134; C12N 2710/16671; C12N 2700/00; C07K 14/005; C07K 14/035; C07K 14/045; C07K 16/088; A61K 39/245; A61K 39/12; A61K 35/763; A61K 38/162; A61K 49/14

See application file for complete search history.

(56) References Cited

U.S. PATENT DOCUMENTS

| | | | |
|---|---|---|---|
| 6,448,389 B1 | 9/2002 | Gonczol et al. | |
| 2008/0107620 A1 | 5/2008 | Khanna | |
| 2008/0199493 A1 | 8/2008 | Picker et al. | |
| 2010/0261155 A1 | 10/2010 | Peeples et al. | |
| 2013/0005648 A1 | 1/2013 | Melnki et al. | |
| 2017/0014497 A1* | 1/2017 | Tang ................. | A61K 39/0011 |

FOREIGN PATENT DOCUMENTS

| | | |
|---|---|---|
| WO | 2006/056027 A1 | 6/2006 |
| WO | 2012/049317 A2 | 4/2012 |

OTHER PUBLICATIONS

Pertel PE, Spear PG, Longnecker R. Human herpesvirus-8 glycoprotein B interacts with Epstein-Barr virus (EBV) glycoprotein 110 but fails to complement the infectivity of EBV mutants. Virology. Nov. 25, 1998;251(2):402-13.*

(Continued)

*Primary Examiner* — Rachel B Gill
(74) *Attorney, Agent, or Firm* — MH2 Technology Law Group, LLP

(57) ABSTRACT

The present disclosure provides modified human herpesvirus glycoprotein B (gB) proteins that incorporate unique mechanisms for generating proteins that mimic their native conformation to enhance their immunogenicity. The modified herpesvirus gB proteins insert a peptide linker at the furin cleavage site in the extracellular domain of herpesvirus gB. When expressed, the gB subunit associates in triplicate to produce a homotrimeric complex, mimicking the native conformation of the gB protein. Also provided are protein complexes comprising a homotrimeric complex of a modified herpesvirus gB protein and herpesvirus gH and gL proteins. Also provided are nucleic acids encoding the modified herpesvirus gB proteins, methods of inducing or suppressing an immune response in a subject by administering a vaccine comprising the modified herpesvirus gB protein, or nucleic acid encoding the same, or a protein complex comprising a homotrimeric complex of the modified herpesvirus gB protein and herpesvirus gH and gL proteins.

43 Claims, 7 Drawing Sheets

(56) References Cited

OTHER PUBLICATIONS

Oliver SL, Sommer M, Zerboni L, Rajamani J, Grose C, Arvin AM. Mutagenesis of varicella-zoster virus glycoprotein B: putative fusion loop residues are essential for viral replication, and the furin cleavage motif contributes to pathogenesis in skin tissue in vivo. J Virol. Aug. 2009;83(15):7495-506. Epub May 27, 2009.*
"Furin". New England Biolabs, Inc. Product catalog, accessed May 6, 2017; https://www.neb.com/products/p8077-furin.*
Sharma S, Wisner TW, Johnson DC, Heldwein EE. HCMV gB shares structural and functional properties with gB proteins from other herpesviruses. Virology. Jan. 20, 2013;435(2):239-49. doi: 10.1016/j.virol.2012.09.024. Epub Oct. 22, 2012.*
Chen X, Zaro JL, Shen WC. Fusion protein linkers: property, design and functionality. Adv Drug Deliv Rev. Oct. 2013;65(10):1357-69. doi:10.1016/j.addr.2012.09.039. Epub Sep. 29, 2012.*
International Search Report and Written Opinion dated Mar. 13, 2015 from International Application No. PCT/US2014/069856, pp. 1-12.
Oliver et al., "Mutagenesis of varicella-zoster virus glycoprotein B: putative fusion loop residues are essential for viral replication, and the furin cleavage motif contributes to pathogenesis in skin tissue in vivo", Journal of Virology, Aug. 2009, vol. 83, No. 15, pp. 7495-7506.
Lopper et al., "Coiled-Coil Domains in Glycoproteins B and H are Involved in Human Cytomegalovirus Membrane Fusion", Journal of Virology, Aug. 2004, vol. 78, No. 15, pp. 8333-8341.
Pass et al., "Vaccine Prevention of Maternal Cytomegalovirus Infection", The New England Journal of Medicine, Mar. 19, 2009, vol. 360, No. 12, pp. 1191-1199.
Singh et al., "Characterization of a Panel of Insertion Mutants in Human Cytomegalovirus Glycoprotein B", Journal of Virology, Feb. 2000, vol. 74, No. 3, pp. 1383-1392.
Billstrom et al., Postoligomerization folding of human cytomegalovirus glycoprotein B: identification of folding intermediates and importance of disulfide bonding, Journal of Virology, Nov. 1995, vol. 69, No. 11, pp. 7015-7022.
Heldwein et al., "Crystal Structure of Glycoprotein B from Herpes Simplex Virus 1", Science, Jul. 14, 2005, vol. 313, pp. 217-220.
White et al., "Structures and Mechanisms of Viral Membrane Fusion Proteins: Multiple Variations on a Common Theme", Critical Reviews in Biochemistry and Molecular Biology, 2008, vol. 43, pp. 189-219.
Radsak et al., "Retrieval of human cytomegalovirus glycoprotein B from the infected cell surface for virus envelopment", Archives of Virology, 1996, vol. 141, pp. 557-572.
Potzsch et al., "B Cell Repertoire Analysis Identifies New Antigenic Domains on Glycoprotein B of Human Cytomegalovirus which are Target of Neutralizing Antibodies", PLoS Pathogens, Aug. 2011, vol. 7, Issue 8, e1002172, 14 pages.
Lopper et al., "Disulfide Bond Configuration of Human Cytomegalovirus Glycoprotein B", Journal of Virology, Jun. 2002, vol. 76, No. 12, pp. 6073-6082.
Strive et al., "Proteolytic Processing of Human Cytomegalovirus Glycoprotein B is Dispensable for Viral Growth in Culture", Journal of Virology, Feb. 2002, vol. 76, No. 3, pp. 1252-1264.
Backovic et al., "Structure of a trimeric variant of the Epstein-Barr virus glycoprotein B", PNAS, Feb. 24, 2009, vol. 106, No. 8, pp. 2880-2885.
Hahn et al. "Human Cytomegalovirus UL131-128 Genes are Indispensable for Virus Growth in Endothelial Cells and Virus Transfer to Leukocytes." Journal of Virology, Sep. 2004, vol. 78 No. 18, pp. 10023-10033.
Akter et al., "Two novel spliced genes in human cytomegalovirus", Journal of General Virology, 2003, vol. 84, pp. 1117-1122.
Gerna et al., "Dendritic-cell infection by human cytomegalovirus is restricted to strains carrying functinal UL131-128 genes and mediates efficient viral antigen presentation to CD8+ T Cells", Journal of General Virology, 2005, vol. 86, pp. 275-284.
RR Spaete, "A recombinant subunit vaccine approach to HCMV vaccine development", Transplant Proc, 1991, vol. 23, pp. 90-96.
Extended European Search Report (includes Supplementary European Search Report and European Search Opinion), dated Oct. 10, 2017 for European Patent Application No. 14870178.2, 12 pages.
Backovic et al., "Characterization of EBV gB indicates properties of both class I and class II viral fusion proteins", Virology, Elsevier, Amsterdam, NL, 2007, vol. 368, No. 1, pp. 102-113.
Supplementary Partial European Search Report dated Jun. 2, 2017, issued in European Application No. 14 87 0178, 13 pages.
Lilja et al., "The next generation recombinant human cytomegalovirus vaccine candidates—Beyond gB," Vaccine, 2012, vol. 30, No. 49, pp. 6980-6990.
Pass et al., "A Subunit Cytomegalovirus Vaccine Based on Recombinant Envelope Glycoprotein B and a New Adjuvant," Journal of Infectious Diseases, 1999, vol. 180, No. 4, pp. 970-975.

* cited by examiner

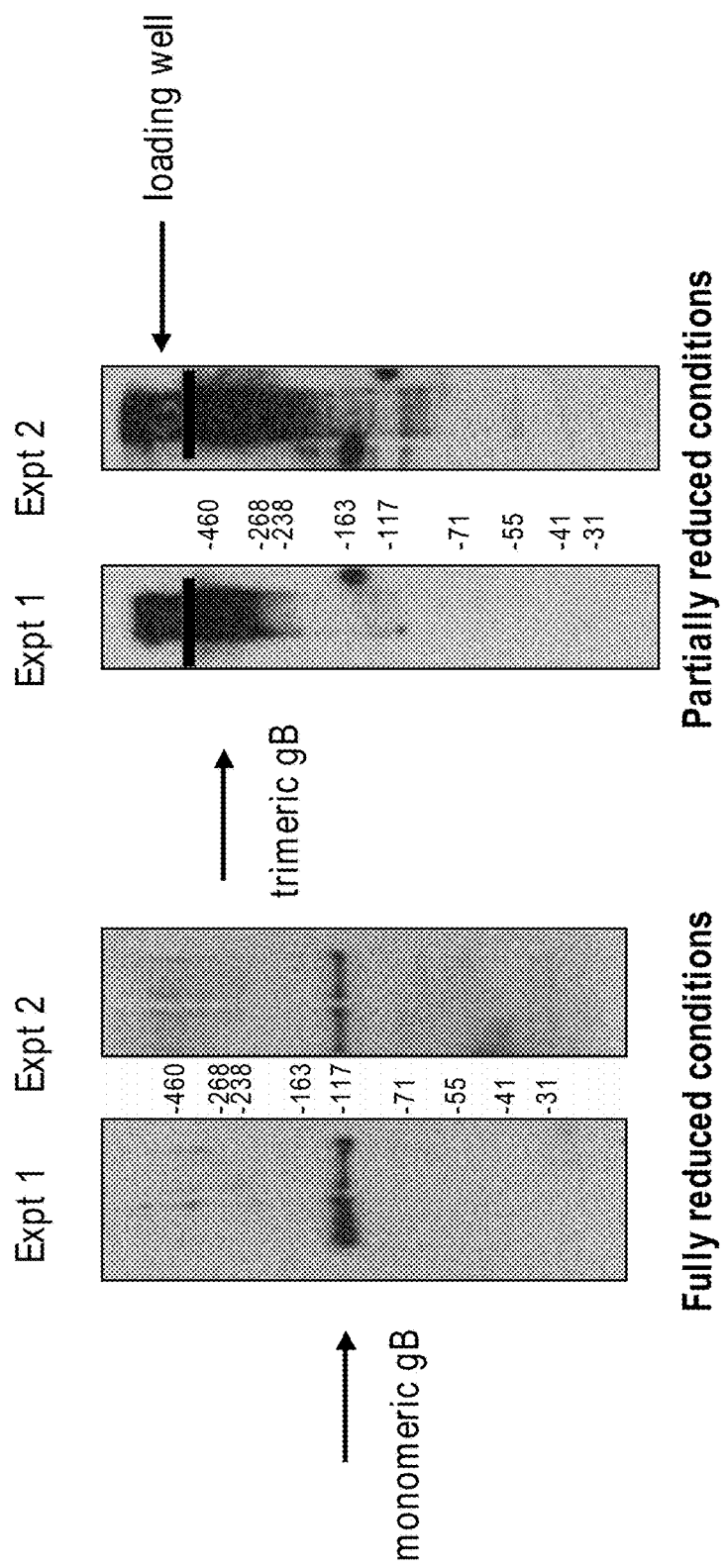

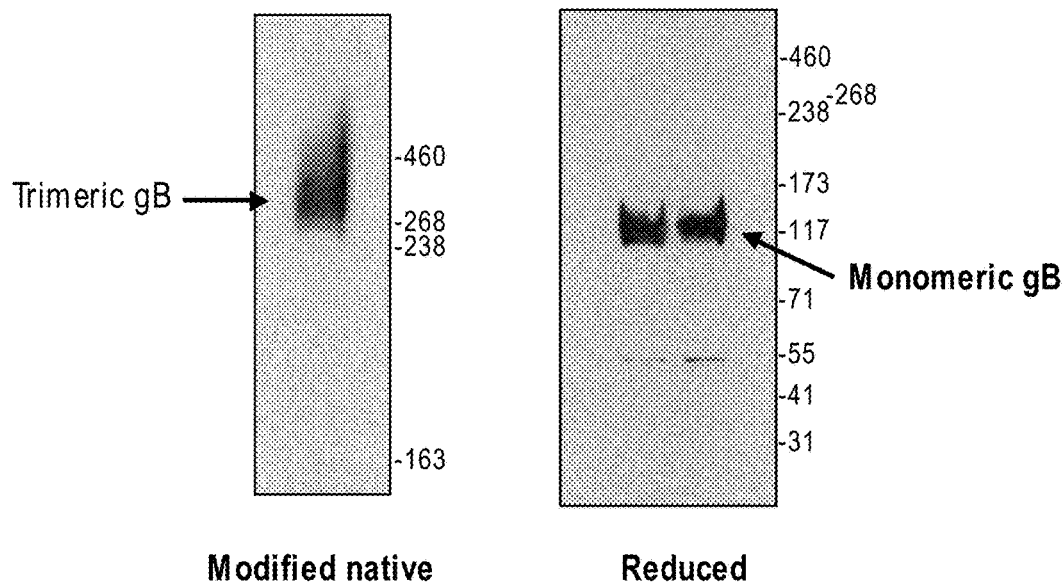
Modified native
FIG. 2A
Reduced
FIG. 2B
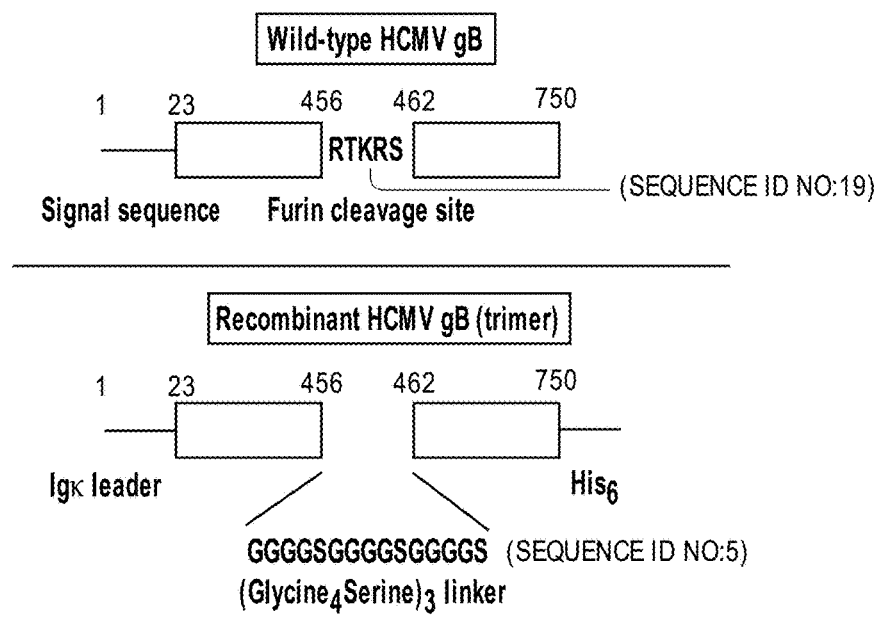
FIG. 3

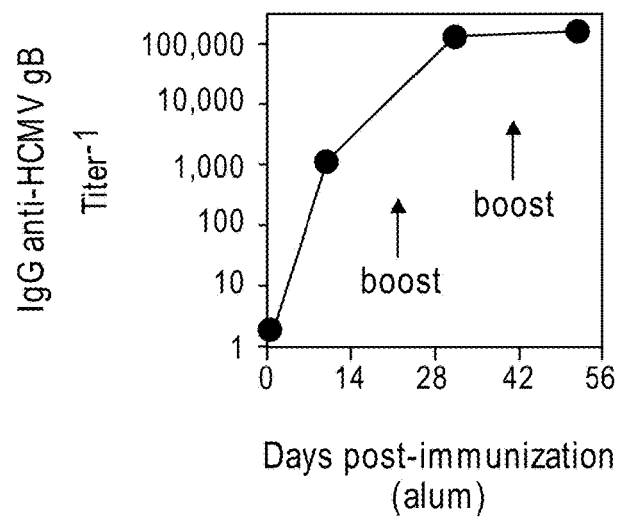
FIG. 5
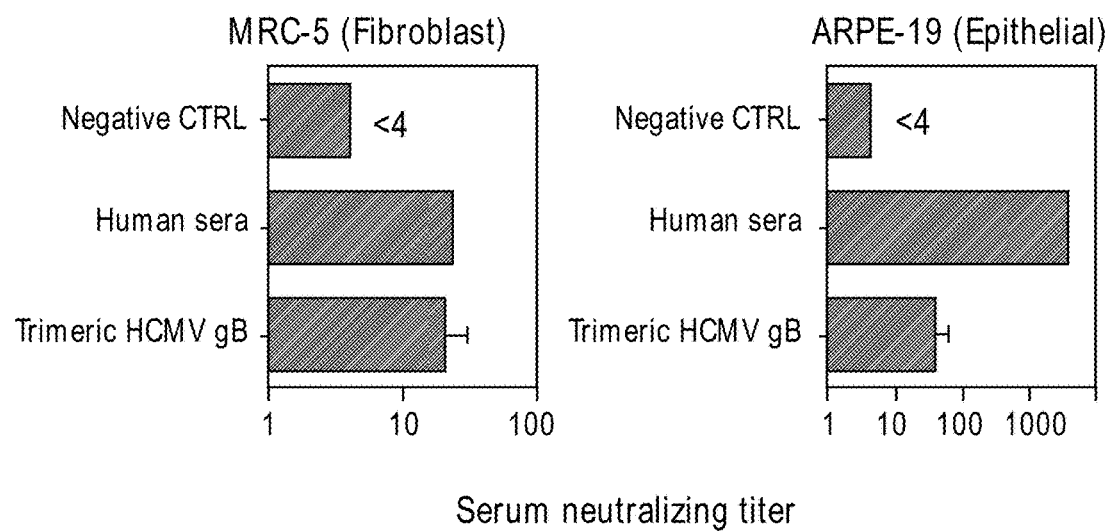
FIG. 6A     FIG. 6B

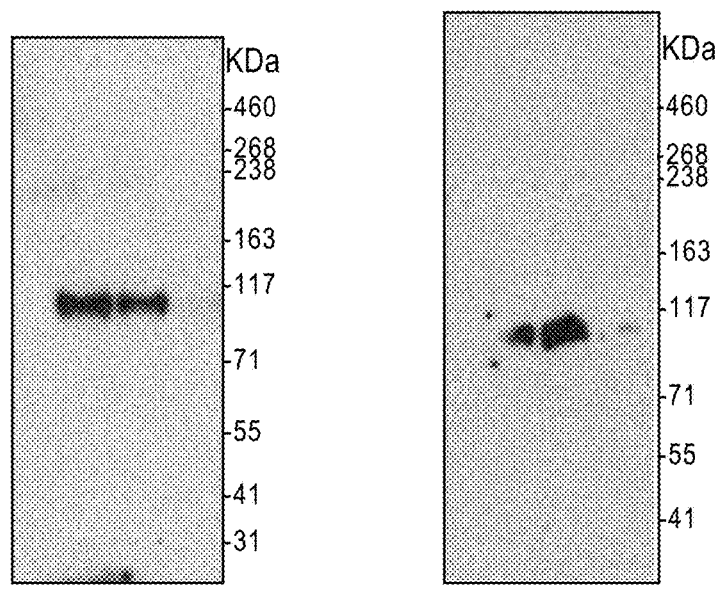
Anti-His mAb
FIG. 9A
Anti-gH mAb
FIG. 9B
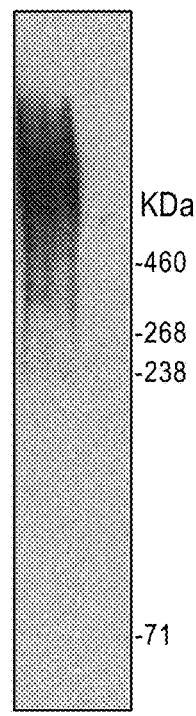
FIG. 10

SEQUENCE LISTING

```
<160> NUMBER OF SEQ ID NOS: 26

<210> SEQ ID NO 1
<211> LENGTH: 2724
<212> TYPE: DNA
<213> ORGANISM: Human cytomegalovirus

<400> SEQUENCE: 1
tcagacgttc tcttcttcgt cagagtcttt caagtgtcgg tagccgtttt tgcgatgtcg      60
cagtcggtct agtaggttgg gcttctgtcc cttgtcctgc gtgccagtcc gtccgtccaa     120
agaatctgta ccgttctgct gcgctcgctg ctctgcgtcc agacgggcca gggccagaag     180
catctggtaa gcctgctcgt tggtgtaagg cggagccgcc gtggatgcat cagacgacgg     240
tggtcccggt cctttgcgac cagaattata aacactttcc tcgtaggaag gcggagcctg     300
taacgacgtg tctttggtgc tgcccgacgt cacggtggtc ccgtcggcgg acaccagata     360
```

```
gggaaagagg ttctgcagcg gctgcgtgca caaacgccgc tgtcgagtat agatcaaata    420
agtgataatg actacagcta tggccacgag gatgatggtg aacgctccga aggggttttt    480
gaggaaggtg gcaacgcctt cgaccacgga ggccaccgcg ccacccacgg ccccaatggc    540
tacgccaacg gccttcccg cggcgcccag gccgctcatg aggtcgtcca gacccttgag     600
gtagggcggt agcgggtcga ctaccttgtc ctccacgtac tttacccgct gcttgtacga    660
gttgaattcg cgcatgatct cttcgaggtc aaaaacgttg ctggaacgca gctcttctg     720
cgagtaaagt tccagtaccc tgaagtcggt attttccagc gggtcgatat ccagggcgat    780
catgctgtcg acggtggaga tactgctgag gtcaatcatg cgtttgaaga ggtagtccac    840
gtactcgtag gccgagttcc cggcgatgaa gatcttgagg ctgggaagct gacattcctc    900
agtgcggtgg ttgcccaaca ggatttcgtt gtcctcgccc agttgaccgt actgcacgta    960
cgagctgttg gcgaaattaa agatgaccac gggtcgtgag tagcagcgtc ctggcgactc    1020
cttcacgttc atatcacgca gcaccttgac gctggtttgg ttgatggtca cgcagctggc    1080
caggcccaag acatcaccca tgaaacgcgc ggcaatcggt ttgttgtaaa tggccgagag    1140
aatggctgac gggttgatct tgctgagttc cttgaagacc tctagggtgc gccgttgatc    1200
cacacaccag gcttctgcga tttgcgccag cgcccggttg atgtaaccgc gcaacgtgtc    1260
ataggtgaac tgcagctggg cgtagaccag attgtgcacc gattccatgt tggataaatg    1320
agttgcattg ttgccatctg tacttctttt ggttctatta tgagtaagat tcagactgga    1380
gcggttggcc aaacgttcga gttccaccag atattttgc ttgataccttgccagaacac     1440
taccaaacca ccagtggttt caaagacgga cacgttccatattttcat atgtttgatt     1500
gtatgaagta ttgaaaatct gctgtaactt atttatagcc tcatcacgta cgcagtccag    1560
cgcagagtcg gacatgttca cctcttgctt cttagataag aaagtggcgg tcattttggc    1620
agaagaaaag tgatacgagt cctcggcttc ggaacgaatg gtgcgttccg aggcttccca    1680
gaaagtgagt tgacaagtga cattctttttc gtcctgtata tcccaggaga tcaccgagtc    1740
cgcacgttca agaaaagcca ccaacctgtg ggtctctaac gcagaattcg gtcttccaaa    1800
gtcggagacg atagtgtagt tcggaaaaat gaaaaacttg tcggcgtttt ctccaaagta    1860
gctggcattg cgattggttc cgttgtagaa aggagaaatg tcaaccacgt cacccgtgga    1920
agtggcgaaa aaatgataag gatatttgga gcgcgcagta gtgatggtca ccatacaatt    1980
cagattacag gtctcacgat agagccaggt gctgccgcgg ctgtgccatt gatccttgac    2040
cgtcacgtaa cgggtactgt gggtgttgga ataatcgtcg ggcattaatt gcatggtttt    2100
gttttcatag ctgtccctat gataagccac gaaaaccgtg cctgctataa cgcggctgta    2160
ggaactgtag cactgactgt ggctgttgat atgatgaatc tcccacatag gaggcgccac    2220
gtattccgtg ttgctgccca gcagataagt ggtgtggatg taagcgtagc tacgacgaaa    2280
cgtcaaaacc ttctggtaga ctcgtacctt aaaggtgtgc gcgacgatgt tgcgtttgta    2340
gaccaccatg atgccctcgt ccaggtcttc attgatgggc ttcatcgagg tgcagacgat    2400
attacgttca aagcgaataa gatccgtacc ctgggccata aacacacgc gatagggta     2460
cttggtggta ttgaccccca ccacatctcc gtacttgagg gtagtgttgt agatggtctc    2520
gttaacacca tggctgaccg tttgggaaga agttacgcgt tgagagactg aaccggatcg    2580
agagtgagca gcagacgtcg tatgagagga atggtgactg tgagtagcag aagttccacg    2640
agtagaagat gaggaaaccg cagcacccag acagacgata cacaagttaa cgcagactac    2700
caggcaccag atcctggatt ccat                                           2724
```

<210> SEQ ID NO 2
<211> LENGTH: 907
<212> TYPE: PRT
<213> ORGANISM: Human cytomegalovirus

<400> SEQUENCE: 2

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
            35                  40                  45

Arg Ser Gly Ser Val Ser Gln Arg Val Thr Ser Ser Gln Thr Val Ser
        50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
```

-continued

```
                370             375             380
Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
            405                 410                 415

Asn Val Ser Val Phe Glu Thr Thr Gly Gly Leu Val Val Phe Trp Gln
                420                 425                 430

Gly Ile Lys Gln Lys Ser Leu Val Glu Leu Glu Arg Leu Ala Asn Arg
            435                 440                 445

Ser Ser Leu Asn Leu Thr His Asn Arg Thr Lys Arg Ser Thr Asp Gly
450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
            515                 520                 525

Leu Ser Ala Ile Tyr Asn Lys Pro Ile Ala Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
            610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
                740                 745                 750

Gly Ala Phe Thr Ile Ile Leu Val Ala Ile Ala Val Val Ile Ile Thr
            755                 760                 765

Tyr Leu Ile Tyr Thr Arg Gln Arg Arg Leu Cys Thr Gln Pro Leu Gln
            770                 775                 780

Asn Leu Phe Pro Tyr Leu Val Ser Ala Asp Gly Thr Thr Val Thr Ser
785                 790                 795                 800
```

```
Gly Ser Thr Lys Asp Thr Ser Leu Gln Ala Pro Pro Ser Tyr Glu Glu
            805                 810                 815
Ser Val Tyr Asn Ser Gly Arg Lys Gly Pro Gly Pro Pro Ser Ser Asp
            820                 825                 830
Ala Ser Thr Ala Ala Pro Pro Tyr Thr Asn Glu Gln Ala Tyr Gln Met
            835                 840                 845
Leu Leu Ala Leu Ala Arg Leu Asp Ala Glu Gln Arg Ala Gln Gln Asn
            850                 855                 860
Gly Thr Asp Ser Leu Asp Gly Arg Thr Gly Thr Gln Asp Lys Gly Gln
865                 870                 875                 880
Lys Pro Asn Leu Leu Asp Arg Leu Arg His Arg Lys Asn Gly Tyr Arg
            885                 890                 895
His Leu Lys Asp Ser Asp Glu Glu Glu Asn Val
            900                 905
```

<210> SEQ ID NO 3
<211> LENGTH: 2343
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| atggagacag acacactcct gctatgggta ctgctgctct gggttccagg ttccactggt | 60 |
| gacgcggccc agccggccag gcgcgcgcgc cgtacgaagc tcgcccttgt ttcctcatct | 120 |
| tctactcgtg gaacttctgc tactcacagt caccattcct ctcatacgac gtctgctgct | 180 |
| cactctcgat ccggttcagt ctctcaacgc gtaacttctt cccaaacggt cagccatggt | 240 |
| gttaacgaga ccatctacaa cactaccctc aagtacggag atgtggtggg ggtcaatacc | 300 |
| accaagtacc cctatcgcgt gtgttctatg gcccagggta cggatcttat tcgctttgaa | 360 |
| cgtaatatcg tctgcacctc gatgaagccc atcaatgaag acctggacga gggcatcatg | 420 |
| gtggtctaca acgcaacat cgtcgcgcac acctttaagg tacgagtcta ccagaaggtt | 480 |
| ttgacgtttc gtcgtagcta cgcttacatc acaccactt atctgctggg cagcaacacg | 540 |
| gaatacgtgg cgcctcctat gtgggagatt catcatatca acagccacag tcagtgctac | 600 |
| agttcctaca gccgcgttat agcaggcacg gttttcgtgg cttatcatag ggacagctat | 660 |
| gaaaacaaaa ccatgcaatt aatgcccgac gattattcca cacccacag tacccgttac | 720 |
| gtgacggtca aggatcaatg gcacagccgc ggcagcacct ggctctatcg tgagacctgt | 780 |
| aatctgaatt gtatggtgac catcactact gcgcgctcca aatatcctta tcatttttc | 840 |
| gccacttcca cgggtgacgt ggttgacatt tctccttct acaacggaac caatcgcaat | 900 |
| gccagctact ttggagaaaa cgccgacaag ttttcattt ttccgaacta cactatcgtc | 960 |
| tccgactttg aagaccgaa ttctgcgtta gagacccaca ggttggtggc ttttcttgaa | 1020 |
| cgtgcggact cggtgatctc ctgggatata caggacgaaa agaatgtcac ttgtcaactc | 1080 |
| actttctggg aagcctcgga acgcaccatt cgttccgaag ccgaggactc gtatcacttt | 1140 |
| tcttctgcca aatgaccgc cactttctta tctaagaagc aagaggtgaa catgtccgac | 1200 |
| tctgcgctgg actgcgtacg tgatgaggct ataaataagt tacagcagat tttcaatact | 1260 |
| tcatacaatc aaacatatga aaaatatgga aacgtgtccg tctttgaaac cactggtggt | 1320 |
| ttggtagtgt tctggcaagg tatcaagcaa aaatctctgg tggaactcga acgtttggcc | 1380 |

-continued

```
aaccgctcca gtctgaatct tactcataat ggtggcggag ggagtggtgg cggagggagc    1440
ggtggcggag ggagtacaga tggcaacaat gcaactcatt tatccaacat ggaatcggtg    1500
cacaatctgg tctacgccca gctgcagttc acctatgaca cgttgcgcgg ttacatcaac    1560
cgggcgctgg cgcaaatcgc agaagcctgg tgtgtggatc aacggcgcac cctagaggtc    1620
ttcaaggaac tcagcaagat caacccgtca gccattctct cggccattta acaaaaccg     1680 attgccgcgc gtttcatggg tgatgtcttg ggcctggcca gctgcgtgac catcaaccaa    1740
accagcgtca aggtgctgcg tgatatgaac gtgaaggagt cgccaggacg ctgctactca    1800
cgacccgtgg tcatctttaa tttcgccaac agctcgtacg tgcagtacgg tcaactgggc    1860
gaggacaacg aaatcctgtt gggcaaccac cgcactgagg aatgtcagct tcccagcctc    1920
aagatcttca tcgccgggaa ctcggcctac gagtacgtgg actacctctt caaacgcatg    1980
attgacctca gcagtatctc caccgtcgac agcatgatcg ccctggatat cgacccgctg    2040
gaaaataccg acttcagggt actggaactt tactcgcaga agagctgcg ttccagcaac      2100 gttttttgacc tcgaagagat catgcgcgaa ttcaactcgt acaagcagcg ggtaaagtac    2160
gtggaggaca aggtagtcga cccgctaccg ccctacctca agggtctgga cgacctcatg    2220
agcggcctgg gcgccgcggg aaaggccgtt ggcgtagcca ttggggccgt gggtggcgcg    2280
gtggcctccg tggtcgaagg cgttgccacc ttcctcaaaa accatcatca ccatcaccat    2340
tga                                                                  2343
```

<210> SEQ ID NO 4
<211> LENGTH: 780
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ala Leu Val Ser Ser Ser Thr Arg Gly Thr Ser Ala Thr
        35                  40                  45

His Ser His His Ser Ser His Thr Ser Ala Ala His Ser Arg Ser
    50                  55                  60

Gly Ser Val Ser Gln Arg Val Thr Ser Ser Gln Thr Val Ser His Gly
65                  70                  75                  80

Val Asn Glu Thr Ile Tyr Asn Thr Thr Leu Lys Tyr Gly Asp Val Val
                85                  90                  95

Gly Val Asn Thr Thr Lys Tyr Pro Tyr Arg Val Cys Ser Met Ala Gln
            100                 105                 110

Gly Thr Asp Leu Ile Arg Phe Glu Arg Asn Ile Val Cys Thr Ser Met
        115                 120                 125

Lys Pro Ile Asn Glu Asp Leu Asp Glu Gly Ile Met Val Val Tyr Lys
    130                 135                 140

Arg Asn Ile Val Ala His Thr Phe Lys Val Arg Val Tyr Gln Lys Val
145                 150                 155                 160

Leu Thr Phe Arg Arg Ser Tyr Ala Tyr Ile His Thr Thr Tyr Leu Leu
                165                 170                 175

Gly Ser Asn Thr Glu Tyr Val Ala Pro Pro Met Trp Glu Ile His His
```

```
                180               185               190
Ile Asn Ser His Ser Gln Cys Tyr Ser Ser Tyr Ser Arg Val Ile Ala
            195                   200                   205
Gly Thr Val Phe Val Ala Tyr His Arg Asp Ser Tyr Glu Asn Lys Thr
210                     215                   220
Met Gln Leu Met Pro Asp Asp Tyr Ser Asn Thr His Ser Thr Arg Tyr
225                     230                   235                   240
Val Thr Val Lys Asp Gln Trp His Ser Arg Gly Ser Thr Trp Leu Tyr
            245                   250                   255
Arg Glu Thr Cys Asn Leu Asn Cys Met Val Thr Ile Thr Thr Ala Arg
                260                   265                   270
Ser Lys Tyr Pro Tyr His Phe Phe Ala Thr Ser Thr Gly Asp Val Val
            275                   280                   285
Asp Ile Ser Pro Phe Tyr Asn Gly Thr Asn Arg Asn Ala Ser Tyr Phe
290                     295                   300
Gly Glu Asn Ala Asp Lys Phe Phe Ile Phe Pro Asn Tyr Thr Ile Val
305                     310                   315                   320
Ser Asp Phe Gly Arg Pro Asn Ser Ala Leu Glu Thr His Arg Leu Val
                325                   330                   335
Ala Phe Leu Glu Arg Ala Asp Ser Val Ile Ser Trp Asp Ile Gln Asp
                340                   345                   350
Glu Lys Asn Val Thr Cys Gln Leu Thr Phe Trp Glu Ala Ser Glu Arg
                355                   360                   365
Thr Ile Arg Ser Glu Ala Glu Asp Ser Tyr His Phe Ser Ser Ala Lys
                370                   375                   380
Met Thr Ala Thr Phe Leu Ser Lys Lys Gln Glu Val Asn Met Ser Asp
385                     390                   395                   400
Ser Ala Leu Asp Cys Val Arg Asp Glu Ala Ile Asn Lys Leu Gln Gln
                405                   410                   415
Ile Phe Asn Thr Ser Tyr Asn Gln Thr Tyr Glu Lys Tyr Gly Asn Val
                420                   425                   430
Ser Val Phe Glu Thr Thr Gly Gly Leu Val Val Phe Trp Gln Gly Ile
            435                   440                   445
Lys Gln Lys Ser Leu Val Glu Leu Glu Arg Leu Ala Asn Arg Ser Ser
            450                   455                   460
Leu Asn Leu Thr His Asn Gly Gly Gly Ser Gly Gly Gly Gly Gly Ser
465                     470                   475                   480
Gly Gly Gly Gly Ser Thr Asp Gly Asn Asn Ala Thr His Leu Ser Asn
                485                   490                   495
Met Glu Ser Val His Asn Leu Val Tyr Ala Gln Leu Gln Phe Thr Tyr
                500                   505                   510
Asp Thr Leu Arg Gly Tyr Ile Asn Arg Ala Leu Ala Gln Ile Ala Glu
            515                   520                   525
Ala Trp Cys Val Asp Gln Arg Arg Thr Leu Glu Val Phe Lys Glu Leu
            530                   535                   540
Ser Lys Ile Asn Pro Ser Ala Ile Leu Ser Ala Ile Tyr Asn Lys Pro
545                     550                   555                   560
Ile Ala Ala Arg Phe Met Gly Asp Val Leu Gly Leu Ala Ser Cys Val
                565                   570                   575
Thr Ile Asn Gln Thr Ser Val Lys Val Leu Arg Asp Met Asn Val Lys
                580                   585                   590
Glu Ser Pro Gly Arg Cys Tyr Ser Arg Pro Val Val Ile Phe Asn Phe
                595                   600                   605
```

```
Ala Asn Ser Ser Tyr Val Gln Tyr Gly Gln Leu Gly Glu Asp Asn Glu
        610                 615                 620

Ile Leu Leu Gly Asn His Arg Thr Glu Glu Cys Gln Leu Pro Ser Leu
625                 630                 635                 640

Lys Ile Phe Ile Ala Gly Asn Ser Ala Tyr Glu Tyr Val Asp Tyr Leu
                645                 650                 655

Phe Lys Arg Met Ile Asp Leu Ser Ser Ile Ser Thr Val Asp Ser Met
            660                 665                 670

Ile Ala Leu Asp Ile Asp Pro Leu Glu Asn Thr Asp Phe Arg Val Leu
        675                 680                 685

Glu Leu Tyr Ser Gln Lys Glu Leu Arg Ser Ser Asn Val Phe Asp Leu
    690                 695                 700

Glu Glu Ile Met Arg Glu Phe Asn Ser Tyr Lys Gln Arg Val Lys Tyr
705                 710                 715                 720

Val Glu Asp Lys Val Val Asp Pro Leu Pro Pro Tyr Leu Lys Gly Leu
                725                 730                 735

Asp Asp Leu Met Ser Gly Leu Gly Ala Ala Gly Lys Ala Val Gly Val
            740                 745                 750

Ala Ile Gly Ala Val Gly Gly Ala Val Ala Ser Val Val Glu Gly Val
        755                 760                 765

Ala Thr Phe Leu Lys Asn His His His His His His
770                 775                 780

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Glu Thr Asp Thr Leu Leu Leu Trp Val Leu Leu Leu Trp Val Pro
1               5                   10                  15

Gly Ser Thr Gly Asp
            20

<210> SEQ ID NO 7
<211> LENGTH: 2574
<212> TYPE: DNA
<213> ORGANISM: Epstein-Barr virus

<400> SEQUENCE: 7
atgactcggc gtagggtgct aagcgtggtc gtgctgctag ccgccctggc gtgccgcctc        60
ggtgcgcaga cccagagcag cccgcaccc cccgccacca cggtgcagcc taccgccacg       120
cgtcagcaaa ccagctttcc tttccgagtc tgcgagctct ccagccacgg cgacctgttc       180
```

-continued

```
cgcttctcct cggacatcca gtgtccctcg tttggcacgc gggagaatca cacggagggc     240
ctgttgatgg tgtttaaaga caacattatt ccctactcgt ttaaggtccg ctcctacacc     300
aagatagtga ccaacattct catctacaat ggctggtacg cggactccgt gaccaaccgg     360
cacgaggaga agttctccgt tgacagctac gaaactgacc agatggatac catctaccag     420
tgctacaacg cggtcaagat gacaaaagat gggctgacgc gcgtgtatgt agaccgcgac     480
ggagttaaca tcaccgtcaa cctaaagccc accgggggcc tggccaacgg ggtgcgccgc     540
tacgccagcc agacggagct ctatgacgcc cccgggtggt tgatatggac ttacagaaca     600
agaactaccg tcaactgcct gataactgac atgatggcca agtccaacag ccccttcgac     660
ttctttgtga ccaccaccgg gcagactgtg aaatgtccc ctttctatga cgggaaaaat     720
aaggaaacct tccatgagcg ggcagactcc ttccacgtga aactaacta caagatagtg     780 gactacgaca accgagggac gaacccgcaa ggcgaacgcc gagccttcct ggacaagggc     840
acttacaccc tatcttggaa gctcgagaac aggacagcct actgcccgct tcaacactgg     900
caaacctttg actcgaccat cgccacagaa acagggaagt caatacattt tgtgactgac     960
gagggcacct ctagcttcgt gaccaacaca accgtgggca tagagctccc ggacgccttc    1020
aagtgcatcg aagagcaggt gaacaagacc atgcatgaga agtacgaggc cgtccaggat    1080
cgttacacga agggccagga agccattaca tattttataa cgagcggagg attgttatta    1140
gcttggctac ctctgacccc gcgctcgttg gccaccgtca agaacctgac ggagcttacc    1200
actccgactt cctcaccccc cagcagtcca tcgcccccg ccccaccgc ggcccgcggg    1260 agcacctccg ccgccgttct gaggcgccgg aggcgggatg cggggaatgc caccacaccg    1320
gtgccccccg cggcccccgg gaagtccctg ggcaccctca acaatcccgc caccgtccag    1380
atccaatttg cctacgattc cctgcgccgc cagatcaacc gcatgctggg agacctcgcg    1440
cgggcctggt gcctggagca gaagaggcag aacatggtgc tgagagaact aaccaagatt    1500
aatcccacca ccgtcatgtc cagcatctac ggtaaggcgg tggcggccaa cgcctgggg    1560 gatgtcatct cagtctccca gtgcgtgccc gttaaccagg ccaccgtcac cctgcgcaag    1620
agcatgaggt ccctggctc cgagaccatg tgctactcgc gcccctggt gtccttcagc    1680 tttatcaacg acaccaagac ctacgaggga cagctgggca ccgacaacga gatcttcctc    1740
acaaaaaaga tgacggaggt gtgccaggcg accagccagt actacttcca gtccggcaac    1800
gagatccacg tctacaacga ctaccaccac tttaaaacca tcgagctgga cggcattgcc    1860
accctgcaga ccttcatctc actaaacacc tccctcatcg agaacattga ctttgcctcc    1920
ctggagctgt actcacggga cgaacagcgt gcctccaacg tctttgacct ggagggcatc    1980
ttccgggagt acaacttcca ggcgcaaaac atcgccggcc tgcggaagga tttggacaat    2040
gcagtgtcaa acggaagaaa tcaattcgtg gacggcctgg gggaacttat ggacagtctg    2100
ggtagcgtgg gtcagtccat caccaaccta gtcagcacgg tgggggttt gtttagcagc    2160 ctggtctctg gtttcatctc cttcttcaaa aaccccttcg gcggcatgct cattctggtc    2220
ctggtggcgg gggtggtgat cctggttatt ccctcacga ggcgcacgcg ccagatgtcg    2280
cagcagccgt gcagatgct ctaccccggg atcgacgagc tcgctcagca acatgcctct    2340
ggtgagggtc caggcattaa tcccattagt aagacagaat acaagccat catgttagcg    2400 ctgcatgagc aaaaccagga gcaaaagaga gcagctcaga gggcggccgg accctcagtg    2460
gccagcagag cattgcaggc agccaggac cgttttccag gcctacgcag aagacgctat    2520
cacgatccag agaccgccgc cgcactgctt ggggaggcag agactgagtt ttaa          2574
```

<210> SEQ ID NO 8
<211> LENGTH: 857
<212> TYPE: PRT
<213> ORGANISM: Epstein-Barr virus

<400> SEQUENCE: 8

Met Thr Arg Arg Val Leu Ser Val Val Leu Ala Ala Leu
1               5                   10                  15

Ala Cys Arg Leu Gly Ala Gln Thr Pro Glu Gln Pro Ala Pro Ala
            20                  25                  30

Thr Thr Val Gln Pro Thr Ala Thr Arg Gln Gln Thr Ser Phe Pro Phe
            35                  40                  45

Arg Val Cys Glu Leu Ser Ser His Gly Asp Leu Phe Arg Phe Ser Ser
        50                  55                  60

Asp Ile Gln Cys Pro Ser Phe Gly Thr Arg Glu Asn His Thr Glu Gly
65                  70                  75                  80

Leu Leu Met Val Phe Lys Asp Asn Ile Ile Pro Tyr Ser Phe Lys Val
                85                  90                  95

Arg Ser Tyr Thr Lys Ile Val Thr Asn Ile Leu Ile Tyr Asn Gly Trp
            100                 105                 110

Tyr Ala Asp Ser Val Thr Asn Arg His Glu Glu Lys Phe Ser Val Asp
        115                 120                 125

Ser Tyr Glu Thr Asp Gln Met Asp Thr Ile Tyr Gln Cys Tyr Asn Ala
130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Gly Leu Ala Asn
                165                 170                 175

Gly Val Arg Arg Tyr Ala Ser Gln Thr Glu Leu Tyr Asp Ala Pro Gly
            180                 185                 190

Trp Leu Ile Trp Thr Tyr Arg Thr Arg Thr Thr Val Asn Cys Leu Ile
        195                 200                 205

Thr Asp Met Met Ala Lys Ser Asn Ser Pro Phe Asp Phe Phe Val Thr
210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
                245                 250                 255

Tyr Lys Ile Val Asp Tyr Asp Asn Arg Gly Thr Asn Pro Gln Gly Glu
            260                 265                 270

Arg Arg Ala Phe Leu Asp Lys Gly Thr Tyr Thr Leu Ser Trp Lys Leu
        275                 280                 285

Glu Asn Arg Thr Ala Tyr Cys Pro Leu Gln His Trp Gln Thr Phe Asp
290                 295                 300

Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                325                 330                 335

Pro Asp Ala Phe Lys Cys Ile Glu Glu Gln Val Asn Lys Thr Met His
            340                 345                 350

Glu Lys Tyr Glu Ala Val Gln Asp Arg Tyr Thr Lys Gly Gln Glu Ala
        355                 360                 365

Ile Thr Tyr Phe Ile Thr Ser Gly Gly Leu Leu Leu Ala Trp Leu Pro

```
              370                 375                 380
Leu Thr Pro Arg Ser Leu Ala Thr Val Lys Asn Leu Thr Glu Leu Thr
385                 390                 395                 400

Thr Pro Thr Ser Ser Pro Pro Ser Ser Pro Ser Pro Ala Pro Pro
                405                 410                 415

Ala Ala Arg Gly Ser Thr Ser Ala Ala Val Leu Arg Arg Arg Arg
            420                 425                 430

Asp Ala Gly Asn Ala Thr Thr Pro Val Pro Ala Ala Pro Gly Lys
            435                 440                 445

Ser Leu Gly Thr Leu Asn Asn Pro Ala Thr Val Gln Ile Gln Phe Ala
450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                485                 490                 495

Leu Thr Lys Ile Asn Pro Thr Thr Val Met Ser Ser Ile Tyr Gly Lys
            500                 505                 510

Ala Val Ala Ala Lys Arg Leu Gly Asp Val Ile Ser Val Ser Gln Cys
            515                 520                 525

Val Pro Val Asn Gln Ala Thr Val Thr Leu Arg Lys Ser Met Arg Val
530                 535                 540

Pro Gly Ser Glu Thr Met Cys Tyr Ser Arg Pro Leu Val Ser Phe Ser
545                 550                 555                 560

Phe Ile Asn Asp Thr Lys Thr Tyr Glu Gly Gln Leu Gly Thr Asp Asn
                565                 570                 575

Glu Ile Phe Leu Thr Lys Lys Met Thr Glu Val Cys Gln Ala Thr Ser
            580                 585                 590

Gln Tyr Tyr Phe Gln Ser Gly Asn Glu Ile His Val Tyr Asn Asp Tyr
            595                 600                 605

His His Phe Lys Thr Ile Glu Leu Asp Gly Ile Ala Thr Leu Gln Thr
610                 615                 620

Phe Ile Ser Leu Asn Thr Ser Leu Ile Glu Asn Ile Asp Phe Ala Ser
625                 630                 635                 640

Leu Glu Leu Tyr Ser Arg Asp Glu Gln Arg Ala Ser Asn Val Phe Asp
                645                 650                 655

Leu Glu Gly Ile Phe Arg Glu Tyr Asn Phe Gln Ala Gln Asn Ile Ala
            660                 665                 670

Gly Leu Arg Lys Asp Leu Asp Asn Ala Val Ser Asn Gly Arg Asn Gln
            675                 680                 685

Phe Val Asp Gly Leu Gly Glu Leu Met Asp Ser Leu Gly Ser Val Gly
690                 695                 700

Gln Ser Ile Thr Asn Leu Val Ser Thr Val Gly Gly Leu Phe Ser Ser
705                 710                 715                 720

Leu Val Ser Gly Phe Ile Ser Phe Phe Lys Asn Pro Phe Gly Gly Met
                725                 730                 735

Leu Ile Leu Val Leu Val Ala Gly Val Val Ile Leu Val Ile Ser Leu
            740                 745                 750

Thr Arg Arg Thr Arg Gln Met Ser Gln Gln Pro Val Gln Met Leu Tyr
            755                 760                 765

Pro Gly Ile Asp Glu Leu Ala Gln Gln His Ala Ser Gly Glu Gly Pro
770                 775                 780

Gly Ile Asn Pro Ile Ser Lys Thr Glu Leu Gln Ala Ile Met Leu Ala
785                 790                 795                 800
```

| Leu | His | Glu | Gln | Asn | Gln | Glu | Gln | Lys | Arg | Ala | Ala | Gln | Arg | Ala | Ala |
|-----|-----|-----|-----|-----|-----|-----|-----|-----|-----|-----|-----|-----|-----|-----|-----|
|     |     |     |     | 805 |     |     |     |     | 810 |     |     |     |     | 815 |     |

| Gly | Pro | Ser | Val | Ala | Ser | Arg | Ala | Leu | Gln | Ala | Ala | Arg | Asp | Arg | Phe |
|-----|-----|-----|-----|-----|-----|-----|-----|-----|-----|-----|-----|-----|-----|-----|-----|
|     |     |     | 820 |     |     |     |     | 825 |     |     |     |     | 830 |     |     |

| Pro | Gly | Leu | Arg | Arg | Arg | Arg | Tyr | His | Asp | Pro | Glu | Thr | Ala | Ala | Ala |
|-----|-----|-----|-----|-----|-----|-----|-----|-----|-----|-----|-----|-----|-----|-----|-----|
|     |     |     | 835 |     |     |     |     | 840 |     |     |     |     | 845 |     |     |

| Leu | Leu | Gly | Glu | Ala | Glu | Thr | Glu | Phe |
|-----|-----|-----|-----|-----|-----|-----|-----|-----|
|     | 850 |     |     |     |     | 855 |     |     |

<210> SEQ ID NO 9
<211> LENGTH: 2235
<212> TYPE: DNA
<213> ORGANISM: Epstein-Barr virus

<400> SEQUENCE: 9

```
atggagacag acacactcct gctatgggta ctgctgctct gggttccagg ttccactggt    60
gacgcggccc agaccccaga gcagcccgca cccccgcca ccacggtgca gcctaccgcc    120
acgcgtcagc aaaccagctt cctttccga gtctgcgagc tctccagcca cggcgacctg    180
ttccgcttct cctcggacat ccagtgtccc tcgtttggca cgcgggagaa tcacacggag    240
ggcctgttga tggtgtttaa agacaacatt attccctact cgtttaaggt ccgctcctac    300
accaagatag tgaccaacat tctcatctac aatggctggt acgcggactc cgtgaccaac    360
cggcacgagg agaagttctc cgttgacagc tacgaaactg accagatgga taccatctac    420
cagtgctaca acgcggtcaa gatgacaaaa gatgggctga cgcgcgtgta tgtagaccgc    480
gacggagtta acatcaccgt caacctaaag cccaccgggg gcctggccaa cggggtgcgc    540
cgctacgcca gccagacgga gctctatgac gcccccgggt ggttgatatg gacttacaga    600
acaagaacta ccgtcaactg cctgataact gacatgatgg ccaagtccaa cagcccettc    660
gacttctttg tgaccaccac cgggcagact gtggaaatgt cccctttcta tgacgggaaa    720
aataaggaaa ccttccatga gcgggcagac tccttccacg tgagaactaa ctacaagata    780
gtggactacg acaaccgagg gacgaacccg caaggcgaac gccgagcctt cctggacaag    840
ggcacttaca cctatcttg gaagctcgag aacaggacag cctactgccc gcttcaacac    900
tggcaaacct tgactcgac catcgccaca gaaacaggga agtcaataca ttttgtgact    960
gacgagggca cctctagctt cgtgaccaac acaaccgtgg gcatagagct cccggacgcc   1020
ttcaagtgca tcgaagagca ggtgaacaag accatgcatg agaagtacga ggccgtccag   1080
gatcgttaca cgaagggcca ggaagccatt acatatttta acgagcgg aggattgtta   1140
ttagcttggc tacctctgac cccgcgctcg ttggccaccg tcaagaacct gacggagctt   1200
accactccga cttcctcacc cccagcagt ccatcgcccc cgccccacc cgcggcccgc   1260
gggagcacct ccgccgccgt tctgaggcgc ggtggcggag ggagtggtgg cggagggagc   1320
ggtggcggag ggagtgcggg gaatgccacc acaccggtgc cccccgcggc cccgggaag   1380
tccctgggca ccctcaacaa tccgccacc gtccagatcc aatttgccta cgattccctg   1440
cgccgccaga tcaaccgcat gctgggagac ctcgcgcggg cctggtgcct ggagcagaag   1500
aggcagaaca tggtgctgag agaactaacc aagattaatc ccaccaccgt catgtccagc   1560
atctacggta aggcggtggc ggccaagcgc ctggggatg tcatctcagt ctcccagtgc   1620
gtgcccgtta accaggccac cgtcaccctg gcaagagca tgagggtccc tggctccgag   1680
accatgtgct actcgcgccc cctggtgtcc ttcagcttta tcaacgacac caagacctac   1740
```

```
gagggacagc tgggcaccga caacgagatc ttcctcacaa aaaagatgac ggaggtgtgc    1800
caggcgacca gccagtacta cttccagtcc ggcaacgaga tccacgtcta caacgactac    1860
caccacttta aaccatcga gctggacggc attgccaccc tgcagacctt catctcacta    1920
aacacctccc tcatcgagaa cattgacttt gcctccctgg agctgtactc acgggacgaa    1980
cagcgtgcct ccaacgtctt tgacctggag ggcatcttcc gggagtacaa cttccaggcg    2040
caaaacatcg ccggcctgcg gaaggatttg gacaatgcag tgtcaaacgg aagaaatcaa    2100
ttcgtggacg gcctggggga acttatggac agtctgggta gcgtgggtca gtccatcacc    2160
aacctagtca gcacggtggg gggtttgttt agcagcctgg tctctggttt catctccttc    2220
ttcaaaaacc cctaa                                                    2235
```

<210> SEQ ID NO 10
<211> LENGTH: 743
<212> TYPE: PRT
<213> ORGANISM: Epstein-Barr virus

<400> SEQUENCE: 10

```
Met Glu Thr Asp Thr Leu Leu Leu Trp Val Leu Leu Trp Val Pro
1               5                   10                  15

Gly Ser Thr Gly Asp Ala Ala Gln Thr Pro Glu Gln Pro Ala Pro
                20                  25                  30

Ala Thr Thr Val Gln Pro Thr Ala Thr Arg Gln Thr Ser Phe Pro
            35                  40                  45

Phe Arg Val Cys Glu Leu Ser Ser His Gly Asp Leu Phe Arg Phe Ser
50                  55                  60

Ser Asp Ile Gln Cys Pro Ser Phe Gly Thr Arg Glu Asn His Thr Glu
65                  70                  75                  80

Gly Leu Leu Met Val Phe Lys Asp Asn Ile Ile Pro Tyr Ser Phe Lys
                85                  90                  95

Val Arg Ser Tyr Thr Lys Ile Val Thr Asn Ile Leu Ile Tyr Asn Gly
            100                 105                 110

Trp Tyr Ala Asp Ser Val Thr Asn Arg His Glu Glu Lys Phe Ser Val
        115                 120                 125

Asp Ser Tyr Glu Thr Asp Gln Met Asp Thr Ile Tyr Gln Cys Tyr Asn
    130                 135                 140

Ala Val Lys Met Thr Lys Asp Gly Leu Thr Arg Val Tyr Val Asp Arg
145                 150                 155                 160

Asp Gly Val Asn Ile Thr Val Asn Leu Lys Pro Thr Gly Gly Leu Ala
                165                 170                 175

Asn Gly Val Arg Arg Tyr Ala Ser Gln Thr Glu Leu Tyr Asp Ala Pro
            180                 185                 190

Gly Trp Leu Ile Trp Thr Tyr Arg Thr Arg Thr Thr Val Asn Cys Leu
        195                 200                 205

Ile Thr Asp Met Met Ala Lys Ser Asn Ser Pro Phe Asp Phe Phe Val
    210                 215                 220

Thr Thr Thr Gly Gln Thr Val Glu Met Ser Pro Phe Tyr Asp Gly Lys
225                 230                 235                 240

Asn Lys Glu Thr Phe His Glu Arg Ala Asp Ser Phe His Val Arg Thr
                245                 250                 255

Asn Tyr Lys Ile Val Asp Tyr Asp Asn Arg Gly Thr Asn Pro Gln Gly
            260                 265                 270

Glu Arg Arg Ala Phe Leu Asp Lys Gly Thr Tyr Thr Leu Ser Trp Lys
        275                 280                 285
```

```
Leu Glu Asn Arg Thr Ala Tyr Cys Pro Leu Gln His Trp Gln Thr Phe
    290                 295                 300

Asp Ser Thr Ile Ala Thr Glu Thr Gly Lys Ser Ile His Phe Val Thr
305                 310                 315                 320

Asp Glu Gly Thr Ser Ser Phe Val Thr Asn Thr Thr Val Gly Ile Glu
                325                 330                 335

Leu Pro Asp Ala Phe Lys Cys Ile Glu Glu Gln Val Asn Lys Thr Met
                340                 345                 350

His Glu Lys Tyr Glu Ala Val Gln Asp Arg Tyr Thr Lys Gly Gln Glu
            355                 360                 365

Ala Ile Thr Tyr Phe Ile Thr Ser Gly Leu Leu Leu Ala Trp Leu
    370                 375                 380

Pro Leu Thr Pro Arg Ser Leu Ala Thr Val Lys Asn Leu Thr Glu Leu
385                 390                 395                 400

Thr Thr Pro Thr Ser Ser Pro Pro Ser Ser Pro Pro Ala Pro
                405                 410                 415

Pro Ala Ala Arg Gly Ser Thr Ser Ala Ala Val Leu Arg Gly Gly Gly
                420                 425                 430

Gly Ser Gly Gly Gly Gly Ser Gly Gly Gly Ser Ala Gly Asn Ala
            435                 440                 445

Thr Thr Pro Val Pro Pro Ala Ala Pro Gly Lys Ser Leu Gly Thr Leu
    450                 455                 460

Asn Asn Pro Ala Thr Val Gln Ile Gln Phe Ala Tyr Asp Ser Leu Arg
465                 470                 475                 480

Arg Gln Ile Asn Arg Met Leu Gly Asp Leu Ala Arg Ala Trp Cys Leu
                485                 490                 495

Glu Gln Lys Arg Gln Asn Met Val Leu Arg Glu Leu Thr Lys Ile Asn
                500                 505                 510

Pro Thr Thr Val Met Ser Ser Ile Tyr Gly Lys Ala Val Ala Ala Lys
                515                 520                 525

Arg Leu Gly Asp Val Ile Ser Val Ser Gln Cys Val Pro Val Asn Gln
530                 535                 540

Ala Thr Val Thr Leu Arg Lys Ser Met Arg Val Pro Gly Ser Glu Thr
545                 550                 555                 560

Met Cys Tyr Ser Arg Pro Leu Val Ser Phe Ser Phe Ile Asn Asp Thr
                565                 570                 575

Lys Thr Tyr Glu Gly Gln Leu Gly Thr Asp Asn Glu Ile Phe Leu Thr
                580                 585                 590

Lys Lys Met Thr Glu Val Cys Gln Ala Thr Ser Gln Tyr Tyr Phe Gln
            595                 600                 605

Ser Gly Asn Glu Ile His Val Tyr Asn Asp Tyr His His Phe Lys Thr
    610                 615                 620

Ile Glu Leu Asp Gly Ile Ala Thr Leu Gln Thr Phe Ile Ser Leu Asn
625                 630                 635                 640

Thr Ser Leu Ile Glu Asn Ile Asp Phe Ala Ser Leu Glu Leu Tyr Ser
                645                 650                 655

Arg Asp Glu Gln Arg Ala Ser Asn Val Phe Asp Leu Glu Gly Ile Phe
                660                 665                 670

Arg Glu Tyr Asn Phe Gln Ala Gln Asn Ile Ala Gly Leu Arg Lys Asp
            675                 680                 685

Leu Asp Asn Ala Val Ser Asn Gly Arg Asn Gln Phe Val Asp Gly Leu
    690                 695                 700
```

Gly Glu Leu Met Asp Ser Leu Gly Ser Val Gly Gln Ser Ile Thr Asn
705                 710                 715                 720

Leu Val Ser Thr Val Gly Gly Leu Phe Ser Ser Leu Val Ser Gly Phe
                725                 730                 735

Ile Ser Phe Phe Lys Asn Pro
            740

<210> SEQ ID NO 11
<211> LENGTH: 2715
<212> TYPE: DNA
<213> ORGANISM: Herpes simplex virus 1

<400> SEQUENCE: 11

| | | | | | | |
|---|---|---|---|---|---|---|
| atgcgccagg | gcgccccgc | gcggggcgc | cggtggttcg | tcgtatgggc | gctcttgggg | 60 |
| ttgacgctgg | gggtcctggt | ggcgtcggcg | gctccgagtt | ccccggcac | gcctggggtc | 120 |
| gcggccgcga | cccaggcggc | gaacgggggc | cctgccactc | cggcgccgcc | cgccctggc | 180 |
| gccccccaa | cggggaccc | gaaaccgaag | aagaacagaa | aaccgaaacc | cccaaagccg | 240 |
| ccgcgccccg | ccggcgacaa | cgcgaccgtc | gccgcgggcc | acgccaccct | gcgcgagcac | 300 |
| ctgcgggaca | tcaaggcgga | gaacaccgat | gcaaactttt | acgtgtgccc | acccccacg | 360 |
| ggcgccacgg | tggtgcagtt | cgagcagccg | cgccgctgcc | cgacccggcc | cgagggtcag | 420 |
| aactacacgg | agggcatcgc | ggtggtcttc | aaggagaaca | tcgccccgta | caagttcaag | 480 |
| gccaccatgt | actacaaaga | cgtcaccgtt | tcgcaggtgt | ggttcggcca | ccgctactcc | 540 |
| cagtttatgg | ggatctttga | ggaccgcgcc | cccgtcccct | cgaggaggt | gatcgacaag | 600 |
| atcaacgcca | aggggtctg | tcggtccacg | gccaagtacg | tgcgcaacaa | cctggagacc | 660 |
| accgcgtttc | accgggacga | ccacgagacc | gacatggagc | tgaaaccggc | caacgccgcg | 720 |
| accccgcacga | gccggggctg | gcacaccacc | gacctcaagt | acaacccctc | gcgggtggag | 780 |
| gcgttccacc | ggtacgggac | gacggtaaac | tgcatcgtcg | aggaggtgga | cgcgcgctcg | 840 |
| gtgtacccgt | acgacgagtt | tgtgttggcg | actggcgact | ttgtgtacat | gtccccgttt | 900 |
| tacggctacc | gggagggtc | gcacaccgaa | cacaccagct | acgccgccga | ccgcttcaag | 960 |
| caggtcgacg | gcttctacgc | gcgcgacctc | accaccaagg | cccgggccac | ggcgccgacc | 1020 |
| acccggaacc | tgctcacgac | ccccaagttc | accgtggcct | gggactgggt | gccaaagcgc | 1080 |
| ccgtcggtct | gcaccatgac | caagtggcag | gaggtggacg | agatgctgcg | ctccgagtac | 1140 |
| ggcggctcct | tccgattctc | ttccgacgcc | atatccacca | ccttcaccac | caacctgacc | 1200 |
| gagtacccgc | tctcgcgcgt | ggacctgggg | gactgcatcg | gcaaggacgc | ccgcgacgcc | 1260 |
| atggaccgca | tcttcgcccg | caggtacaac | gcgacgcaca | tcaaggtggg | ccagccgcag | 1320 |
| tactacctgg | ccaatggggg | ctttctgatc | gcgtaccagc | ccttctcag | aacacgctc | 1380 |
| gcggagctgt | acgtgcggga | acacctccgc | gagcagagcc | gcaagccccc | aaaccccacg | 1440 |
| cccccgccgc | cggggccag | cgccaacgcg | tccgtggagc | gcatcaagac | cacctcctcc | 1500 |
| atcgagttcg | ccaggctgca | gtttacgtac | aaccacatac | agcgccatgt | caacgatatg | 1560 |
| ttgggccgcg | ttgccatcgc | gtggtgcgag | ctgcagaatc | acgagctgac | cctgtggaac | 1620 |
| gaggcccgca | agctgaaccc | caacgccatc | gcctcggcca | ccgtgggccg | gcgggtgagc | 1680 |
| gcgcggatgc | tcggcgacgt | gatggccgtc | tccacgtgcg | tgccggtcgc | cgcggacaac | 1740 |
| gtgatcgtcc | aaaactcgat | gcgcatcagc | tcgcggcccg | gggcctgcta | cagccgcccc | 1800 |
| ctggtcagct | ttcggtacga | agaccagggc | ccgttggtcg | aggggcagct | ggggagaac | 1860 |

-continued

```
aacgagctgc ggctgacgcg cgatgcgatc gagccgtgca ccgtgggaca ccggcgctac    1920
ttcaccttcg gtgggggcta cgtgtacttc gaggagtacg cgtactccca ccagctgagc    1980
cgcgccgaca tcaccaccgt cagcaccttc atcgacctca acatcaccat gctggaggat    2040
cacgagtttg tccccctgga ggtgtacacc cgccacgaga tcaaggacag cggcctgctg    2100
gactacacgg aggtccagcg ccgcaaccag ctgcacgacc tgcgcttcgc cgacatcgac    2160
acggtcatcc acgccgacgc caacgccgcc atgtttgcgg gcctgggcgc gttcttcgag    2220
gggatgggcg aactggggcg cgcggtcggc aaggtggtga tgggcatcgt gggcggcgtg    2280
gtatcggccg tgtcgggcgt gtcctccttc atgtccaacc cctttggggc gctggccgtg    2340
ggtctgttgg tcctggccgg cctggcggcg gccttcttcg cctttcgcta cgtcatgcgg    2400
ctgcagagca accccatgaa ggccctgtac ccgctaacca ccaaggagct caagaacccc    2460
accaacccgg acgcgtccgg ggagggcgag gagggcggcg actttgacga ggccaagcta    2520
gccgaggccc gggagatgat acggtacatg gccctggtgt ctgccatgga gcgcacggaa    2580
cacaaggcca agaagaaggg cacgagcgcg ctgctcagcg ccaaggtcac cgacatggtc    2640
atgcgcaagc gccgcaacac caactacacc caagttccca acaaagacgg tgacgccgac    2700
gaggacgacc tgtga                                                    2715
```

<210> SEQ ID NO 12
<211> LENGTH: 904
<212> TYPE: PRT
<213> ORGANISM: Herpes simplex virus 1

<400> SEQUENCE: 12

```
Met Arg Gln Gly Ala Pro Ala Arg Gly Cys Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Ala Thr Gln Ala Ala Asn
        35                  40                  45

Gly Gly Pro Ala Thr Pro Ala Pro Pro Ala Leu Gly Ala Ala Pro Thr
    50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Ser Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220
```

```
Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
            245                 250                 255

Ser Arg Val Glu Ala Phe His Arg Tyr Gly Thr Thr Val Asn Cys Ile
        260                 265                 270

Val Glu Glu Val Asp Ala Arg Ser Val Tyr Pro Tyr Asp Glu Phe Val
    275                 280                 285

Leu Ala Thr Gly Asp Phe Val Tyr Met Ser Pro Phe Tyr Gly Tyr Arg
290                 295                 300

Glu Gly Ser His Thr Glu His Thr Ser Tyr Ala Ala Asp Arg Phe Lys
305                 310                 315                 320

Gln Val Asp Gly Phe Tyr Ala Arg Asp Leu Thr Thr Lys Ala Arg Ala
            325                 330                 335

Thr Ala Pro Thr Thr Arg Asn Leu Leu Thr Thr Pro Lys Phe Thr Val
        340                 345                 350

Ala Trp Asp Trp Val Pro Lys Arg Pro Ser Val Cys Thr Met Thr Lys
    355                 360                 365

Trp Gln Glu Val Asp Glu Met Leu Arg Ser Tyr Gly Gly Ser Phe
370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
            405                 410                 415

Ala Arg Asp Ala Met Asp Arg Ile Phe Ala Arg Arg Tyr Asn Ala Thr
        420                 425                 430

His Ile Lys Val Gly Gln Pro Gln Tyr Tyr Leu Ala Asn Gly Gly Phe
    435                 440                 445

Leu Ile Ala Tyr Gln Pro Leu Leu Ser Asn Thr Leu Ala Glu Leu Tyr
450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
            485                 490                 495

Thr Thr Ser Ser Ile Glu Phe Ala Arg Leu Gln Phe Thr Tyr Asn His
        500                 505                 510

Ile Gln Arg His Val Asn Asp Met Leu Gly Arg Val Ala Ile Ala Trp
    515                 520                 525

Cys Glu Leu Gln Asn His Glu Leu Thr Leu Trp Asn Glu Ala Arg Lys
530                 535                 540

Leu Asn Pro Asn Ala Ile Ala Ser Ala Thr Val Gly Arg Arg Val Ser
545                 550                 555                 560

Ala Arg Met Leu Gly Asp Val Met Ala Val Ser Thr Cys Val Pro Val
            565                 570                 575

Ala Ala Asp Asn Val Ile Val Gln Asn Ser Met Arg Ile Ser Ser Arg
        580                 585                 590

Pro Gly Ala Cys Tyr Ser Arg Pro Leu Val Ser Phe Arg Tyr Glu Asp
    595                 600                 605

Gln Gly Pro Leu Val Glu Gly Gln Leu Gly Glu Asn Asn Glu Leu Arg
610                 615                 620

Leu Thr Arg Asp Ala Ile Glu Pro Cys Thr Val Gly His Arg Arg Tyr
625                 630                 635                 640
```

```
Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
    690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
            740                 745                 750

Val Met Gly Ile Val Gly Gly Val Ser Ala Val Ser Gly Val Ser
        755                 760                 765

Ser Phe Met Ser Asn Pro Phe Gly Ala Leu Ala Val Gly Leu Leu Val
    770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu His Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
            900

<210> SEQ ID NO 13
<211> LENGTH: 2751
<212> TYPE: DNA
<213> ORGANISM: Herpes simplex virus 2

<400> SEQUENCE: 13
atgcgcgggg ggggcttgat ttgcgcgctg gtcgtggggg cgctggtggc cgcggtggcg      60
tcggcggccc cggcggcccc ggcggccccc cgcgcctcgg gcggcgtggc cgcgaccgtc     120
gcggcgaacg ggggtcccgc ctcccggccg cccccgtcc cgagcccgc gaccaccaag      180 gcccggaagc ggaaaaccaa aaagccgccc aagcggcccg aggcgacccc gcccccgac      240 gccaacgcga ccgtcgccgc cggccacgcc acgctgcgcg cgcacctgcg ggaaatcaag     300
gtcgagaacg ccgatgccca gttttacgtg tgcccgcccc cgacgggcgc cacggtggtg     360
cagtttgagc agccgcgccg ctgcccgacg cgcccggagg gcagaactca cgcgagggc     420 atcgcggtgg tcttcaagga gaacatcgcc ccgtacaaat caaggccac catgtactac     480 aaagacgtga ccgtgtcgca ggtgtggttc ggccaccgct actcccagtt tatgggata      540 ttcgaggacc gcgcccccgt tcccttcgag gaggtgatcg acaagattaa caccaagggg     600
```

-continued

| | |
|---|---|
| gtctgccgct ccacggccaa gtacgtgcgg aacaacatgg agaccaccgc gtttcaccgg | 660 |
| gacgaccacg agaccgacat ggagctcaag ccggcgaagg tcgccacgcg cacgagccgg | 720 |
| gggtggcaca ccaccgacct caagtacaac ccctcgcggg tggaggcgtt ccatcggtac | 780 |
| ggcacgacgg tcaactgcat cgtcgaggag gtggacgcgc ggtcggtgta cccgtacgat | 840 |
| gagtttgtgc tggcgacggg cgactttgtg tacatgtccc cgttttacgg ctaccgggag | 900 |
| gggtcgcaca ccgagcacac cagctacgcc gccgaccgct tcaagcaggt cgacggcttc | 960 |
| tacgcgcgcg acctcaccac gaaggcccgg gccacgtcgc cgacgacccg caacttgctg | 1020 |
| acgaccccca gtttaccgt ggcctgggac tgggtgccga agcgaccggc ggtctgcacc | 1080 |
| atgaccaagt ggcaggaggt ggacgagatg ctccgcgccg agtacggcgg ctccttccgc | 1140 |
| ttctcctccg acgccatctc gaccaccttc accaccaacc tgaccgagta ctcgctctcg | 1200 |
| cgcgtcgacc tgggcgactg catcggccgg gatgcccgcg aggccatcga ccgcatgttt | 1260 |
| gcgcgcaagt acaacgccac gcacatcaag gtgggccagc cgcagtacta cctggccacg | 1320 |
| gggggcttcc tcatcgcgta ccagcccctc ctcagcaaca cgctcgccga gctgtacgtg | 1380 |
| cgggagtaca tgcgggagca ggaccgcaag ccccggaatg ccacgcccgc gccactgcgg | 1440 |
| gaggcgccca gcgccaacgc gtccgtggag cgcatcaaga ccacctcctc gatcgagttc | 1500 |
| gcccggctgc agtttacgta taaccacata cagcgccacg tgaatgacat gctggggcgc | 1560 |
| atcgccgtcg cgtggtgcga gctgcagaac acgagctga ctctctggaa cgaggcccgc | 1620 |
| aagctcaacc ccaacgccat cgcctccgcc accgtcggcc ggcgggtgag cgcgcgcatg | 1680 |
| ctcggagacg tcatggccgt ctccacgtgc gtgcccgtcg ccccggacaa cgtgatcgtg | 1740 |
| cagaactcga tgcgcgtcag ctcgcggccg gggacgtgct acagccgccc cctggtcagc | 1800 |
| tttcggtacg aagaccaggg cccgctgatc gaggggcagc tgggcgagaa caacgagctg | 1860 |
| cgcctcaccc gcgacgcgct cgagccgtgc accgtgggcc accggcgcta cttcatcttc | 1920 |
| ggcgggggct acgtgtactt cgaggagtac gcgtactctc accagctgag tcgcgccgac | 1980 |
| gtcaccaccg tcagcacctt catcgacctg aacatcacca tgctggagga ccacgagttt | 2040 |
| gtgcccctgg aggtctacac gcgccacgag atcaaggaca gcggcctgct ggactacacg | 2100 |
| gaggtccagc gccgcaacca gctgcacgac ctgcgctttg ccgacatcga cacggtcatc | 2160 |
| cgcgccgacg ccaacgccgc catgttcgcg gggctgtgcg cgttcttcga ggggatgggg | 2220 |
| gacttggggc gcgcggtcgg caaggtagtc atgggagtag tggggggcgt ggtgtcggcc | 2280 |
| gtctcgggcg tgtcctcctt tatgtccaac cccttcgggg cgcttgccgt ggggctgctg | 2340 |
| gtcctggccg gctggtcgc ggccttcttc gccttccgct acgtcctgca actgcaacgc | 2400 |
| aatcccatga aggccctgta tccgctcacc accaaggaac tcaagacttc cgaccccggg | 2460 |
| ggcgtgggcg gggaggggga ggaaggcgcg gagggggcg ggtttgacga ggccaagttg | 2520 |
| gccgaggccc gagaaatgat ccgatatatg gctttggtgt cggccatgga gcgcacggaa | 2580 |
| cacaaggcca gaaagaaggg cacgagcgcc ctgctcagct ccaaggtcac caacatggtt | 2640 |
| ctgcgcaagc gcaacaaagc caggtactct ccgctccaca acgaggacga ggccggagac | 2700 |
| gaagacgagc tctaagggag gggaggggag ctgggcttgt gtataaataa a | 2751 |

<210> SEQ ID NO 14
<211> LENGTH: 904
<212> TYPE: PRT
<213> ORGANISM: Herpes simplex virus 2

<400> SEQUENCE: 14

-continued

```
Met Arg Gly Gly Gly Leu Ile Cys Ala Leu Val Val Gly Ala Leu Val
1               5                   10                  15
Ala Ala Val Ala Ser Ala Ala Pro Ala Ala Pro Ala Ala Pro Arg Ala
            20                  25                  30
Ser Gly Gly Val Ala Ala Thr Val Ala Ala Asn Gly Gly Pro Ala Ser
        35                  40                  45
Arg Pro Pro Pro Val Pro Ser Pro Ala Thr Thr Lys Ala Arg Lys Arg
    50                  55                  60
Lys Thr Lys Lys Pro Pro Lys Arg Pro Glu Ala Thr Pro Pro Pro Asp
65                  70                  75                  80
Ala Asn Ala Thr Val Ala Ala Gly His Ala Thr Leu Arg Ala His Leu
                85                  90                  95
Arg Glu Ile Lys Val Glu Asn Ala Asp Ala Gln Phe Tyr Val Cys Pro
            100                 105                 110
Pro Pro Thr Gly Ala Thr Val Val Gln Phe Glu Gln Pro Arg Arg Cys
        115                 120                 125
Pro Thr Arg Pro Glu Gly Gln Asn Tyr Thr Glu Gly Ile Ala Val Val
    130                 135                 140
Phe Lys Glu Asn Ile Ala Pro Tyr Lys Phe Lys Ala Thr Met Tyr Tyr
145                 150                 155                 160
Lys Asp Val Thr Val Ser Gln Val Trp Phe Gly His Arg Tyr Ser Gln
                165                 170                 175
Phe Met Gly Ile Phe Glu Asp Arg Ala Pro Val Pro Phe Glu Glu Val
            180                 185                 190
Ile Asp Lys Ile Asn Thr Lys Gly Val Cys Arg Ser Thr Ala Lys Tyr
        195                 200                 205
Val Arg Asn Asn Met Glu Thr Thr Ala Phe His Arg Asp Asp His Glu
    210                 215                 220
Thr Asp Met Glu Leu Lys Pro Ala Lys Val Ala Thr Arg Thr Ser Arg
225                 230                 235                 240
Gly Trp His Thr Thr Asp Leu Lys Tyr Asn Pro Ser Arg Val Glu Ala
                245                 250                 255
Phe His Arg Tyr Gly Thr Thr Val Asn Cys Ile Val Glu Glu Val Asp
            260                 265                 270
Ala Arg Ser Val Tyr Pro Tyr Asp Glu Phe Val Leu Ala Thr Gly Asp
        275                 280                 285
Phe Val Tyr Met Ser Pro Phe Tyr Gly Tyr Arg Glu Gly Ser His Thr
    290                 295                 300
Glu His Thr Ser Tyr Ala Ala Asp Arg Phe Lys Gln Val Asp Gly Phe
305                 310                 315                 320
Tyr Ala Arg Asp Leu Thr Thr Lys Ala Arg Ala Thr Ser Pro Thr Thr
                325                 330                 335
Arg Asn Leu Leu Thr Thr Pro Lys Phe Thr Val Ala Trp Asp Trp Val
            340                 345                 350
Pro Lys Arg Pro Ala Val Cys Thr Met Thr Lys Trp Gln Glu Val Asp
        355                 360                 365
Glu Met Leu Arg Ala Glu Tyr Gly Gly Ser Phe Arg Phe Ser Ser Asp
    370                 375                 380
Ala Ile Ser Thr Thr Phe Thr Thr Asn Leu Thr Glu Tyr Ser Leu Ser
385                 390                 395                 400
Arg Val Asp Leu Gly Asp Cys Ile Gly Arg Asp Ala Arg Glu Ala Ile
                405                 410                 415
```

```
Asp Arg Met Phe Ala Arg Lys Tyr Asn Ala Thr His Ile Lys Val Gly
            420                 425                 430

Gln Pro Gln Tyr Tyr Leu Ala Thr Gly Gly Phe Leu Ile Ala Tyr Gln
        435                 440                 445

Pro Leu Leu Ser Asn Thr Leu Ala Glu Leu Tyr Val Arg Glu Tyr Met
    450                 455                 460

Arg Glu Gln Asp Arg Lys Pro Arg Asn Ala Thr Pro Ala Pro Leu Arg
465                 470                 475                 480

Glu Ala Pro Ser Ala Asn Ala Ser Val Glu Arg Ile Lys Thr Thr Ser
                485                 490                 495

Ser Ile Glu Phe Ala Arg Leu Gln Phe Thr Tyr Asn His Ile Gln Arg
            500                 505                 510

His Val Asn Asp Met Leu Gly Arg Ile Ala Val Ala Trp Cys Glu Leu
        515                 520                 525

Gln Asn His Glu Leu Thr Leu Trp Asn Glu Ala Arg Lys Leu Asn Pro
    530                 535                 540

Asn Ala Ile Ala Ser Ala Thr Val Gly Arg Arg Val Ser Ala Arg Met
545                 550                 555                 560

Leu Gly Asp Val Met Ala Val Ser Thr Cys Val Pro Val Ala Pro Asp
                565                 570                 575

Asn Val Ile Val Gln Asn Ser Met Arg Val Ser Ser Arg Pro Gly Thr
            580                 585                 590

Cys Tyr Ser Arg Pro Leu Val Ser Phe Arg Tyr Glu Asp Gln Gly Pro
        595                 600                 605

Leu Ile Glu Gly Gln Leu Gly Glu Asn Asn Glu Leu Arg Leu Thr Arg
    610                 615                 620

Asp Ala Leu Glu Pro Cys Thr Val Gly His Arg Arg Tyr Phe Ile Phe
625                 630                 635                 640

Gly Gly Gly Tyr Val Tyr Phe Glu Glu Tyr Ala Tyr Ser His Gln Leu
                645                 650                 655

Ser Arg Ala Asp Val Thr Thr Val Ser Thr Phe Ile Asp Leu Asn Ile
            660                 665                 670

Thr Met Leu Glu Asp His Glu Phe Val Pro Leu Glu Val Tyr Thr Arg
        675                 680                 685

His Glu Ile Lys Asp Ser Gly Leu Leu Asp Tyr Thr Glu Val Gln Arg
    690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
                725                 730                 735

Glu Gly Met Gly Asp Leu Gly Arg Ala Val Gly Lys Val Val Met Gly
            740                 745                 750

Val Val Gly Gly Val Val Ser Ala Val Ser Gly Val Ser Ser Phe Met
        755                 760                 765

Ser Asn Pro Phe Gly Ala Leu Ala Val Gly Leu Leu Val Leu Ala Gly
    770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
                805                 810                 815

Ser Asp Pro Gly Gly Val Gly Gly Glu Gly Glu Glu Gly Ala Glu Gly
            820                 825                 830

Gly Gly Phe Asp Glu Ala Lys Leu Ala Glu Ala Arg Glu Met Ile Arg
```

```
                    835                 840                 845
Tyr Met Ala Leu Val Ser Ala Met Glu Arg Thr Glu His Lys Ala Arg
        850                 855                 860

Lys Lys Gly Thr Ser Ala Leu Leu Ser Ser Lys Val Thr Asn Met Val
865                 870                 875                 880

Leu Arg Lys Arg Asn Lys Ala Arg Tyr Ser Pro Leu His Asn Glu Asp
                885                 890                 895

Glu Ala Gly Asp Glu Asp Glu Leu
            900

<210> SEQ ID NO 15
<211> LENGTH: 2796
<212> TYPE: DNA
<213> ORGANISM: Varicella zoster virus

<400> SEQUENCE: 15
atgtcccctt gtggctatta ttcaaagtgg agaaacaggg atcgaccaga ataccgtcgt      60
aatctacgat tcagacgttt tttctcttct atacacccta atgcagcggc tggctccgga     120
ttcaacggac ccggcgtttt cataaccctc gttacggggg tgtggttatg cttttatgc      180 atattttcta tgtttgttac ggcggttgtg tcggtctctc caagctcgtt ttatgagagt     240
ttacaagtag agcccacaca atcagaagat ataacccggt ctgctcatct gggcgatggt     300
gatgaaatca gagaagctat acacaagtcc caggacgccg aaacaaaacc cacgttttac     360
gtctgcccac cgccaacagg ctccacaatc gtacgattag aaccaactcg gacatgtccg     420
gattatcacc ttggtaaaaa ctttacgagg gtattgctg ttgtttataa agaaaacatt      480
gcagcgtaca gtttaaggc gacggtatat tacaaagatg ttatcgttag cacggcgtgg     540
gccggaagtt cttatacgca aattactaat agatatgcgg ataggggtacc aattcccgtt     600 tcagagatca cggacaccat tgataagttt ggcaagtgtt cttctaaagc aacgtacgta     660
cgaaataacc acaaagttga agcctttaat gaggataaaa atccacagga tatgcctcta     720
atcgcatcaa aatataattc tgtgggatcc aaagcatggc atactaccaa tgacacgtac     780
atggttgccg aaccccccgg aacatatagg acgggcacgt cggtgaattg catcattgag     840
gaagttgaag ccagatcaat attcccttat gatagttttg actttccac gggagatata     900 atatacatgt ccccgttttt tggcctacgg gatggtgcat acagagaaca ttccaattat     960
gcaatggatc gttttcacca gtttgagggt tatagacaaa gggatcttga cactagagca    1020
ttactggaac ctgcagcgcg gaactttttta gtcacgcctc atttaacggt tggttggaac    1080
tggaagccaa acgaacgga agtttgttcg cttgtcaagt ggcgtgaggt tgaagacgta    1140
gttcgcgatg agtatgcaca caattttcgc tttacaatga aaacactttc taccacgttt    1200
ataagtgaaa caaacgagtt taatcttaac caaatccatc tcagtcaatg tgtaaaggag    1260
gaagcccggg ctattattaa ccggatctat acaaccagat acaactcatc tcatgttaga    1320
accggggata tccagaccta ccttgccaga gggggggttg ttgtggtgtt caacccctg     1380 ctgagcaatt ccctcgcccg tctctatctc caagaattgg tccgtgaaaa cactaatcat    1440
tcaccacaaa acacccgac tcgaaatacc agatcccgac gaagcgtgcc agttgagttg    1500
cgtgccaata gaacaataac aaccacctca tcggtggaat ttgctatgct ccagtttaca    1560
tatgaccaca ttcaagagca tgttaatgaa atgttggcac gtatctcctc gtcgtggtgc    1620
cagctacaaa atcgcgaacg cgccctttgg agcggactat ttccaattaa cccaagtgct    1680
ttagcgagca ccattttgga tcaacgtgtt aaagctcgta ttctcggcga cgttatctcc    1740
```

```
gtttctaatt gtccagaact gggatcagat acacgcatta tacttcaaaa ctctatgagg    1800
gtatctggta gtactacgcg ttgttatagc cgtcctttaa tttcaatagt tagtttaaat    1860
gggtccggga cggtggaggg ccagcttgga acagataacg agttaattat gtccagagat    1920
ctgttagaac catgcgtggc taatcacaag cgatattttc tatttgggca tcactacgta    1980
tattatgagg attatcgtta cgtccgtgaa atcgcagtcc atgatgtggg aatgattagc    2040
acttacgtag atttaaactt aacacttctt aaagatagag agtttatgcc gctgcaagta    2100
tatacaagag acgagctgcg ggatacagga ttactagact acagtgaaat caacgccga     2160 aatcaaatgc attcgctgcg ttttatgac atagacaagg ttgtgcaata tgatagcgga    2220
acggccatta tgcagggcat ggctcagttt ttccagggac ttgggaccgc gggccaggcc    2280
gttggacatg tggttcttgg ggccacggga gcgctgcttt ccaccgtaca cggatttacc    2340
acgtttttat ctaacccatt tggggcattg gccgtgggat tattggtttt ggcgggactg    2400
gtagcggcct ttttgcgta ccggtacgtg cttaaactta aaacaagccc gatgaaggca    2460
ttatatccac tcacaaccaa ggggttaaaa cagttaccgg aaggaatgga tccctttgcc    2520
gagaaaccca acgctactga taccccaata gaagaaattg gcgactcaca aaacactgaa    2580
ccgtcggtaa atagcgggtt tgatcccgat aaatttcgag aagcccagga aatgattaaa    2640
tatatgacgt tagtatctgc ggctgagcgc caagaatcta aagcccgcaa aaaaaataag    2700
actagcgccc ttttaacttc acgtcttacc ggccttgctt tacgaaatcg ccgaggatac    2760
tcccgtgttc gcaccgagaa tgtaacgggg gtgtaa                              2796
```

<210> SEQ ID NO 16
<211> LENGTH: 931
<212> TYPE: PRT
<213> ORGANISM: Varicella zoster virus

<400> SEQUENCE: 16

```
Met Ser Pro Cys Gly Tyr Tyr Ser Lys Trp Arg Asn Arg Asp Arg Pro
1               5                   10                  15

Glu Tyr Arg Arg Asn Leu Arg Phe Arg Arg Phe Phe Ser Ser Ile His
            20                  25                  30

Pro Asn Ala Ala Ala Gly Ser Gly Phe Asn Gly Pro Gly Val Phe Ile
        35                  40                  45

Thr Ser Val Thr Gly Val Trp Leu Cys Phe Leu Cys Ile Phe Ser Met
    50                  55                  60

Phe Val Thr Ala Val Val Ser Val Ser Pro Ser Ser Phe Tyr Glu Ser
65                  70                  75                  80

Leu Gln Val Glu Pro Thr Gln Ser Glu Asp Ile Thr Arg Ser Ala His
                85                  90                  95

Leu Gly Asp Gly Asp Glu Ile Arg Glu Ala Ile His Lys Ser Gln Asp
            100                 105                 110

Ala Glu Thr Lys Pro Thr Phe Tyr Val Cys Pro Pro Thr Gly Ser
        115                 120                 125

Thr Ile Val Arg Leu Glu Pro Thr Arg Thr Cys Pro Asp Tyr His Leu
    130                 135                 140

Gly Lys Asn Phe Thr Glu Gly Ile Ala Val Val Tyr Lys Glu Asn Ile
145                 150                 155                 160

Ala Ala Tyr Lys Phe Lys Ala Thr Val Tyr Tyr Lys Asp Val Ile Val
                165                 170                 175

Ser Thr Ala Trp Ala Gly Ser Ser Tyr Thr Gln Ile Thr Asn Arg Tyr
```

```
            180             185             190
Ala Asp Arg Val Pro Ile Pro Val Ser Glu Ile Thr Asp Thr Ile Asp
        195                 200                 205
Lys Phe Gly Lys Cys Ser Ser Lys Ala Thr Tyr Val Arg Asn Asn His
    210                 215                 220
Lys Val Glu Ala Phe Asn Glu Asp Lys Asn Pro Gln Asp Met Pro Leu
225                 230                 235                 240
Ile Ala Ser Lys Tyr Asn Ser Val Gly Ser Lys Ala Trp His Thr Thr
                245                 250                 255
Asn Asp Thr Tyr Met Val Ala Gly Thr Pro Gly Thr Tyr Arg Thr Gly
            260                 265                 270
Thr Ser Val Asn Cys Ile Ile Glu Glu Val Glu Ala Arg Ser Ile Phe
        275                 280                 285
Pro Tyr Asp Ser Phe Gly Leu Ser Thr Gly Asp Ile Ile Tyr Met Ser
    290                 295                 300
Pro Phe Phe Gly Leu Arg Asp Gly Ala Tyr Arg Glu His Ser Asn Tyr
305                 310                 315                 320
Ala Met Asp Arg Phe His Gln Phe Glu Gly Tyr Arg Gln Arg Asp Leu
                325                 330                 335
Asp Thr Arg Ala Leu Leu Glu Pro Ala Ala Arg Asn Phe Leu Val Thr
            340                 345                 350
Pro His Leu Thr Val Gly Trp Asn Trp Lys Pro Lys Arg Thr Glu Val
        355                 360                 365
Cys Ser Leu Val Lys Trp Arg Glu Val Glu Asp Val Val Arg Asp Glu
    370                 375                 380
Tyr Ala His Asn Phe Arg Phe Thr Met Lys Thr Leu Ser Thr Thr Phe
385                 390                 395                 400
Ile Ser Glu Thr Asn Glu Phe Asn Leu Asn Gln Ile His Leu Ser Gln
                405                 410                 415
Cys Val Lys Glu Glu Ala Arg Ala Ile Ile Asn Arg Ile Tyr Thr Thr
            420                 425                 430
Arg Tyr Asn Ser Ser His Val Arg Thr Gly Asp Ile Gln Thr Tyr Leu
        435                 440                 445
Ala Arg Gly Gly Phe Val Val Phe Gln Pro Leu Leu Ser Asn Ser
    450                 455                 460
Leu Ala Arg Leu Tyr Leu Gln Glu Leu Val Arg Glu Asn Thr Asn His
465                 470                 475                 480
Ser Pro Gln Lys His Pro Thr Arg Asn Thr Arg Ser Arg Arg Ser Val
                485                 490                 495
Pro Val Glu Leu Arg Ala Asn Arg Thr Ile Thr Thr Ser Ser Val
            500                 505                 510
Glu Phe Ala Met Leu Gln Phe Thr Tyr Asp His Ile Gln Glu His Val
        515                 520                 525
Asn Glu Met Leu Ala Arg Ile Ser Ser Ser Trp Cys Gln Leu Gln Asn
    530                 535                 540
Arg Glu Arg Ala Leu Trp Ser Gly Leu Phe Pro Ile Asn Pro Ser Ala
545                 550                 555                 560
Leu Ala Ser Thr Ile Leu Asp Gln Arg Val Lys Ala Arg Ile Leu Gly
                565                 570                 575
Asp Val Ile Ser Val Ser Asn Cys Pro Glu Leu Gly Ser Asp Thr Arg
            580                 585                 590
Ile Ile Leu Gln Asn Ser Met Arg Val Ser Gly Ser Thr Thr Arg Cys
        595                 600                 605
```

Tyr Ser Arg Pro Leu Ile Ser Ile Val Ser Leu Asn Gly Ser Gly Thr
        610                 615                 620

Val Glu Gly Gln Leu Gly Thr Asp Asn Glu Leu Ile Met Ser Arg Asp
625                 630                 635                 640

Leu Leu Glu Pro Cys Val Ala Asn His Lys Arg Tyr Phe Leu Phe Gly
                645                 650                 655

His His Tyr Val Tyr Tyr Glu Asp Tyr Arg Tyr Val Arg Glu Ile Ala
            660                 665                 670

Val His Asp Val Gly Met Ile Ser Thr Tyr Val Asp Leu Asn Leu Thr
    675                 680                 685

Leu Leu Lys Asp Arg Glu Phe Met Pro Leu Gln Val Tyr Thr Arg Asp
690                 695                 700

Glu Leu Arg Asp Thr Gly Leu Leu Asp Tyr Ser Glu Ile Gln Arg Arg
705                 710                 715                 720

Asn Gln Met His Ser Leu Arg Phe Tyr Asp Ile Asp Lys Val Val Gln
                725                 730                 735

Tyr Asp Ser Gly Thr Ala Ile Met Gln Gly Met Ala Gln Phe Phe Gln
            740                 745                 750

Gly Leu Gly Thr Ala Gly Gln Ala Val Gly His Val Val Leu Gly Ala
        755                 760                 765

Thr Gly Ala Leu Leu Ser Thr Val His Gly Phe Thr Thr Phe Leu Ser
770                 775                 780

Asn Pro Phe Gly Ala Leu Ala Val Gly Leu Leu Val Leu Ala Gly Leu
785                 790                 795                 800

Val Ala Ala Phe Phe Ala Tyr Arg Tyr Val Leu Lys Leu Lys Thr Ser
                805                 810                 815

Pro Met Lys Ala Leu Tyr Pro Leu Thr Thr Lys Gly Leu Lys Gln Leu
            820                 825                 830

Pro Glu Gly Met Asp Pro Phe Ala Glu Lys Pro Asn Ala Thr Asp Thr
        835                 840                 845

Pro Ile Glu Glu Ile Gly Asp Ser Gln Asn Thr Glu Pro Ser Val Asn
850                 855                 860

Ser Gly Phe Asp Pro Asp Lys Phe Arg Glu Ala Gln Glu Met Ile Lys
865                 870                 875                 880

Tyr Met Thr Leu Val Ser Ala Ala Glu Arg Gln Glu Ser Lys Ala Arg
                885                 890                 895

Lys Lys Asn Lys Thr Ser Ala Leu Leu Thr Ser Arg Leu Thr Gly Leu
            900                 905                 910

Ala Leu Arg Asn Arg Arg Gly Tyr Ser Arg Val Arg Thr Glu Asn Val
        915                 920                 925

Thr Gly Val
    930

<210> SEQ ID NO 17
<211> LENGTH: 2229
<212> TYPE: DNA
<213> ORGANISM: Human cytomegalovirus

<400> SEQUENCE: 17
atgcggccag gcctcccctc ctacctcatc atcctcgccg tctgtctctt cagccaccta      60
ctttcgtcac gatatggcgc agaagccgta tccgaaccgc tggacaaagc gtttcaccta     120
ctgctcaaca cctacgggag acccatccgc ttcctgcgtg aaaataccac ccagtgtacc     180
tacaacagca gcctccgtaa cagcacggtc gtcagggaaa acgccatcag tttcaacttt     240

```
ttccaaagct ataatcaata ctatgtattc catatgcctc gatgtctttt tgcgggtcct    300
ctggcggagc agtttctgaa ccaggtagat ctgaccgaaa ccctggaaag ataccaacag    360
agacttaaca cttacgcgct ggtatccaaa gacctggcca gctaccgatc tttttcgcag    420
cagctaaagg cacaagacag cctaggtgaa cagcccacca ctgtgccacc gcccattgac    480
ctgtcaatac ctcacgtttg gatgccaccg caaaccactc cacacggctg acagaatca    540 cataccacct caggactaca ccgaccacac tttaaccaga cctgtatcct ctttgatgga    600
cacgatctac tattcagcac cgtcacacct tgtttgcacc aaggctttta cctcatcgac    660
gaactacgtt acgttaaaat aacactgacc gaggacttct tcgtagttac ggtgtccata    720
gacgacgaca cacccatgct gcttatcttc ggccatcttc cacgcgtact tttcaaagcg    780
ccctatcaac gcgacaactt tatactacga caaactgaaa acacgagct cctggtgcta    840 gttaagaaag atcaactgaa ccgtcactct tatctcaaag acccggactt tcttgacgcc    900
gcacttgact caactacct agacctcagc gcactactac gtaacagctt tcaccgttac    960
gccgtggatg tactcaagag cggtcgatgt cagatgctgg accgccgcac ggtagaaatg   1020
gccttcgcct acgcattagc actgttcgca gcagcccgac aagaagaggc cggcgcccaa   1080
gtctccgtcc cacgggccct agaccgccag ccgcactct tacaaataca agaatttatg   1140
atcacctgcc tctcacaaac accaccacgc accacgttgc tgctgtatcc cacggccgtg   1200
gacctggcca acgagccct tggacaccg aatcagatca ccgacatcac cagcctcgta   1260
cgcctggtct acatactctc taaacagaat cagcaacatc tcatccccca atgggcacta   1320
cgacagatcg ccgactttgc cctaaaacta cacaaaacgc acctggcctc ttttctttca   1380
gccttcgcac gccaagaact ctacctcatg ggcagcctcg tccactccat gctggtacat   1440
acgacggaga gacgcgaaat cttcatcgta gaaacgggcc tctgttcatt ggccgagcta   1500
tcacacttta cgcagttgtt agctcatcca caccacgaat acctcagcga cctgtacaca   1560
ccctgttcca gtagcgggcg acgcgatcac tcgctcgaac gcctcacgcg tctcttcccc   1620
gatgccaccg tccccgctac cgttcccgcc gccctctcca tcctatctac catgcaacca   1680
agcacgctgg aaaccttccc cgacctgttt tgcttgccgc tcggcgaatc cttctccgcg   1740
ctgaccgtct ccgaacacgt cagttatatc gtaacaaacc agtacctgat caaaggtatc   1800
tcctaccctg tctccaccac cgtcgtaggc cagagcctca tcatcaccca gacggacagt   1860
caaactaaat gcgaactgac gcgcaacatg cataccacac acagcatcac agtggcgctc   1920
aacatttcgc tagaaaactg cgccttttgc caaagcgccc tgctagaata cgacgacacg   1980
caaggcgtca tcaacatcat gtacatgcac gactcggacg acgtccttttc cgccctggat   2040 ccctacaacg aagtggtggt ctcatctccg cgaactcact acctcatgct tttgaaaaac   2100
ggtacggtac tagaagtaac tgacgtcgtc gtggacgcca ccgacagtcg tctcctcatg   2160
atgtccgtct acgcgctatc ggccatcatc ggcatctatc tgctctaccg catgctcaag   2220
acatgctga                                                           2229
```

<210> SEQ ID NO 18
<211> LENGTH: 742
<212> TYPE: PRT
<213> ORGANISM: Human cytomegalovirus

<400> SEQUENCE: 18

```
Met Arg Pro Gly Leu Pro Ser Tyr Leu Ile Val Leu Ala Val Cys Leu
1               5                   10                  15
```

```
Leu Ser His Leu Leu Ser Ser Arg Tyr Gly Ala Glu Ala Ile Ser Glu
             20                  25                  30

Pro Leu Asp Lys Ala Phe His Leu Leu Asn Thr Tyr Gly Arg Pro
         35                  40                  45

Ile Arg Phe Leu Arg Glu Asn Thr Thr Gln Cys Thr Tyr Asn Ser Ser
 50                  55                  60

Leu Arg Asn Ser Thr Val Val Arg Glu Asn Ala Ile Ser Phe Asn Phe
 65                  70                  75                  80

Phe Gln Ser Tyr Asn Gln Tyr Val Phe His Met Pro Arg Cys Leu
                 85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
130                 135                 140

Gln Asp Ser Leu Gly Glu Gln Pro Thr Thr Val Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
            195                 200                 205

Thr Pro Cys Leu His Gln Gly Phe Tyr Leu Ile Asp Glu Leu Arg Tyr
        210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430
```

```
His Leu Ile Pro Gln Trp Ala Leu Arg Gln Ile Ala Asp Phe Ala Leu
            435                 440                 445

Lys Leu His Lys Thr His Leu Ala Ser Phe Leu Ser Ala Phe Ala Arg
450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740

<210> SEQ ID NO 19
<211> LENGTH: 5
<212> TYPE: PRT
<213> ORGANISM: Human cytomegalovirus

<400> SEQUENCE: 19

Arg Thr Lys Arg Ser
1               5

<210> SEQ ID NO 20
<211> LENGTH: 5
<212> TYPE: PRT
<213> ORGANISM: Epstein-Barr virus

<400> SEQUENCE: 20
```

Arg Arg Arg Arg Asp
1               5

<210> SEQ ID NO 21
<211> LENGTH: 2229
<212> TYPE: DNA
<213> ORGANISM: Human herpesvirus

<400> SEQUENCE: 21

| | | | | | |
|---|---|---|---|---|---:|
| tcagcatgtc | ttgagcatgc | ggtagagcag | atagatgccg | atgatggccg | atagcgcgta | 60 |
| gacggacatc | atgaggagac | gactgtcggt | ggcgtccacg | acgacgtcag | ttacttctag | 120 |
| taccgtaccg | tttttcaaaa | gcatgaggta | gtgagttcgc | ggagatgaga | ccaccacttc | 180 |
| gttgtaggga | tccagggcga | aaaggacgtc | gtccgagtcg | tgcatgtaca | tgatgttgat | 240 |
| gacgccttgc | gtgtcgtcgt | attctagcag | ggcgctttgg | caaaaggcgc | agttttctag | 300 |
| cgaaatgttg | agcgccactg | tgatgctgtg | tgtggtatgc | atgttgcgcg | tcagttcgca | 360 |
| tttagtttga | ctgtccgtct | gggtgatgat | gaggctctgg | cctacgacgg | tggtggagac | 420 |
| agggtaggag | atacctttga | tcaggtactg | gtttgttacg | atataactga | cgtgttcgga | 480 |
| gacggtcagc | gcggagaagg | attcgccgag | cggcaagcaa | acaggtcgg | ggaaggtttc | 540 |
| cagcgtgctt | ggttgcatgg | tagataggat | ggagagggcg | gcgggaacgg | tagcggggac | 600 |
| ggtggcatcg | gggaagagac | gcgtgaggcg | ttcgagcgag | tgatcgcgtc | gcccgctact | 660 |
| ggaacagggt | gtgtacaggt | cgctgaggta | ttcgtggtgt | ggatgagcta | acaactgcgt | 720 |
| aaagtgtgat | agctcggcca | atgaacagag | gcccgtttct | acgatgaaga | tttcgcgtct | 780 |
| ctccgtcgta | tgtaccagca | tggagtggac | gaggctgccc | atgaggtaga | gttcttggcg | 840 |
| tgcgaaggct | gaaagaaaag | aggccaggtg | cgttttgtgt | agtttaggg | caaagtcggc | 900 |
| gatctgtcgt | agtgcccatt | ggggatgag | atgttgctga | ttctgtttag | agagtatgta | 960 |
| gaccaggcg | acgaggctgg | tgatgtcggt | gatctgattc | ggtgtccaaa | gggctcgttt | 1020 |
| ggccaggtcc | acggccgtgg | gatacagcag | caacgtggtg | cgtggtggtg | tttgtgagag | 1080 |
| gcaggtgatc | ataaattctt | gtatttgtaa | gagtgcggcc | tggcggtcta | gggcccgtgg | 1140 |
| gacggagact | tgggcgccgg | cctcttcttg | tcgggctgct | gcgaacagtg | ctaatgcgta | 1200 |
| ggcgaaggcc | atttctaccg | tgcggcggtc | cagcatctga | catcgaccgc | tcttgagtac | 1260 |
| atccacggcg | taacggtgaa | agctgttacg | tagtagtgcg | ctgaggtcta | ggtagttgaa | 1320 |
| gtcaagtgcg | gcgtcaagaa | agtccgggtc | tttgagataa | gagtgacggt | tcagttgatc | 1380 |
| tttcttaact | agcaccagga | gctcgtgttt | ttcagttttgt | cgtagtataa | agttgtcgcg | 1440 |
| ttgatagggc | gctttgaaaa | gtacgcgtgg | aagatggccg | aagataagca | gcatgggtgt | 1500 |
| gtcgtcgtct | atggacaccg | taactacgaa | gaagtcctcg | gtcagtgtta | ttttaacgta | 1560 |
| acgtagttcg | tcgatgaggt | aaaagccttg | gtgcaaacaa | ggtgtgacgg | tgctgaatag | 1620 |
| tagatcgtgt | ccatcaaaga | ggatacaggt | ctggttaaag | tgtggtcggt | gtagtcctga | 1680 |
| ggtggtatgt | gattctgtcc | agccgtgtgg | agtggtttgc | ggtggcatcc | aaacgtgagg | 1740 |
| tattgacagg | tcaatgggcg | gtggcacagt | ggtgggctgt | tcacctaggc | tgtcttgtgc | 1800 |
| ctttagctgc | tgcgaaaaag | atcggtagct | ggccaggtct | ttggatacca | gcgcgtaagt | 1860 |
| gttaagtctc | tgttggtatc | tttccagggt | ttcggtcaga | tctacctggt | tcagaaactg | 1920 |
| ctccgccaga | ggacccgcaa | aaagacatcg | aggcatatgg | aatacatagt | attgattata | 1980 |
| gctttggaaa | aagttgaaac | tgatggcgtt | ttccctgacg | accgtgctgt | tacggaggct | 2040 |

```
gctgttgtag gtacactggg tggtattttc acgcaggaag cggatgggtc tcccgtaggt    2100
gttgagcagt aggtgaaacg ctttgtccag cggttcggat acggcttctg cgccatatcg    2160
tgacgaaagt aggtggctga agagacagac ggcgaggatg atgaggtagg aggggaggcc    2220
tggccgcat                                                            2229

<210> SEQ ID NO 22
<211> LENGTH: 837
<212> TYPE: DNA
<213> ORGANISM: Human herpesvirus

<400> SEQUENCE: 22
ttagcgagca tccactgctt gagggccata gcgcgagtga gccggcaggt tgacgcgcgt      60
ctgcttcagc tcgggcggca gtccggcgta gtatttatct aggtggcgta gcagcggcgg     120
gtccagctgg tgacgcaggc agaattcctt cactgcgttg tacaggccgt aaaagagcgt     180
gatgccctcg ggcgcggcag cggtgctcac gggcagacgc acggcgcggt tggtacgcgt     240
ggcttcgttg cgtatggcca ccaccacgtt aaagagagac ggtggcacca gctcgaagcc     300
taacacgtgt tccgtgaaga tgctgcgccc gtatgacagt cgccgtgaggt cgtagccgcg     360 gcacaggtcg tccacgcacg tgtacacggc cggcgagcca tcgccgcact cgctgtagcc     420
gcgcatcacc gtcatccagc gcggcgctgt gtccgagctc aacagcgtca gcagggcccg     480
caattgatcc ggattgttgt acagcagggc cagagtgtcc aggaaagcct cgtccaacag     540
cacggagttg gcggcctccg gcgtaacggg acggtaacgg ataagttgcg atagcgggcc     600
atcgcgcccg gtaacattca ccaacgggcg cagccaactt tcatacttgt caccctcaaa     660
cacctcaccc aacaagcatc ggcgcgttag ttcggggcac tccgcgggga ctttctcggc     720
ggcggtagga gcgacgctga cggcggctga ggaaacaatg ggcagcagaa ggcaacacca     780
cagcagtatc accggtccag gtgagaaaga gaagccgcaa tccgggcggc ggcacat       837

<210> SEQ ID NO 23
<211> LENGTH: 837
<212> TYPE: DNA
<213> ORGANISM: Human cytomegalovirus

<400> SEQUENCE: 23
atgtgccgcc gcccggattg cggcttctct ttctcacctg gaccggtgat actgctgtgg      60
tgttgccttc tgctgcccat tgtttcctca gccgccgtca gcgtcgctcc taccgccgcc     120
gagaaagtcc ccgcggagtg ccccgaacta acgcgccgat gcttgttggg tgaggtgttt     180
gagggtgaca agtatgaaag ttggctgcgc ccgttggtga atgttaccgg gcgcgatggc     240
ccgctatcgc aacttatccg ttaccgtccc gttacgccgg aggccgccaa ctccgtgctg     300
ttggacgagg ctttcctgga cactctggcc ctgctgtaca caatccgga tcaattgcgg     360 gccctgctga cgctgttgag ctcggacaca gcgccgcgct ggatgacggt gatgcgcggc     420
tacagcgagt gcggcgatgg ctcgccggcc gtgtacacgt gcgtggacga cctgtgccgc     480
ggctacgacc tcacgcgact gtcatacggg cgcagcatct tcacggaaca cgtgttaggc     540
ttcgagctgg tgccaccgtc tctctttaac gtggtggtgg ccatacgcaa cgaagccacg     600
cgtaccaacc gcgccgtgcg tctgcccgtg agcaccgctg ccgcgcccga gggcatcacg     660
ctcttttacg gcctgtacaa cgcagtgaag gaattctgcc tcgtcaccca gctggacccg     720
ccgctgctac gccacctaga taaatactac gccggactgc cgcccgagct gaagcagacg     780
cgcgtcaacc tgccggctca ctcgcgctat ggccctcaag cagtggatgc tcgctaa       837
```

<210> SEQ ID NO 24
<211> LENGTH: 278
<212> TYPE: PRT
<213> ORGANISM: Human cytomegalovirus

<400> SEQUENCE: 24

Met Cys Arg Arg Pro Asp Cys Gly Phe Ser Phe Ser Pro Gly Pro Val
1               5                   10                  15

Ala Leu Leu Trp Cys Cys Leu Leu Pro Ile Val Ser Ser Ala Thr
            20                  25                  30

Val Ser Val Ala Pro Thr Val Ala Glu Lys Val Pro Ala Glu Cys Pro
        35                  40                  45

Glu Leu Thr Arg Arg Cys Leu Leu Gly Glu Val Phe Gln Gly Asp Lys
    50                  55                  60

Tyr Glu Ser Trp Leu Arg Pro Leu Val Asn Val Thr Arg Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 25
<211> LENGTH: 984
<212> TYPE: PRT
<213> ORGANISM: Human cytomegalovirus

<400> SEQUENCE: 25

Met Glu Thr Asp Thr Leu Leu Leu Trp Val Leu Leu Leu Trp Val Pro
1               5                   10                  15

Gly Ser Thr Gly Asp Ala Thr Val Ser Val Ala Pro Thr Val Ala Glu
            20                  25                  30

Lys Val Pro Ala Glu Cys Pro Glu Leu Thr Arg Arg Cys Leu Leu Gly
        35                  40                  45

```
Glu Val Phe Gln Gly Asp Lys Tyr Glu Ser Trp Leu Arg Pro Leu Val
 50                  55                  60

Asn Val Thr Arg Arg Asp Gly Pro Leu Ser Gln Leu Ile Arg Tyr Arg
 65                  70                  75                  80

Pro Val Thr Pro Glu Ala Ala Asn Ser Val Leu Leu Asp Asp Ala Phe
                 85                  90                  95

Leu Asp Thr Leu Ala Leu Leu Tyr Asn Asn Pro Asp Gln Leu Arg Ala
                100                 105                 110

Leu Leu Thr Leu Leu Ser Ser Asp Thr Ala Pro Arg Trp Met Thr Val
            115                 120                 125

Met Arg Gly Tyr Ser Glu Cys Gly Asp Gly Ser Pro Ala Val Tyr Thr
130                 135                 140

Cys Val Asp Asp Leu Cys Arg Gly Tyr Asp Leu Thr Arg Leu Ser Tyr
145                 150                 155                 160

Gly Arg Ser Ile Phe Thr Glu His Val Leu Gly Phe Glu Leu Val Pro
                165                 170                 175

Pro Ser Leu Phe Asn Val Val Ala Ile Arg Asn Glu Ala Thr Arg
                180                 185                 190

Thr Asn Arg Ala Val Arg Leu Pro Val Ser Thr Ala Ala Pro Glu
            195                 200                 205

Gly Ile Thr Leu Phe Tyr Gly Leu Tyr Asn Ala Val Lys Glu Phe Cys
210                 215                 220

Leu Arg His Gln Leu Asp Pro Pro Leu Leu Arg His Leu Asp Lys Tyr
225                 230                 235                 240

Tyr Ala Gly Leu Pro Pro Glu Leu Lys Gln Thr Arg Val Asn Leu Pro
                245                 250                 255

Ala His Ser Arg Tyr Gly Pro Gln Ala Val Asp Ala Arg Gly Gly Gly
            260                 265                 270

Gly Ser Gly Gly Gly Ser Gly Gly Gly Ser Tyr Gly Ala Glu
        275                 280                 285

Ala Ile Ser Glu Pro Leu Asp Lys Ala Phe His Leu Leu Asn Thr
290                 295                 300

Tyr Gly Arg Pro Ile Arg Phe Leu Arg Glu Asn Thr Thr Gln Cys Thr
305                 310                 315                 320

Tyr Asn Ser Ser Leu Arg Asn Ser Thr Val Val Arg Glu Asn Ala Ile
                325                 330                 335

Ser Phe Asn Phe Phe Gln Ser Tyr Asn Gln Tyr Val Phe His Met
            340                 345                 350

Pro Arg Cys Leu Phe Ala Gly Pro Leu Ala Glu Gln Phe Leu Asn Gln
        355                 360                 365

Val Asp Leu Thr Glu Thr Leu Glu Arg Tyr Gln Gln Arg Leu Asn Thr
        370                 375                 380

Tyr Ala Leu Val Ser Lys Asp Leu Ala Ser Tyr Arg Ser Phe Ser Gln
385                 390                 395                 400

Gln Leu Lys Ala Gln Asp Ser Leu Gly Glu Gln Pro Thr Thr Val Pro
                405                 410                 415

Pro Pro Ile Asp Leu Ser Ile Pro His Val Trp Met Pro Pro Gln Thr
            420                 425                 430

Thr Pro His Gly Trp Thr Glu Ser His Thr Thr Ser Gly Leu His Arg
        435                 440                 445

Pro His Phe Asn Gln Thr Cys Ile Leu Phe Asp Gly His Asp Leu Leu
    450                 455                 460
```

-continued

Phe Ser Thr Val Thr Pro Cys Leu His Gln Gly Phe Tyr Leu Ile Asp
465                 470                 475                 480

Glu Leu Arg Tyr Val Lys Ile Thr Leu Thr Glu Asp Phe Phe Val Val
            485                 490                 495

Thr Val Ser Ile Asp Asp Thr Pro Met Leu Leu Ile Phe Gly His
            500                 505                 510

Leu Pro Arg Val Leu Phe Lys Ala Pro Tyr Gln Arg Asp Asn Phe Ile
            515                 520                 525

Leu Arg Gln Thr Glu Lys His Glu Leu Leu Val Leu Val Lys Lys Asp
            530                 535                 540

Gln Leu Asn Arg His Ser Tyr Leu Lys Asp Pro Asp Phe Leu Asp Ala
545                 550                 555                 560

Ala Leu Asp Phe Asn Tyr Leu Asp Leu Ser Ala Leu Leu Arg Asn Ser
                565                 570                 575

Phe His Arg Tyr Ala Val Asp Val Leu Lys Ser Gly Arg Cys Gln Met
                580                 585                 590

Leu Asp Arg Arg Thr Val Glu Met Ala Phe Ala Tyr Ala Leu Ala Leu
            595                 600                 605

Phe Ala Ala Ala Arg Gln Glu Glu Ala Gly Ala Gln Val Ser Val Pro
610                 615                 620

Arg Ala Leu Asp Arg Gln Ala Ala Leu Leu Gln Ile Gln Glu Phe Met
625                 630                 635                 640

Ile Thr Cys Leu Ser Gln Thr Pro Pro Arg Thr Leu Leu Leu Tyr
                645                 650                 655

Pro Thr Ala Val Asp Leu Ala Lys Arg Ala Leu Trp Thr Pro Asn Gln
                660                 665                 670

Ile Thr Asp Ile Thr Ser Leu Val Arg Leu Val Tyr Ile Leu Ser Lys
                675                 680                 685

Gln Asn Gln Gln His Leu Ile Pro Gln Trp Ala Leu Arg Gln Ile Ala
            690                 695                 700

Asp Phe Ala Leu Lys Leu His Lys Thr His Leu Ala Ser Phe Leu Ser
705                 710                 715                 720

Ala Phe Ala Arg Gln Glu Leu Tyr Leu Met Gly Ser Leu Val His Ser
                725                 730                 735

Met Leu Val His Thr Glu Arg Arg Glu Ile Phe Ile Val Glu Thr
                740                 745                 750

Gly Leu Cys Ser Leu Ala Glu Leu Ser His Phe Thr Gln Leu Leu Ala
            755                 760                 765

His Pro His His Glu Tyr Leu Ser Asp Leu Tyr Thr Pro Cys Ser Ser
770                 775                 780

Ser Gly Arg Arg Asp His Ser Leu Glu Arg Leu Thr Arg Leu Phe Pro
785                 790                 795                 800

Asp Ala Thr Val Pro Thr Thr Val Pro Ala Ala Leu Ser Ile Leu Ser
                805                 810                 815

Thr Met Gln Pro Ser Thr Leu Glu Thr Phe Pro Asp Leu Phe Cys Leu
                820                 825                 830

Pro Leu Gly Glu Ser Phe Ser Ala Leu Thr Val Ser Glu His Val Ser
            835                 840                 845

Tyr Val Val Thr Asn Gln Tyr Leu Ile Lys Gly Ile Ser Tyr Pro Val
            850                 855                 860

Ser Thr Thr Val Val Gly Gln Ser Leu Ile Ile Thr Gln Thr Asp Ser
865                 870                 875                 880

Gln Thr Lys Cys Glu Leu Thr Arg Asn Met His Thr Thr His Ser Ile

-continued

```
                    885                 890                 895
Thr Ala Ala Leu Asn Ile Ser Leu Glu Asn Cys Ala Phe Cys Gln Ser
                900                 905                 910

Ala Leu Leu Glu Tyr Asp Asp Thr Gln Gly Val Ile Asn Ile Met Tyr
                915                 920                 925

Met His Asp Ser Asp Asp Val Leu Phe Ala Leu Asp Pro Tyr Asn Glu
            930                 935                 940

Val Val Val Ser Ser Pro Arg Thr His Tyr Leu Met Leu Leu Lys Asn
945                 950                 955                 960

Gly Thr Val Leu Glu Val Thr Asp Val Val Val Asp Ala Thr Asp Ser
                965                 970                 975

Arg Leu His His His His His His
            980

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5
```

HUMAN HERPESVIRUS TRIMERIC GLYCOPROTEIN B, PROTEIN COMPLEXES COMPRISING TRIMERIC GB AND THEIR USE AS VACCINES

CROSS-REFERENCE TO RELATED APPLICATIONS

This application is a U.S. National Stage application of PCT/US2014/069856 filed 11 Dec. 2014, which claims the benefit of, and relies on the filing date of, U.S. provisional patent application No. 61/914,903, filed 11 Dec. 2013, the entire disclosure of which is incorporated herein by reference.

GOVERNMENT INTEREST

This invention was made with government support under USU Dean's Research and Education Endowment awarded by the Uniformed Services University. The government has certain rights in this invention.

SEQUENCE LISTING

The instant application contains a Sequence Listing which has been submitted electronically in ASCII format and is hereby incorporated by reference in its entirety. Said ASCII copy, created on Dec. 11, 2014, is named HMJ-143-PCT_SL.txt and is 103,345 bytes in size.

BACKGROUND

Human cytomegalovirus (HCMV) is a ubiquitously occurring pathogen that causes severe disease in immunocompromised hosts. HCMV is the most common viral infection acquired in utero in the developed world, and is a major cause of congenital defects in newborns. In the U.S. and Europe an estimated 0.2% to 1.2% of all live born infants are infected with HCMV. Congenital HCMV infection is a leading cause of sensorineural hearing loss in children and is the leading infectious cause of central nervous system damage in children.

In addition to newborn infants, the virus can also cause severe disease in immunosuppressed patients, such as organ transplant recipients and HIV-positive individuals. HCMV can become an opportunistic pathogen in these patients and cause severe disease with high morbidity and mortality.

HCMV is an enveloped, double-stranded DNA j-herpesvirus of the Herpesviridae family. Glycoprotein B (gB) of the Herpesviridae family is a type III fusion protein that has a shared trimeric structure of its fusion-active forms, and a post-fusion trimer of hairpins. HCMV gB is encoded by the UL55 gene and is synthesized as a 906-amino acid precursor molecule in infected cells. An amino-terminal signal sequence directs the nascent polypeptide to the endoplasmic reticulum (ER), where gB folds and rapidly associates into disulfide-dependent macromolecular complexes formed by identical molecules. Following transport from the ER, HCMV gB enters the Golgi apparatus, where it underdoes glycosylation and is processed by proteolysis by the host subtilisin-like enzyme, furin, into the amino-terminal and carboxy-terminal fragments, gp115 and gp55, respectively. These two fragments of the monomeric form of gB—gp 115 and gp55—are held together by intramolecular disulfide bonds. The mature product is then delivered to the surface of infected cells, where it is recycled between endosomal vesicles and the plasma membrane and is eventually incorporated into virions. Recently, native HCMV gB has been postulated to be a homotrimer based on the 3D crystallography structure of gB proteins in related viruses, Herpes Simplex Virus I (HSV-1) gB and Epstein Barr Virus (EBV) gB, which are homotrimers (29-32). Various vaccines, including live attenuated vaccines and subunit vaccines, are being developed to target HCMV-associated diseases. For example, gB is considered a major vaccine target antigen for eliciting neutralizing antibodies based on its critical role in mediating viral-host cell fusion and thus viral entry. Indeed a significant portion of neutralizing antibodies in human serum is specific for gB epitopes. Others have attempted to take advantage of this humoral response to gB in the effort to develop an effective vaccine for the prevention of HCMV infection. For example, a recombinant gB protein is described in Spaete et al., *A recombinant subunit vaccine approach to HCMV vaccine development*, Transplantation Proceedings, Vol 23, No 3, Suppl 3 (June), 1991: pp 90-96, and in WO 2012/049317, which is hereby incorporated by reference in its entirety. Based on analysis of a gB protein made in an analogous manner, it is believed that this recombinant gB protein is composed of mostly dimeric gB and minor amounts of monomeric and trimeric gB. This recombinant gB protein was generated by mutating the gene encoding for gB at the furin cleavage site, rendering the site ineffectual, and deleting the transmembrane domain, thus leaving the extracellular and intracellular domains.

A vaccine based on this recombinant gB protein was used in Phase 2 clinical trials. Pass et al., *Vaccine Prevention of Maternal Cytomegalovirus Infection*, N Engl J Med 2009; 360:1191-1199. Three doses of the HCMV vaccine or placebo were given at 0, 1, and 6 months to HCMV-seronegative women within 1 year after they had given birth. HCMV infection was determined in the women in quarterly tests during a 42-month period, using an assay for IgG antibodies against HCMV proteins other than glycoprotein B. Infection was confirmed by virus culture or immunoblotting. The primary end point was the time until the detection of HCMV infection. 234 subjects were randomly assigned to receive the HCMV vaccine and 230 subjects to receive placebo. After a minimum of 1 year of follow-up, there were 49 confirmed infections, 18 in the vaccine group and 31 in the placebo group. Kaplan-Meier analysis showed that the vaccine group was more likely to remain uninfected during a 42-month period than the placebo group (P=0.02). Vaccine efficacy was 50% (95% confidence interval, 7 to 73) on the basis of infection rates per 100 person-years. One congenital infection among infants of the subjects occurred in the vaccine group, and three infections occurred in the placebo group.

However, no vaccine candidates for the prevention of HCMV have entered into Phase III clinical trials. Although the natural conformation of gB during HCMV infections is predicted to be a trimer, there has been no reported success in producing a recombinant trimeric gB.

Likewise, Epstein-Barr Virus (EBV), also known as human herpesvirus 4, is a major, global source of morbidity and mortality, responsible for such pathologic entities as Burkitt lymphoma, nasopharyngeal carcinoma, infectious mononucleosis, a subset of Hodgkin's disease, and the lymphoproliferative syndrome in immunosuppressed patients. EBV is a γ-herpesvirus, with a double stranded, linear DNA genome, that infects B cells and epithelial cells. Vaccines being developed to target EBV infection have focused on glycoprotein 350 (gp350) (E. M. Sokal et al., *J. Infect. Di.* 196: 1749 (2007)); however, no vaccine candidates for the prevention of EBV have targeted EBV gB, whose natural conformation during EBV infection has been shown to be a trimer. (Backovic M, Longnecker R, Jardetzky T S. 2009. Structure of a trimeric variant of the Epstein-Barr virus glycoprotein B. *Proc Natl Acad Sci USA* 106: 2880-5.)

SUMMARY

The present disclosure provides new and improved strategies for enhancing an immune response to herpesvirus infection. These improved strategies involve creating a modified herpesvirus gB by inserting a peptide linker at the furin cleavage site in the herpesvirus gB polypeptide extracellular domain. Inserting the peptide linker removes the furin recognition sequence, such that expression of the modified herpesvirus gB results in the production of a homotrimeric gB complex that provides enhanced immunogenicity. Without intending to be bound by any theory, it is believed that such a linker sequence can allow the modified herpesvirus gB polypeptide to undergo native conformational folding and form a homotrimer.

Another aspect is a recombinant nucleic acid encoding the modified herpesvirus gB polypeptide, and a method of using the recombinant nucleic acid to express the modified herpesvirus gB polypeptide in a cell. Yet another aspect is directed to a method of inducing an immune response in a subject by administering to the subject a vaccine composition comprising the modified herpesvirus gB polypeptide or a nucleic acid encoding the same, where the herpesvirus gB polypeptide induces an immune response in the subject. The vaccine composition can optionally include other herpesvirus antigens, including but not limited to one or more of glycoprotein H (gH), glycoprotein L (gL), glycoprotein 350 (gp350), UL128, UL130, UL131, or combinations thereof.

Another aspect is directed to a protein complex comprising a herpesvirus gB polypeptide homotrimer complex, a herpesvirus gH glycoprotein, and a herpesvirus gL glycoprotein, where the herpesvirus gB polypeptide homotrimer complex comprises a trimer of three modified herpesvirus gB polypeptides. In certain embodiments, the herpesvirus gH and gL glycoproteins comprises a herpesvirus gH/gL fusion protein. In certain embodiments, the protein complex further comprises one or more of a herpesvirus UL128, UL130, or UL131 polypeptide.

Also provided are methods of making the protein complex, comprising incubating in vitro a first protein and at least a second protein to form the protein complex. In one embodiment, the method of making the protein complex comprises incubating in vitro a herpesvirus gB polypeptide homotrimer complex, a herpesvirus gH glycoprotein, and a herpesvirus gL glycoprotein, where the herpesvirus gB polypeptide homotrimer complex comprises a trimer of three modified herpesvirus gB polypeptides, and forming the protein complex. In certain embodiments, the herpesvirus gH and gL glycoproteins comprises a herpesvirus gH/gL fusion protein. In certain embodiments, the method further comprises incubating one or more of a herpesvirus UL128, UL130, or UL131 polypeptide. Thus, in certain embodiments, the method comprises incubating a homotrimeric complex of a modified herpesvirus gB protein, a herpesvirus gH/gL fusion protein, and optionally a herpesvirus UL128, a herpesvirus UL130, and a herpesvirus UL131 polypeptide.

Also provided are methods of inducing an immune response in a subject by administering to the subject a vaccine composition comprising the herpesvirus protein complex, where the herpesvirus protein complex induces an immune response in the subject. The herpesvirus protein complex comprises a herpesvirus gB polypeptide homotrimer complex, a herpesvirus gH glycoprotein, and a herpesvirus gL glycoprotein, where the herpesvirus gB polypeptide homotrimer complex comprises a trimer of three modified herpesvirus gB polypeptides. In certain embodiments, the herpesvirus gH and gL glycoproteins comprises a herpesvirus gH/gL fusion protein. In certain embodiments, the protein complex further comprises one or more of a herpesvirus UL28, UL130, or UL131 polypeptide. Thus, in certain embodiments, the protein complex comprises a homotrimeric complex of a modified herpesvirus gB protein, a herpesvirus gH/gL fusion protein and optionally a herpesvirus UL128, a herpesvirus UL130, and a herpesvirus UL131A polypeptide.

BRIEF DESCRIPTION OF THE DRAWINGS

The accompanying drawings, which are incorporated in and constitute a part of this specification, illustrate certain embodiments, and together with the written description, serve to explain certain principles of the constructs and methods disclosed herein.

FIG. 1A shows a Western blot analysis of HCMV gB under fully reduced conditions using an anti-His monoclonal antibody.

FIG. 1B shows a Western blot analysis of HCMV gB under partially reduced conditions using an anti-His monoclonal antibody.

FIG. 2A shows a Western blot under modified native conditions using an anti-HCMV gB monoclonal antibody.

FIG. 2B shows a Western blot under reduced conditions using an anti-HCMV gB monoclonal antibody.

FIG. 3 depicts a schematic difference between a wild type HCMV gB and a modified HCMV gB of the present disclosure.

FIG. 5 shows serum titers of HCMV gB-specific IgG in rabbits immunized with trimeric HCMV gB on days 0, 21, and 42.

FIGS. 6A-B show the in vitro neutralizing activity of serum from rabbits immunized with trimeric HCMV gB against live HCMV using MRC-5 fibroblasts (A) and ARPE-19 epithelial cells (B). Human serum from a CMV-immune patient was used as a positive control ("Human sera").

FIGS. 9A-B show a Western blot analysis of HCMV gH/gL heterodimer under reducing conditions using an anti-His monoclonal antibody (A) or an anti-HCMV gH antibody (B).

FIG. 10 shows a Western blot analysis of HCMV gB/gH/gL protein complex under non-reducing conditions.

DETAILED DESCRIPTION

Figure 4:
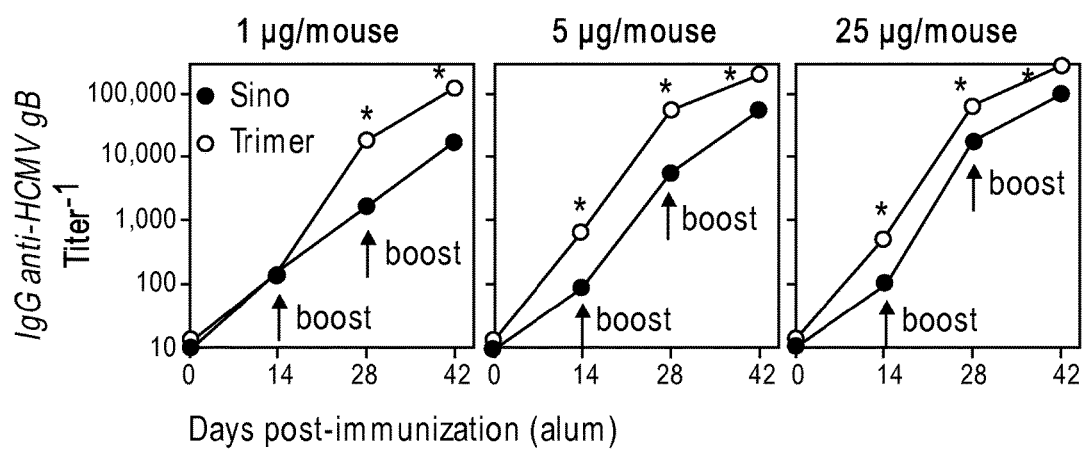
FIG. 4 shows that a modified HCMV gB of this disclosure ("Trimer") is markedly more immunogenic than non-trimeric control HCMV gB ("Sino"), which is nearly identical to what was used in the Phase II clinical trial by Pass et al., *Vaccine Prevention of Maternal Cytomegalovirus Infection*, N Engl J Med 2009; 360:1191-1199. Significance between modified HCMV gB and control protein, $p<0.05$ by Student-t test.
Figure 7A:
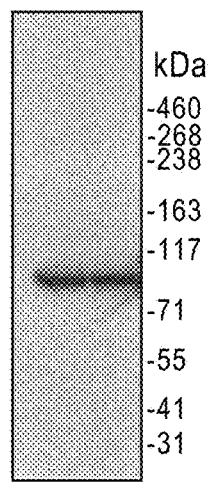
FIG. 7A shows a Western blot analysis of trimeric EBV gB under reducing conditions using an anti-His monoclonal antibody.
Figure 7B:
FIGS. 7B-C show a Western blot analysis of trimeric EBV gB under non-reducing conditions using an anti-His monoclonal antibody (B) or an anti-EBV gB antibody (C).
Figure 7C:
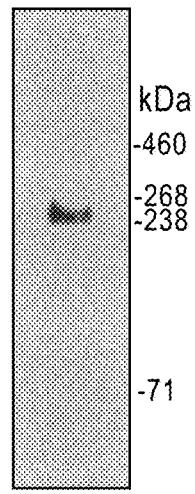

It is to be understood that the following detailed description is provided to give the reader a fuller understanding of certain embodiments, features, and details of aspects of the invention, and should not be interpreted as a limitation of the scope of the invention.

Definitions

In order that the present invention may be more readily understood, certain terms are first defined. Additional definitions are set forth throughout the detailed description.

The term "peptide linker" refers to a short, non-native peptide sequence that links two proteins or fragments of a protein.

The term "herpesvirus gH/gL fusion protein" refers to a recombinant fusion protein comprising a herpesvirus gH protein joined to a herpesvirus gL protein. The herpesvirus gH protein can be joined to the herpesvirus gL protein with a peptide linker.

The term "modified extracellular domain" refers to the extracellular domain of a human herpesvirus glycoprotein B that has been engineered such that the amino acid sequence is not the native amino acid sequence. As used herein, the extracellular domain of the human herpesvirus glycoprotein B has been modified by inserting a peptide linker at the furin cleavage site, effectively removing the furin recognition sequence. Examples of such human herpesviruses include, but are not limited to, CMV (Cytomegalovirus), HSV-1 (Herpes Simplex Virus-1), HSV-2 (Herpes Simplex Virus-2), VZV (Varicella-Zoster Virus), EBV (Epstein-Barr Virus), and HSHV (Kaposi Sarcoma-related Herpes Virus).

The terms "modified herpesvirus gB" and "modified herpesvirus gB polypeptide" are used interchangeably and refer to a human herpesvirus glycoprotein B polypeptide comprising a modified extracellular domain.

The terms "modified HCMV gB" and "modified HCMV gB polypeptide" are used interchangeably and refer to a human CMV glycoprotein B polypeptide comprising a modified extracellular domain.

The terms "modified EBV gB" and "modified EBV gB polypeptide" are used interchangeably and refer to a human Epstein Barr virus glycoprotein B polypeptide comprising a modified extracellular domain.

The term "leader sequence" refers to a short peptide sequence at the N-terminus of a recombinant protein that directs the recombinant protein to be secreted by the cell.

The terms "homotrimer," "homotrimer complex," and "homotrimeric complex" are used interchangeably and refer to the association of three polypeptides, such as three modified herpesvirus or HCMV gB polypeptides.

The term "pharmaceutically acceptable carrier" or "pharmaceutically acceptable excipient" means solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. In certain embodiments, the pharmaceutically acceptable carrier or excipient is not naturally occurring.

The term "isolated," when used in the context of a polypeptide or nucleic acid refers to a polypeptide or nucleic acid that is substantially free of its natural environment and is thus distinguishable from a polypeptide or nucleic acid that might happen to occur naturally. For instance, an isolated polypeptide or nucleic acid is substantially free of cellular material or other polypeptides or nucleic acids from the cell or tissue source from which it was derived. The term also refers to preparations where the isolated polypeptide or nucleic acid is sufficiently pure for pharmaceutical compositions; or at least 70-80% (w/w) pure; or at least 80-90% (w/w) pure; or at least 90-95.

The terms "polypeptide," "peptide," and "protein" are used interchangeably herein to refer to polymers of amino acids.

The term "recombinant" when used in the context of a nucleic acid means a nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid, which can be used to transform or transfect a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

A homotrimeric herpesvirus gB, in contrast to the previously tested non-trimeric gB by Pass et al., *Vaccine Prevention of Maternal Cytomegalovirus Infection*, N Engl J Med 2009; 360:1191-1199, is likely to elicit higher total gB-specific IgG responses and more diverse neutralizing antibodies against herpesvirus due to its multimeric form and the likely expression of unique conformational, neutralizing epitopes by homotrimeric herpesvirus gB. Thus, new and improved constructs for enhancing immune responses are needed, particularly herpesvirus gB constructs, including but not limited to HCMV gB constructs, that can be used to enhance immune responses in response to herpesvirus infection.

Modified Herpesvirus/HCMV gB.

The nucleic acid sequence encoding for wild type HCMV gB is set forth in SEQ ID NO: 1. The polypeptide sequence of wild type HCMV gB is set forth in SEQ ID NO: 2. Wild type HCMV gB is expressed as a 906 amino acid precursor protein. The first 22 amino acids comprise the native signal peptide, which sends the precursor protein to the endoplasmic reticulum (ER) for processing. The native signal peptide is cleaved off when the protein is folded in the ER. The polypeptide sequence of wild type HCMV gB consists of an extracellular domain (amino acids 23-750 of SEQ ID NO: 1), a transmembrane domain, and an intracellular domain (together, amino acids 751-906 of SEQ ID NO: 1).

Following transport from the ER, HCMV gB enters the Golgi apparatus where it undergoes glycosylation and is cleaved by the host enzyme, furin, in the extracellular domain at amino acids 460-461 of SEQ ID NO: 1. This proteolytic processing gives rise to two polypeptide fragments, gp116 and gp55. These two fragments remain covalently associated by disulfide bonds to form a gB subunit. It is believed that three HCMV gB subunits associate to create a homotrimer complex that mediates viral-host cell fusion (29-32).

The present disclosure relates to a new strategy for generating a modified herpesvirus gB polypeptide. The present disclosure describes a strategy for generating a modified HCMV gB polypeptide; however, it is understood that the strategy is not limited to HCMV and can be broadly applied across human herpesviruses, which share a homologous gB structure, including a furin cleavage site in the extracellular domain. Examples of such human herpesviruses include, but are not limited to, CMV, HSV-1 (Herpes Simplex Virus-1), HSV-2 (Herpes Simplex Virus-2), VZV (Varicella-Zoster Virus), EBV (Epstein-Barr Virus), and HSHV (Kaposi Sarcoma-related Herpes Virus). The nucleotide and amino acid sequences of the gB polypeptides of CMV, HSV-1, HSV-2, VZV, EBV, and HSHV are known.

The strategy involves creating nucleic acid constructs for inserting a peptide linker at the furin cleavage site in the extracellular domain of a herpesvirus (e.g., HCMV, HSV-1, HSV-2, VZV, EBV, and HSHV) gB such that the encoded herpesvirus (e.g., HCMV, HSV-1, HSV-2, VZV, EBV, and HSHV) gB forms a subunit that associates in triplicate to produce a gB trimeric complex. Surprisingly, modified HCMV gB polypeptide produced according to the present disclosure uniformly and consistently forms a homotrimeric complex. Without being limited by theory, it is believed that mutating the furin cleavage site in HCMV gB so that said site is rendered ineffectual, as had been done previously (see Spaete et al.), limits the movement of the HCMV gp116 and gp55 fragments, thereby interfering with the fragments' ability to form a homotrimeric complex. This could account for the inability of the previously described recombinant HCMV gB proteins to fold into a homotrimer. Replacing the furin cleavage site with a peptide linker, on the other hand, allows the gB polypeptide to form a trimeric complex, similar to the homotrimer that is believed to form naturally in a cell.

In certain embodiments, the modified herpesvirus (e.g., HCMV, HSV-1, HSV-2, VZV, EBV, and HSHV) gB polypeptide of the present disclosure comprises a modified extracellular domain of wild type herpesvirus (e.g., HCMV, HSV-1, HSV-2, VZV, EBV, and HSHV) gB and does not include the transmembrane domain or the intracellular domain of wild type herpesvirus (e.g., HCMV, HSV-1, HSV-2, VZV, EBV, and HSHV) gB. The modified herpesvirus (e.g., HCMV, HSV-1, HSV-2, VZV, EBV, and HSHV) gB generally retains one or more characteristics of the corresponding native herpesvirus (e.g., HCMV, HSV-1, HSV-2, VZV, EBV, and HSHV) gB, such as the ability to mediate viral-host cell fusion, or the ability to elicit antibodies (including, but not limited to, viral neutralizing antibodies) capable of recognizing native herpesvirus (e.g., HCMV, HSV-1, HSV-2, VZV, EBV, and HSHV) gB. Conventional methodology may be utilized to evaluate modified herpesvirus (e.g., HCMV, HSV-1, HSV-2, VZV, EBV, and HSHV) gB for one or more of the characteristics.

By way of example, and not limitation, the polynucleotide sequence can include nucleotides encoding for a leader sequence that is not the native herpesvirus (e.g., HCMV, HSV-1, HSV-2, VZV, EBV, and HSHV) gB leader sequence (e.g., the leader sequence is not amino acids 1-22 of SEQ ID NO: 1 for a modified HCMV gB polypeptide). In other embodiments, the polynucleotide sequence includes nucleotides encoding a protein comprising the amino acid sequence of SEQ ID NO: 4. In further embodiments, the polynucleotide sequence comprises SEQ ID NO: 3, which includes nucleotides encoding an IgG K leader sequence. In an embodiment, the IgG K leader sequence has the amino acid sequence METDTLLLWVLLLWVPGSTGD (SEQ ID NO: 6).

In an aspect, the modified HCMV gB was created with a nucleic acid construct encoding for the extracellular domain of wild type HCMV gB (amino acids 23-750 of SEQ ID NO: 1) but replacing the furin cleavage sequence (amino acids 457-461 of SEQ ID NO: 1) with a peptide linker, such as ((Gly$_4$Ser)$_3$ (SEQ ID NO: 5)). The nucleic acid sequence encoding for the modified HCMV gB is set forth in SEQ ID NO: 3. The polypeptide sequence of the modified HCMV gB is set forth in SEQ ID NO: 4. In one embodiment, the modified HCMV gB comprises only the extracellular domain which includes the gp116 and gp55 fragments joined together with the peptide linker. This modified HCMV gB construct uniformly forms a homotrimeric complex when expressed, as compared to the traditional non-trimeric HCMV gB protein produced by prior methods. This strategy for creating modified HCMV gB can be exploited with other peptide linkers in varying lengths and compositions as described below. This strategy for creating modified HCMV gB can result in a composition wherein the modified HCMV gB comprise at least 70%, for example at least 75%, 80%, 85%, or 90% homotrimers.

In another aspect, the modified HCMV gB can be created with the insertion of a peptide linker at the furin cleavage site between amino acid residues 460 and 461 without deleting any of the amino acid residues of the furin recognition sequence RTKRS (SEQ ID NO: 19). In yet another aspect, insertion of a peptide linker at the furin cleavage site can be coupled with deletion of 1, 2, 3, 4, or 5 amino acid residues of the furin recognition sequence RTKRS (SEQ ID NO: 19).

In a further aspect, the modified HCMV gB can comprise a partial sequence of the amino acid residues 23-460 of wild type HCMV gB at the amino terminal end of the peptide linker, and a partial sequence of the amino acid residues 461-750 of wild type HCMV gB at the carboxyl terminal end of the peptide linker.

This strategy for inserting a peptide linker at the cleavage site within a protein, with or without deleting part of or the entire enzyme recognition sequence, to achieve correct protein folding can be exploited with proteins other than herpesvirus glycoprotein B, including other viral, bacterial, parasitic, autoimmune, and tumor antigenic proteins. Thus, one aspect is directed to a recombinant polypeptide comprising a peptide linker that disrupts an enzymatic cleavage sequence, such as a furin cleavage sequence, that is present in the wild type form of the polypeptide. This platform can be used to create recombinant multimeric proteins that achieve correct native folding patterns without enzymatic cleavage when expressed in a host cell. For example, a homo- or heterodimer, homo- or heterotrimer, or tetramer can be created by inserting a peptide linker(s) at the cleavage site(s) responsible for multimeric formation. The encoded protein construct will form the appropriate naturally-occurring multimer without enzymatic cleavage by the host cell. In an aspect, a recombinant nucleic acid is contemplated that encodes the modified protein, and a method of using the recombinant nucleic acid to express the modified protein in a cell. In yet another aspect, it is contemplated methods of inducing an immune response in a subject by administering to the subject a vaccine composition comprising the modified protein or a nucleic acid encoding the same, where the modified protein induces an immune response in the subject.

Modified EBV gB

The nucleic acid sequence encoding for wild type EBV gB is set forth in SEQ ID NO: 7. The polypeptide sequence of wild type EBV gB is set forth in SEQ ID NO: 8. As with the HCMV gB, proteolytic processing of gB gives rise to two segments, which remain covalently associated by disulfide bonds to form a gB subunit.

In an aspect, the modified EBV gB comprises a nucleic acid construct encoding for the extracellular domain of wild type EBV gB (amino acids 23-732 of SEQ ID NO: 8) but replacing the furin cleavage sequence (amino acids 429-433 of SEQ ID NO: 8) with a peptide linker, such as ((Gly$_4$Ser)$_3$ (SEQ ID NO: 5)). The nucleic acid sequence encoding for the modified EBV gB is set forth in SEQ ID NO: 9. The polypeptide sequence of the modified EBV gB is set forth in SEQ ID NO: 10. In one embodiment, the modified EBV gB comprises only the extracellular domain which includes the two fragments joined together with the peptide linker. This modified EBV gB construct would uniformly form a homotrimeric complex when expressed. This strategy for creating modified EBV gB can be exploited with other peptide linkers in varying lengths and compositions as described below. This strategy for creating modified EBV gB can result in a composition wherein the modified EBV gB comprise at least 70%, for example at least 75%, 80%, 85%, or 90% homotrimers.

In another aspect, the modified EBV gB can be created with the insertion of a peptide linker at the furin cleavage site between amino acid residues 432 and 433 without deleting any of the amino acid residues of the furin recognition sequence RRRRD (SEQ ID NO: 20). In yet another aspect, insertion of a peptide linker at the furin cleavage site can be coupled with deletion of 1, 2, 3, 4, or 5 amino acid residues of the furin recognition sequence RRRRD (SEQ ID NO: 20).

In a further aspect, the modified EBV gB can comprise a partial sequence of the amino acid residues 23-432 of wild type EBV gB at the amino terminal end of the peptide linker, and a partial sequence of the amino acid residues 433-732 of wild type EBV gB at the carboxyl terminal end of the peptide linker.

Peptide Linker Sequences.

In the modified herpesvirus gB polypeptides (e.g., HCMV gB, HSV-1 gB, HSV-2 gB, VZV gB, EBV gB, or HSHV gB), linker sequences are inserted at the furin cleavage site. For example, the gp116 and gp55 fragments naturally formed when wild type HCMV gB is enzymatically cleaved by furin are joined by the peptide linker in the modified HCMV gB of the present invention. It is understood that the peptide linker is a non-native sequence that does not naturally exists in the native protein sequence.

In one embodiment, the linker sequence is a polypeptide having 5-70 amino acids, particularly a length of 6, 7, 8, 9, 10, 11, 12, 13, 14, 15, 16, 17, 18, 19, 20, 21, 22, 23, 24, 25, 30, 35, 40, 45, 50, 55, 60, 65, or 70 amino acids. In another embodiment, the linker sequence is a polypeptide having 10-25 amino acids. The linker sequence preferably comprises glycine and serine amino acids. In one embodiment, the linker sequence is 15 amino acids in length and has the amino acid sequence $(Gly_4Ser)_3$ (SEQ ID NO:5).

Other suitable peptide linkers are those described in U.S. Pat. Nos. 4,751,180, 4,935,233, and 5,073,627, each of which is hereby incorporated by reference in its entirety. A DNA sequence encoding a desired linker sequence may be inserted in place of, and in the same reading frame as, for example, DNA sequences encoding one or more amino acids of the native furin cleavage site (e.g., RTKRS (SEQ ID NO: 19) in HCMV or RRRRD (SEQ ID NO: 20) in EBV) using conventional techniques known in the art. For example, a chemically synthesized oligonucleotide encoding the linker may be ligated in the full polynucleotide sequence to be inserted at the sequences encoding the native furin cleavage site.

Protein Complexes.

The present disclosure also provides protein complexes comprising a herpesvirus gB polypeptide homotrimer complex, a herpesvirus gH glycoprotein, and a herpesvirus gL glycoprotein, where the herpesvirus gB polypeptide homotrimer complex comprises a trimer of three modified herpesvirus gB polypeptides. In certain embodiments, the herpesvirus gH and gL glycoproteins are part of a herpesvirus gH/gL fusion protein. In other embodiments, the protein complex further comprises one or more of a herpesvirus UL128, UL130, or UL131 polypeptide. Also provided are vaccine compositions comprising the protein complexes and a pharmaceutically acceptable carrier and/or an adjuvant.

Proteins in the protein complex are linked by non-covalent protein-protein interactions, including but not limited to hydrogen bonding and salt bridges. The protein complex has a quaternary structure, corresponding to the arrangement or shape resulting from the assembly and interaction of the individual proteins, and, therefore, is useful for inducing neutralizing antibodies against conformation epitopes on the gB/gH/gL protein complex. The protein complex, as used herein, does not refer to the native protein complex as it exists on the surface of a herpesvirus. Rather, the protein complex is formed by incubating the individual proteins in vitro, to create a reconstructed protein complex. There have been no reports demonstrating that these herpesvirus proteins, in their natural conformation, assemble into a native complex upon in vitro co-incubation.

The present disclosure describes a strategy for generating a herpesvirus gB/gH/gL protein complex as discussed above, which can be applied to any human herpesviruses including, but not limited to, CMV, HSV-1 (Herpes Simplex Virus-1), HSV-2 (Herpes Simplex Virus-2), VZV (Varicella-Zoster Virus), EBV (Epstein-Barr Virus), and HSHV (Kaposi Sarcoma-related Herpes Virus). The nucleotide and amino acid sequences of the gB, gH, and gL polypeptides of CMV, HSV-1, HSV-2, VZV, EBV, and HSHV are known.

Nucleic Acids, Cloning and Expression Systems.

The present disclosure further provides isolated nucleic acids encoding the disclosed modified herpesvirus (e.g., HCMV, HSV-1, HSV-2, VZV, EBV, or HSHV) gB polypeptides. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The present disclosure also provides constructs in the form of plasmids, vectors, phagemids, transcription or expression cassettes which comprise at least one nucleic acid encoding a modified herpesvirus (e.g., HCMV, HSV-1, HSV-2, VZV, EBV, or HSHV) gB. The disclosure further provides a host cell which comprises one or more constructs as above.

Also provided are methods of making the modified herpesvirus (e.g., HCMV, HSV-1, HSV-2, VZV, EBV, or HSHV) gB polypeptides encoded by these nucleic acids. The modified herpesvirus (e.g., HCMV, HSV-1, HSV-2, VZV, EBV, or HSHV) gB proteins may be produced using recombinant techniques. The production and expression of recombinant proteins is well known in the art and can be carried out using conventional procedures, such as those disclosed in Sambrook et al., *Molecular Cloning: A Laboratory Manual* (4th Ed. 2012), Cold Spring Harbor Press. For example, expression of the modified herpesvirus (e.g., HCMV, HSV-1, HSV-2, VZV, EBV, or HSHV) gB protein may be achieved by culturing under appropriate conditions recombinant host cells containing the nucleic acid encoding the herpesvirus (e.g., HCMV, HSV-1, HSV-2, VZV, EBV, or HSHV) gB protein. Following production by expression the modified herpesvirus (e.g., HCMV, HSV-1, HSV-2, VZV, EBV, or HSHV) gB protein may be isolated and/or purified using any suitable technique, then used as appropriate.

Systems for cloning and expression of a polypeptide in a variety of different host cells are well known in the art. Any protein expression system compatible with the constructs disclosed in this application may be used to produce the modified herpesvirus (e.g., HCMV, HSV-1, HSV-2, VZV, EBV, or HSHV) gB protein.

Suitable vectors can be chosen or constructed, so that they contain appropriate regulatory sequences, including promoter sequences, terminator sequences, polyadenylation sequences, enhancer sequences, marker genes and other sequences as appropriate.

A further aspect of the disclosure provides a host cell comprising a nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. These techniques are well known in the art. See e.g., Current Protocols in Molecular Biology, Ausubel et al. eds., John Wiley & Sons (2010). DNA introduction may be followed by a selection method (e.g., antibiotic resistance) to select cells that contain the vector.

Vaccine Compositions.

The modified herpesvirus (e.g., HCMV, HSV-1, HSV-2, VZV, EBV, or HSHV) gB polypeptides and nucleic acids encoding the same and herpesvirus (e.g., HCMV, HSV-1, HSV-2, VZV, EBV, or HSHV) gB/gH/gL protein complexes that are described in this application provide an improved platform for developing a vaccine that achieves enhanced immunogenicity in a subject. A homotrimeric complex of modified herpesvirus (e.g., HCMV, HSV-1, HSV-2, VZV, EBV, or HSHV) gB or a protein complex comprising the homotrimeric complex of modified herpesvirus gB, in contrast to previously disclosed non-trimeric gB, is likely to elicit higher total gB-specific IgG responses and more diverse neutralizing antibodies against HCMV due to its multimeric form and the likely expression of unique conformational, neutralizing epitopes by trimeric gB. Thus, one embodiment is directed to a composition comprising the nucleic acid encoding the modified herpesvirus (e.g., HCMV, HSV-1, HSV-2, VZV, EBV, or HSHV) gB protein and at least one pharmaceutically acceptable excipient. Another embodiment is directed to a composition comprising a homotrimeric complex of the modified herpesvirus (e.g., HCMV, HSV-1, HSV-2, VZV, EBV, or HSHV) gB protein, at least one pharmaceutically acceptable excipient, and optionally an adjuvant. Yet another embodiment is directed to a composition comprising a protein complex, wherein the protein complex comprises a homotrimeric complex of the modified herpesvirus (e.g., HCMV, HSV-1, HSV-2, VZV, EBV, or HSHV) gB protein, a herpesvirus gH/gL fusion protein, at least one pharmaceutically acceptable excipient, and optionally an adjuvant. These compositions are collectively referred to as "vaccine composition." In certain embodiments, the vaccine composition does not include an adjuvant.

The pharmaceutically acceptable excipient can be chosen from, for example, diluents such as starch, microcrystalline cellulose, dicalcium phosphate, lactose, sorbitol, mannitol, sucrose, methyl dextrins; binders such as povidone, hydroxypropyl methylcellulose, dihydroxy propylcellulose, and sodium carboxylmethylcellulose; and disintegrants such as crospovidone, sodium starch glycolate, croscarmellose sodium, and mixtures of any of the foregoing. The pharmaceutically acceptable excipient can further be chosen from lubricants such as magnesium stearate, calcium stearate, stearic acid, glyceryl behenate, hygrogenated vegetable oil, glycerine fumerate and glidants such as colloidal silicon dioxide, and mixtures thereof. In some embodiments, the pharmaceutically acceptable excipient is chosen from microcrystalline cellulose, starch, talc, povidone, crospovidone, magnesium stearate, colloidal silicon dioxide, sodium dodecyl sulfate, and mixtures of any of the foregoing. The excipients can be intragranular, intergranular, or mixtures thereof.

The vaccine composition can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form. After formulation, the vaccine composition can be incorporated into a sterile container which is then sealed and stored at a low temperature (e.g., 4° C.), or it can be freeze dried.

The vaccine composition can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine composition can optionally comprise agents that enhance the protective efficacy of the vaccine, such as adjuvants. Adjuvants include any compound or compounds that act to increase an immune response to the modified herpesvirus (e.g., HCMV, HSV-1, HSV-2, VZV, EBV, or HSHV) gB protein, homotrimeric complex comprising the same, or protein complex comprising the homotrimer complex, thereby reducing the quantity of herpesvirus (e.g., HCMV, HSV-1, HSV-2, VZV, EBV, or HSHV) gB (or nucleic acid encoding the same) necessary in the vaccine, and/or the frequency of administration necessary to generate a protective immune response. Adjuvants can include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), Mycobacterialphlei (*M. phlei*) cell wall extract (MCWE) (U.S. Pat. No. 4,744,984), *M. phlei* DNA (M-DNA), and *M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α), interleukin-2 (IL-2), and granulocyte macrophage-colony stimulating factor (GM-CSF), or combinations thereof.

The vaccine composition can optionally further comprise other antigens from herpesviruses to further enhance the protective efficacy of the vaccine. In an embodiment, the additional herpesvirus antigens are derived from the same virus species as the modified gB protein. For example, if the vaccine composition comprises a modified HCMV gB protein, then the additional antigens are also HCMV antigens. In another non-limiting example, if the vaccine composition comprises a modified EBV gB protein, then the additional antigens are also EBV antigens. Non-limiting examples of such herpesvirus antigens include glycoprotein H (gH), glycoprotein L (gL), glycoprotein 350 (gp350), UL128, UL130, UL131, or combinations thereof. The nucleic acid and amino acid sequences of these herpesvirus antigens are known.

Any of the non-limiting other antigens can be multimerized according to PCT/US2013/052270, which is incorporated herein by reference in its entirety. In an embodiment, the vaccine composition can include at least one, two, three, four, or up to five of the other antigens. In another embodiment, each of these antigens can be multimerized to create multimeric fusion proteins comprising multiple copies of a single antigen of interest (e.g., a homodimer, homotrimer, or tetramer using two, three, or four copies of the same antigen), or to create multimeric fusion proteins comprising two or more different antigens of interest (e.g., heterodimer, heterotrimer, tetramer, pentamer, hexamer, or octamer). Preferably, if the vaccine composition comprises a homotrimeric complex of HCMV gB, the vaccine composition also comprises a pentameric complex of HCMV gH/gL/UL128/UL130/UL131 or an HCMV gH/gL fusion protein with or without UL128/UL130/UL13. Also preferably, if the vaccine composition comprises a homotrimeric complex of EBV gB, the vaccine composition also comprises a tetramer of EBV gp350 and a monomer of an EBV gH/gL fusion protein.

In certain embodiments, the herpesvirus gH/gL fusion protein comprises a peptide linker sequence, as described herein, that joins the gH protein to the gL protein. In certain embodiments, the herpesvirus gH and gL proteins are from a herpesvirus selected from the group consisting of HCMV, HSV-1, HSV-2, VZV, EBV, and HSHV. The amino acid sequences of these herpesvirus gH and gL proteins are known. In one embodiment, the amino acid sequence of the HCMV gH/gL fusion protein comprises the sequence of SEQ ID NO: 25.

The vaccine composition can be prepared using techniques well known to those skilled in the art including, but not limited to, mixing, sonication and microfluidation. The adjuvant can comprise from about 10% to about 80% (v/v) of the vaccine composition, more preferably about 20% to about 50% (v/v), and more preferably about 20% to about 30% (v/v), or any integer within these ranges.

The vaccine composition can be administered to any animal, and preferably is a mammal such as a human, mouse, rat, hamster, guinea pig, rabbit, cat, dog, monkey, cow, horse, pig, and the like. Humans are most preferred.

Administration of the vaccine composition can be by infusion or injection (e.g., intravenously, intramuscularly, intracutaneously, subcutaneously, intrathecal, intraduodenally, intraperitoneally, and the like). The vaccine composition can also be administered intranasally, vaginally, rectally, orally, intratonsilar, or transdermally. Additionally, the vaccine composition can be administered by "needle-free" delivery systems.

The effective amount of the vaccine composition may be dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art. Preferably, a therapeutically effective dose of the vaccine composition described herein will provide the therapeutic preventive benefit without causing substantial toxicity to the subject.

The vaccine composition can be administered to a patient on any schedule appropriate to induce and/or sustain an immune response against herpesvirus (e.g., HCMV, HSV-1, HSV-2, VZV, EBV, or HSHV) gB or a herpesvirus protein complex comprising gB/gH/gL. For example, patients can be administered a vaccine composition as a primary immunization as described and exemplified herein, followed by administration of a secondary immunization, or booster, to bolster and/or maintain protective immunity.

The vaccine administration schedule, including primary immunization and booster administration, can continue as long as needed for the patient, for example, over the course of several years, to over the lifetime of the patient. The frequency of primary vaccine and booster administration and dose administered can be tailored and/or adjusted to meet the particular needs of individual patients, as determined by the administering physician according to any means suitable in the art.

The vaccine composition may be administered prophylactically (before exposure to the antigen or pathogen of interest) or therapeutically (after exposure to the antigen or pathogen of interest).

Methods of Inducing an Immune Response.

In another aspect, a composition comprising 1) a homotrimer complex of the modified herpesvirus (e.g., HCMV, HSV-1, HSV-2, VZV, EBV, or HSHV) gB protein (or nucleic acid encoding the modified herpesvirus (e.g., HCMV, HSV-1, HSV-2, VZV, EBV, or HSHV) gB protein) or 2) a protein complex where the protein complex comprises a homotrimeric complex of a modified herpesvirus (e.g., HCMV, HSV-1, HSV-2, VZV, EBV, or HSHV) gB protein and herpesvirus gH and gL proteins (e.g., a herpesvirus gH/gL fusion protein) can be used in a method of inducing an immune response. The immune response can be induced in a naïve subject who has not previously been exposed to HCMV or other herpesvirus. Alternatively, the immune response can be induced in a subject who has been previously exposed to a herpesvirus (e.g., HCMV, HSV-1, HSV-2, VZV, EBV, or HSHV) and used to enhance an existing immune response.

In one embodiment, the method of enhancing an immune response comprises administering to a subject a composition comprising 1) a homotrimer complex of a modified herpesvirus (e.g., HCMV, HSV-1, HSV-2, VZV, EBV, or HSHV) gB protein or 2) a protein complex where the protein complex comprises a homotrimeric complex of a modified herpesvirus (e.g., HCMV, HSV-1, HSV-2, VZV, EBV, or HSHV) gB protein and herpesvirus gH and gL proteins (e.g., a herpesvirus gH/gL fusion protein), wherein the homotrimer complex of the herpesvirus (e.g., HCMV, HSV-1, HSV-2, VZV, EBV, or HSHV) gB protein or the protein complex induces an immune response against HCMV or other herpesvirus. In another embodiment, the method of enhancing an immune response comprises administering to a subject a composition comprising a nucleic acid construct that encodes a modified herpesvirus (e.g., HCMV, HSV-1, HSV-2, VZV, EBV, or HSHV) gB protein, as described in this application, wherein the modified herpesvirus (e.g., HCMV, HSV-1, HSV-2, VZV, EBV, or HSHV) gB protein is expressed in the subject and a homotrimer complex thereof induces an immune response against the herpesvirus (e.g., HCMV, HSV-1, HSV-2, VZV, EBV, or HSHV) in the subject.

In these methods of inducing or suppressing an immune response, the immune response can be measured using routine methods in the art, such as those disclosed in this application. These routine methods include, but are not limited to, measuring an antibody response, such as an antibody response directed against a protein encoded by the recombinant vector, and measuring cellular proliferation, including, for example, by measuring tritiated thymidine incorporation or cytokine (e.g., IFN-γ) production.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Expression of Trimeric HCMV gB Protein

Construction of Plasmids for Production of Trimeric HCMV gB.

To test whether trimeric HCMV glycoprotein B can provide an effective and reproducible means for enhancing immune responses to HCMV infection, a recombinant nucleic acid plasmid (SEQ ID NO: 3) was designed to encode for amino acids 23-750 of SEQ ID NO: 1, with the coding sequence for the furin cleavage site (RTKRS (SEQ ID NO: 19) between amino acids 457-461 of SEQ ID NO: 1) being replaced with the coding sequence for a $(Gly_4Ser)_3$ (SEQ ID NO: 5) linker. Without intending to be bound by theory, it is believed that introduction of the $(Gly_4Ser)_3$ (SEQ ID NO: 5) linker allows for proper protein folding and thus formation of a homotrimeric HCMV glycoprotein B complex. The recombinant nucleic acid also included a nucleic acid encoding for an IgG K leader sequence on the 5' end to direct protein secretion into the cell supernatant, and a nucleic acid encoding for a $His_6$ (SEQ ID NO: 26) sequence on the 3' end to aid in purification and immunohistochemical analysis. The recombinant nucleic acid (SEQ ID NO: 3) was cloned into the pOptiVEC vector (Life Technologies, Carlsbad, Calif.), and verified by sequencing.

Transfection of Chinese Hamster Ovary (CHO) Cells (Strain DG44).

CHO DG44 cells were maintained in "CD DG44" medium (Life Technologies, Carlsbad, Calif.), and $2\times10^7$ cells were used for transfection. Thirty Ctg of the recombinant nucleic acid construct was re-suspended in 1.2 ml OptiPro™ ((Life Technologies, Carlsbad, Calif.) SFM medium after linearization with PvuI, followed by adding 30 μl of FreeStyle™ Max Reagent (Life Technologies, Carlsbad, Calif.) mixed gently and incubated for 10 min at room temperature. The DNA-FreeStyle™ Max Reagent (Life Technologies, Carlsbad, Calif.) complex was slowly added into the flask containing $2\times10^7$ DG44 cells with gentle shaking. The cells were incubated at 37'C, 5% $CO_2$ for 48 hours. Cells were centrifuged at 1,200 rpm and maintained in CD OptiCHO™ (Life Technologies, Carlsbad, Calif.) serum-free medium. Methotrexate (MTX, Sigma, St. Louis, Mo.) was used to select high recombinant protein-secreting cells, with the concentration of MTX gradually increased from 50 nM to 4 μM.

Immunohistochemical Analysis of Modified HCMV gB Proteins with Anti-His Antibody.

After MTX selection, modified HCMV gB expressing CHO cells were loaded into "Fibercell" cartridges (FiberCell Systems, Inc., Frederick, Md.), and concentrated supernatants were collected daily. Supernatants were further concentrated by centrifugation at 3,000 rpm for 30 min using a Centriprep® Centrifugal Filter Unit, 30,000 MW cut-off (Thermo Scientific Fisher, Waltham, Mass.). Affinity purification was performed using a cobalt column (Thermo Scientific Fisher, Waltham, Mass.), according to manufacturer's instructions. Briefly, concentrated supernatants were mixed with an equal volume of equilibration buffer, and added to the cobalt purification column. The column was incubated with gentle agitation for 60 min at 4° C. and washed 3× with washing buffer. The modified HCMV gB proteins were eluted with elution buffer and analyzed by electrophoresis on 3-8% NuPAGE® Tris-Acetate Mini Gels (Life Technologies, Carlsbad, Calif.), under fully reducing or partially reducing conditions, and blotted with anti-His monoclonal antibody (Life Technologies, Carlsbad, Calif.).

Under fully reduced conditions (with sodium dodecyl sulfate (SDS), β-mercaptoethanol, and boiling for ten minutes), analysis by Western blot using anti-His antibody revealed a 120 kDa band, as shown in FIG. 1A. This 120 kDa band is consistent with monomeric HCMV gB since fully reducing conditions disrupt any native oligomers into their monomeric form. These results demonstrate that in its non-native form, the modified HCMV gB of the present disclosure is a monomer.

Under partially reducing conditions (with sodium dodecyl sulfate (SDS), Pi-mercaptoethanol, and heating at 70° C. for ten minutes), which allows for detection of HCMV gB in its native form, analysis by Western blot using anti-His antibody revealed a uniform band of higher molecular weight, approximately 360 kDa, as shown in FIG. 1B. This band of about 360 kDa is consistent with the native, homotrimeric form of HCMV gB.

Immunohistochemical Analysis of Modified HCMV gB Proteins with Anti-gB Antibody.

The modified HCMV gB proteins were also analyzed by electrophoresis on 3-8% NuPAGE® Tris-Acetate Mini Gels (Life Technologies, Carlsbad, Calif.), under denaturing or modified native conditions, and blotted with anti-CMV gB antibodies (2F12, Virusys, Taneytown, Md.; or LS-C64457, LifeSpan BioSciences, Seattle, Wash.).

Under denaturing conditions, which disrupt any native oligomers into their monomeric form, modified HCMV gB was boiled for ten minutes in loading buffer containing 50 mM DTT. The proteins were then transferred to nitrocellulose membranes and blotted with anti-gB monoclonal antibodies (2F12, Virusys, Taneytown, Md.; or LS-C64457, LifeSpan BioSciences, Seattle, Wash.). As shown in FIG. 2B, the blots revealed a 120 kDa band corresponding with monomeric HCMV gB. These results demonstrate that the modified HCMV gB of the present disclosure in non-native form is a monomer.

Under modified native conditions, which allows for detection of HCMV glycoprotein B in its native form, modified HCMV gB was mixed with loading buffer containing LDS (lithium dodecyl sulfate) but no DTT and resolved in native running buffer. The proteins were then transferred to nitrocellulose membranes and blotted with anti-gB monoclonal antibody (LS-C64457, LifeSpan BioSciences, Seattle, Wash.). As shown in FIG. 2A, the blots revealed a uniform band of about 360 kDa, which is consistent with the native, homotrimeric form of HCMV gB.

Example 2

Immunization of Mice with Trimeric HCMC gB Protein

Purified Non-Trimeric Recombinant HCMV gB Protein.

A total of 2 mg of HCMV gB protein was purchased from Sino Biological, Inc. (Beijing, P.R. China). This HCMV gB protein was produced in the human embryonic kidney (HEK) 293 cell line using a DNA sequence encoding the extracellular domain (amino acids 1-700 of SEQ ID NO: 1) linked with the cytoplasmic domain (amino acids 777-907 of SEQ ID NO: 1), and fused with a polyhistidine tag at the C-terminal end to aid in protein purification. The furin cleavage site remained intact, but mutated so as to be ineffectual. This HCMV gB protein comprises 818 amino acids with a predicted molecular mass of 93 kDa under reducing conditions, but a molecular mass of 130-140 kDa due to glycosylation. The bioactivity of this protein was confirmed by its ability to bind biotinylated human CD209-Fc in a functional ELISA assay. Importantly, this HCMV gB protein is essentially identical to the non-trimeric HCMV gB protein used in clinical trials. (Pass et al., *N Engl J Med* 360: 1191-9).

Mice.

Female BALB/c mice were purchased from the National Cancer Institute (Frederick, Md.) and were used at 7-10 weeks of age for all protein immunizations. Female BALB/c mice were purchased from Harlan Laboratories (Indianapolis, Ind.) and were used at 4-6 weeks of age for all plasmid DNA vaccinations. These studies were conducted in accordance with the principles set forth in the Guide for Care and Use of Laboratory Animals (Institute of Laboratory Animal Resources, National Research Council, revised 1996), and were approved by the Uniformed Services University of the Health Sciences and the University of Washington Institutional Animal Care and Use Committees.

Immunization.

Female BALB/c mice were immunized i.p. with 3 different doses (25, 5.0, and 1.0 µg/mouse) of a homotrimeric complex of modified HCMV gB or commercial non-trimeric HCMV gB protein. The homotrimeric or non-trimeric HCMV gB was adsorbed on 13 µg of alum adjuvant (Allhydrogel 2%, Brenntag Biosector, Denmark), and administered with or without 25 µg of a stimulatory 30 mer CpG-containing oligodeoxynuclecotide (CpG-ODN). Serum samples for ELISA assays were obtained from blood taken from the tail vein on days 0, 14, 28, and 42 for measurement of serum titers of gB-specific IgG.

Measurement of Serum Titers in Mice of gB-Specific IgG and IgG Isotypes by ELISA.

Immulon 4 ELISA plates (Dynex Technologies, Inc., Chantilly, Va.) were coated (50 µL/well) with homotrimeric HCMV gB (5 µg/ml) in PBS overnight at 4° C. Plates were washed 3× with PBS+0.1% Tween 20 and were blocked with PBS+1% BSA for 1 h at 37° C. Threefold dilutions of serum samples from immunized mice, starting at a 1/50 serum dilution, in PBS+1% BSA were added, incubated overnight at 4° C., and plates were washed 3× with PBS+0.1% Tween 20. Alkaline phosphatase-conjugated polyclonal goat anti-mouse IgG, IgG3, IgG1, IgG2b, or IgG2a antibodies (SouthernBiotech, Birmingham, Ala.) (200 ng/ml final concentration) in PBS+1% BSA were then added, and plates were incubated at 37° C. for 1 h. Plates were then washed 5× with PBS+0.1% Tween 20. Substrate (p-nitrophenyl phosphate, disodium; Sigma) at 1 mg/ml in TM buffer (1 M Tris+0.3 mM $MgCl_2$, pH 9.8) was then added for color development. Color was read at an absorbance of 405 nm on a Multiskan Ascent® ELISA reader (Labsystems, Finland). The results are shown in FIG. 4, demonstrating that a modified HCMV gB of this disclosure ("Trimer") is markedly more immunogenic (significantly higher anti-HCMV gB IgG) than non-trimeric control HCMV gB ("Sino").

Measurement of Serum gB-Specific Neutralizing Antibody by Competitive ELISA.

The competitive ELISA was adapted from that which we previously described (Colino J, Duke L, Ajunaraja S, Chen Q, Liu L, Lucas A H, Snapper C M. 2012. Differential Idiotype Utilization for the In Vivo Type 14 Capsular Polysaccharide-Specific Ig Responses to Intact *Streptococcus pneumoniae* versus a Pneumococcal Conjugate Vaccine. J Immunol 189: 575-86). Briefly, inhibition mixtures will be prepared by mixing sera at varying dilutions with 10 µg/ml of HCMV gB protein with incubation for 24 h at 4° C., before being transferred to wells previously coated with 1 g/ml of neutralizing mouse IgG1 anti-HCMV gB mAb LS-C64457 (LifeSpan BioSciences, Inc, Seattle, Wash.), and blocked with PBS-BSA. Sera from naïve mice or mice immunized with a control protein, such as EBV gp350, will serve as negative controls (i.e. no inhibition). In the final detection step, plates will be incubated with alkaline phosphatase-conjugated non-neutralizing mouse IgG1 anti-gB mAb 2F12 (Virusys, Taneytown, Md.) for 1 h at 37° C. followed by addition of substrate (p-nitrophenyl phosphate, disodium) added at 1 mg/ml in TM buffer for color development. Color will be read at an absorbance of 405 nm on a Multiskan Ascent® ELISA reader (Labsystems, Finland) until the OD405 nm for the standard wells reach predetermined values. A standard curve will be generated using known concentrations of neutralizing mouse IgG1 anti-HCMV gB mAb LS-C64457 in the inhibition mixtures to convert the OD405 nm of each serum sample into a final ug/ml concentration of gB-specific neutralizing antibody, using a four-parameter logistic regression method with correction for the serum dilution.

CMV Neutralization Assay.

Neutralizing activities are determined by preparing 1:10 dilutions of each serum sample followed by additional 2-fold serial dilutions in culture medium. Each dilution is mixed with an equal volume of culture medium containing 4,000 pfu of HCMV (strain BADrUL131-Y4), incubated for 1 h at 37° C. then added to the wells of 384-well plates containing ARPE-19 (epithelial line, ATCC) or MRC-5 (fibroblast line, ATCC) monolayers. Each serum sample is assayed in triplicate and representative photomicrographs were taken using a Nikon Eclipse TS100 inverted UV microscope at four days post-infection. GFP fluorescence is measured seven days post-infection using a PerkinElmer Victor V1420 multilable counter. Fifty percent inhibitory concentration (IC50) values and standard errors of the means are calculated using Prism software by plotting the means of triplicate GFP values for each serum dilution against log 2 serum concentration, calculating the best fit four-parameter equation for the data, and interpolating the serum dilution at the mid-point of the curve as the IC50 neutralizing titer.

Statistics.

All studies will be repeated at least 1× for reproducibility. Serum titers will be expressed as geometric means+/− standard error of the mean, with significance determined by a two-tailed students t-test (p≤0.05 considered significant). We previously determined that 7 mice per group give adequate statistical power to these studies.

Example 3

Immunization of Rabbits with Trimeric HCMC gB Protein

HCMV trimeric glycoprotein B (gB) induces highly boosted gB-specific IgG responses in rabbits that prevents in vitro HCMV infection of fibroblasts and epithelial cells. A group of 4 male New Zealand white rabbits, 12 to 15 weeks old were immunized subcutaneously with 25 ug of trimeric HCMV gB adsorbed to aluminum hydroxide (alum; 0.25 ug alum/mg protein). Rabbits were immunized on Day 0, Day 21, and Day 42 and serum samples were taken before initial immunization, and 10 days following each immunization. Serum titers of HCMV gB-specific IgG were determined. Primary immunization with trimeric HCMV gB elicited detectable serum titers of HCMV gB-specific IgG that were boosted about 100-fold following secondary immunization (FIG. 5). A third immunization showed no further increases in serum titers.

In vitro neutralizing activity against live HCMV, using fibroblasts (MRC-5) and epithelial cells (ARPE-19) (FIG. 6), was also analyzed. Human serum from a CMV-immune patient was used as a control ("human sera"). Induction of serum neutralizing titers from rabbits immunized with trimeric HCMV gB were observed and were comparable to those measured in human HCMV-immune sera, when assayed on fibroblasts (MRC-5) (FIG. 6). Although serum neutralizing titers on epithelial cells (ARPE-19) were also observed in HCMV trimeric gB-immunized rabbits, they were significantly lower than that observed in the human HCMV-immune serum (FIG. 6), suggesting a possible role for additional HCMV proteins in mediating protection on epithelial cells.

Measurement of Serum Titers in Rabbits of gB-Specific IgG Isotypes by ELISA.

Immulon 4 ELISA plates (Dynex Technologies, Chantilly, Va.) were coated overnight with 5 g/ml of HCMV gB protein in PBS (50 µl/well) at 4° C. The plates were then blocked with PBS+1% bovine serum albumin (BSA) (100 µl/well) for 2 h at 37° C. Three-fold serial dilutions of serum samples, starting at a 1/50 serum dilution, in PBS plus 1% BSA (50 µl/well) were then added and incubated overnight at 4° C. followed by washing (3×) with PBS+0.1% Tween-20. Alkaline phosphatase-conjugated polyclonal goat anti-rabbit IgG Ab (Southern Biotechnology) (200 ng/ml, 50 µl/well) in PBS plus 1% BSA was then added and plates were incubated at 37° C. for 1 h. Plates were then washed with PBS+0.1% Tween-20 and substrate (p-nitrophenyl phosphate, disodium; Sigma-Aldrich) was added at 1 mg/ml in TM buffer (1 M Tris+0.3 mM MgCl2, pH 9.8) for color development. Color was read at an absorbance of 405 nm on a Multiskan Ascent ELISA reader (Labsystems, Finland).

CMV Neutralization Assay.

Neutralizing activities were determined by preparing 1:10 dilutions of each serum sample followed by additional 2-fold serial dilutions in culture medium. Each dilution was mixed with an equal volume of culture medium containing 4,000 pfu of HCMV (strain BADrUL131-Y4), incubated for 1 h at 37° C. then added to the wells of 384-well plates containing ARPE-19 (epithelial line, ATCC) or MRC-5 (fibroblast line, ATCC) monolayers. Each serum sample was assayed in triplicate and representative photomicrographs were taken using a Nikon Eclipse TS100 inverted UV microscope at four days post-infection. GFP fluorescence was measured seven days post-infection using a PerkinElmer Victor V1420 multilable counter. Fifty percent inhibitory concentration ($IC_{50}$) values and standard errors of the means were calculated using Prism software by plotting the means of triplicate GFP values for each serum dilution against $log_2$ serum concentration, calculating the best fit four-parameter equation for the data, and interpolating the serum dilution at the mid-point of the curve as the $IC_{50}$ neutralizing titer.

Example 4

Expression of Trimeric Human EBV gB Protein

Figure 8:
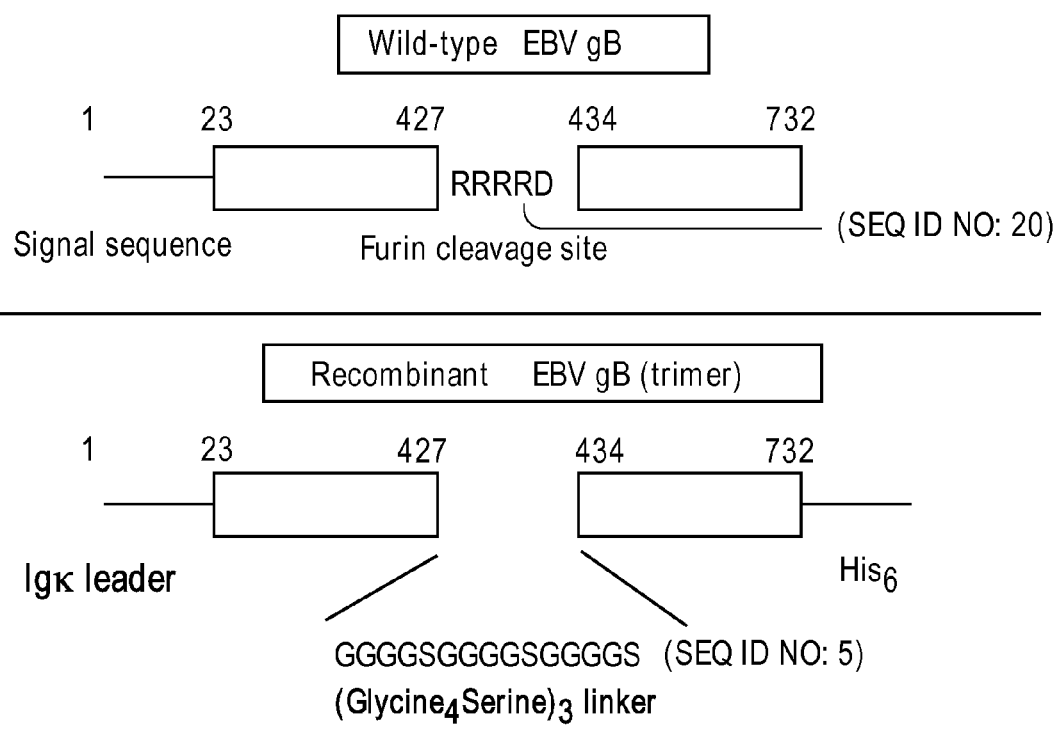
FIG. 8 depicts a schematic difference between a wild type EBV gB and a modified EBV gB of the present disclosure.

Construction of plasmids for production of trimeric EBV gB. To test whether homotrimeric EBV glycoprotein B can provide an effective and reproducible means for enhancing immune responses to EBV infection, a recombinant nucleic acid plasmid (SEQ ID NO: 9) was designed to encode for amino acids 23-732 of SEQ ID NO: 8, with the coding sequence for the furin cleavage site (RRRRD (SEQ ID NO: 20) between amino acids 429-433 of SEQ ID NO: 8 being replaced with the coding sequence for a (Gly$_4$Ser)$_3$ (SEQ ID NO:5) linker (FIG. 8). Without intending to be bound by theory, it is believed that introduction of the (Gly$_4$Ser)$_3$ linker allows for proper protein folding and thus formation of a trimeric EBV glycoprotein B complex. The EBV gB signal peptide (amino acids 1-22 of SEQ ID NO: 8) was replaced by an IgG K leader sequence (SEQ ID NO:6). Thus, the recombinant nucleic acid further included a nucleic acid encoding for an IgG K leader sequence on the 5' end to direct protein secretion into the cell supernatant, and a nucleic acid encoding for a $His_6$ (SEQ ID NO: 26) sequence on the 3' end to aid in purification and immunohistochemical analysis. The recombinant nucleic acid (SEQ ID NO: 9) was cloned into the pOptiVEC™ vector (Life Technologies, Carlsbad, Calif.), and verified by sequencing.

Transfection of Chinese Hamster Ovary (CHO) Cells (Strain DG44)

CHO DG44 cells were maintained in "CD DG44" medium (Life Technologies, Carlsbad, Calif.), and $2 \times 10^7$ cells were used for transfection. 30 µg of the recombinant nucleic acid construct were re-suspended in 1.2 ml OptiPro™ (Life Technologies, Carlsbad, Calif.) SFM medium after linearization with PvuI, followed by adding 30 µl of FreeStyle Max Reagent™ (Life Technologies, Carlsbad, Calif.) mixed gently and incubated for 10 min at room temperature. The DNA-Freestyle Max Reagent™ (Life Technologies, Carlsbad, Calif.) complex was slowly added into the flask containing $2 \times 10^7$ DG44 cells with gentle shaking. The cells were incubated at 37° C., 5% $CO_2$ for 48 hours. Cells were centrifuged at 1,200 rpm and maintained in CD OptiCHO™ (Life Technologies, Carlsbad, Calif.) serum-free medium. Methotrexate (MTX, Sigma, St. Louis, Mo.) was used to select high recombinant protein-secreting cells, with the concentration of MTX gradually increasing from 50 nM to 4 µM.

Immunohistochemical Analysis of Modified EBV gB Proteins with Anti-his Antibody.

After MTX selection, modified EBV gB expressing CHO cells were loaded into "Fibercell" cartridges (FiberCell Systems, Inc., Frederick, Md.), and concentrated supernatants were collected daily. Modified EBV gB expressing CHO cells were lysed with M-PER mammalian protein extraction reagent (Thermo Scientific Fisher, Waltham, Mass.), centrifuged at 3500 rpm for 60 min to remove cell debris. Supernatants were further concentrated by centrifugation at 3,000 rpm for 30 min using a Centriprep® Centrifugal Filter Unit (Thermo Scientific Fisher, Waltham, Mass.), 30,000 MW cut-off. Affinity purification was performed using a cobalt column (Thermo Scientific Fisher, Waltham, Mass.), according to manufacturer's instructions. Briefly, concentrated supernatants were mixed with an equal volume of equilibration buffer, and added to the cobalt purification column. The column was incubated with gentle agitation for 60 min at 4° C. and washed 3× with washing buffer.

Immunohistochemical Analysis of Modified EBV gB Proteins with Anti-EBV gB Antibody.

The modified EBV gB proteins were analyzed by electrophoresis on 3-8% NuPAGE® Tris-Acetate Mini Gels (Life Technologies, Carlsbad, Calif.), under denaturing or modified native conditions, and blotted with anti-His monoclonal antibody (Life Technologies, Carlsbad, Calif.) and anti-EBV gB antibodies (Virusys, Taneytown, Md.).

Under denaturing conditions, which disrupt any native oligomers into their monomeric form, modified ("trimeric") EBV gB was boiled for ten minutes in loading buffer containing 50 mM DTT. The proteins were then transferred to nitrocellulose membranes and blotted with anti-His monoclonal antibody ((Life Technologies, Carlsbad, Calif.) or anti-gB monoclonal antibodies (Virusys, Taneytown, Md.). As shown in FIG. 7A, the blots revealed an 80 kDa band corresponding with monomeric EBV gB. These results demonstrate that the modified EBV gB in non-native form is a monomer.

Under modified native conditions, which allows for detection of EBV gB in its native form, modified EBV gB was mixed with loading buffer containing LDS (lithium dodecyl sulfate) but no DTT and resolved in native running buffer. The proteins were then transferred to nitrocellulose membranes and blotted with anti-His monoclonal antibody (FIG. 7B) or anti-gB monoclonal antibody (FIG. 7C). As shown in FIGS. 7B/C, the blots revealed a uniform band of about 240 kDa, which is consistent with the native, trimeric form of EBV gB.

Example 5

Immunization Studies with Trimeric Human EBV gB Protein

Mice.

Female BALB/c mice will be purchased from the National Cancer Institute (Frederick, Md.) and will be used at 7-10 weeks of age for all protein immunizations. Female BALB/c mice will be purchased from Harlan Laboratories (Indianapolis, Ind.) and will be used at 4-6 weeks of age for all plasmid DNA vaccinations. These studies will be conducted in accordance with the principles set forth in the Guide for Care and Use of Laboratory Animals (Institute of Laboratory Animal Resources, National Research Council, revised 1996), and will be approved by the Uniformed Services University of the Health Sciences and the University of Washington Institutional Animal Care and Use Committees.

Immunizations.

Female BALB/c mice will be immunized i.p. with 3 different doses (25, 5.0, and 1.0 μg/mouse) of a homotrimeric complex of modified EBV gB or non-trimeric EBV gB protein. The homotrimeric or non-trimeric EBV gB will be adsorbed on 13 μg of alum adjuvant (Allhydrogel 2%, Brenntag Biosector, Denmark), and administered with or without 25 g of a stimulatory 30 mer CpG-containing oligodeoxynucleotide (CpG-ODN). Serum samples for ELISA assays will be obtained from blood taken from the tail vein on days 0, 14, 28, and 42 for measurement of serum titers of gB-specific IgG.

Measurement of Serum Titers of gB-Specific IgG and IgG Isotypes by ELISA.

Immulon 4 ELISA plates (Dynex Technologies, Inc., Chantilly, Va.) will be coated (50 μL/well) with homotrimeric EBV gB (5 μg/ml) in PBS overnight at 4° C. Plates will be washed 3× with PBS+0.1% Tween 20 and will be blocked with PBS+1% BSA for 1 h at 37'C. Threefold dilutions of serum samples from immunized mice, starting at a 1/50 serum dilution, in PBS+1% BSA will be added, incubated overnight at 4° C., and plates will be washed 3× with PBS+0.1% Tween 20. Alkaline phosphatase-conjugated polyclonal goat anti-mouse IgG, IgG3, IgG1, IgG2b, or IgG2a antibodies (SouthernBiotech, Birmingham, Ala.) (200 ng/ml final concentration) in PBS+1% BSA will then be added, and plates will be incubated at 37° C. for 1 h. Plates will then be washed 5× with PBS+0.1% Tween 20. Substrate (p-nitrophenyl phosphate, disodium; Sigma) at 1 mg/ml in TM buffer (1 M Tris+0.3 mM $MgCl_2$, pH 9.8) will then be added for color development. Color will be read at an absorbance of 405 nm on a Multiskan Ascent® ELISA reader (Labsystems, Finland).

EBV Neutralization Assay.

The method developed in Dr. Jeffery Cohen's Lab at NIH will be used (Sashihara J et al, Virology 2009, 391: 249-256). Briefly, serum samples will be serially diluted in 2-fold steps (from undiluted to 18 serial dilutions) and 25 µL of the diluted sample or control antibody will be added to wells of a 96 well plate in triplicate. 25 µl of B95-8/F EBV virus will then be added to each well and incubated for 2 hrs. 50 µl of $1\times10^5$ Raji cells will be added and incubated for 1 hour at 37° C., the cells will be washed twice by centrifuging the plates at 300×g for 5 min and replacing the media, and incubated for 3 days at 37° C. The plate will then be centrifuged, the cells be washed once with PBS, and be fixed in 2% paraformaldehyde in PBS.

GFP-expressing cells will be quantified using a FACSCalibur™ Flow Cytometer (BD Biosciences, San Jose, Calif., USA) and FlowJo software (Tree Star Inc., Ashland, Oreg.). The effective dilution of antibody that inhibited infectivity by 50% (EDI50) based on reduction of the number of GFP positive cells will be calculated by non-linear regression analysis using GraphPad PRISM® software (GraphPad Software, La Jolla, Calif.).

Statistics.

All studies will be repeated at least 1× for reproducibility. Serum titers will be expressed as geometric means+/– standard error of the mean, with significance determined by a two-tailed students t-test ($p \leq 0.05$ considered significant). We previously determined that 7 mice per group give adequate statistical power to these studies.

Example 6

Expression of HCMV gH/gL Fusion Protein

The HCMV gH/gL heterodimer is part of the herpesvirus family core fusion machinery that is necessary for HCMV fusion and penetration into fibroblasts cells, epithelial cells, endothelial cells, and dendritic cells. Vaccination of rabbits with recombinant gH/gL alone elicited neutralizing antibodies against fibroblasts and epithelial cells, although neutralization was somewhat higher against epithelial cells, when using the entire pentameric complex (gH/gL/UL128/130/131A) (66).

The coding sequences for HCMV gH and gL were downloaded from NCBI, reference sequence NC_006273.2, version GI:155573622, which sequence is hereby incorporated by reference in its entirety, including gH nucleotides 109224 through 111452 (SEQ ID NO: 21), gL nucleotides 165022 through 165858 (SEQ ID NO: 22). The construct for a herpesvirus gH/gL fusion protein was designed using MacVector. The amino acid sequences of wild type HCMV gH (SEQ ID NO: 18) and HCMV gL (SEQ ID NO: 24) are known. A nucleic acid encoding amino acids 31-278 of wild type HCMV gL was used (SEQ ID NO: 23), and the signal peptide 1-30 was replaced with an IgG K leader sequence (SEQ ID NO:6). A nucleic acid encoding amino acids 24-718 amino acids of wild type HCMV gH was used (SEQ ID NO: 17) and linked to the 3' end of gL, separated by a 15 amino acid linker $(Gly_4Ser)_3$ sequence (SEQ ID NO:5), and a His6 (SEQ ID NO: 26) coding sequence was linked to the 3' end of gH for protein purification. The amino acid sequence of the gH/gL construct corresponds to SEQ ID NO: 25. DNA coding for the gH/gL was synthesized by Blue Heron Biotechnology, Inc, cloned into pOptiVEC™ (Invitrogen), and verified by sequencing. Chinese Hamster Ovary cells (strain DG44) (Invitrogen) were transfected with pOptiVEC™-gH/gL constructs using Free-Style™ Max reagent (Invitrogen), and selected with gradually increased concentration of methotrexate up to 4 µM. Supernatants were concentrated and purified using Cobalt affinity purification (Thermo Scientific), and analyzed by Western blot using both an anti-His6 (SEQ ID NO: 26) antibody and anti HCMV gH/gL antibody (Santa Cruz Biotech). Under reducing conditions, the Western blot demonstrated monomeric gH/gL as a 110 KDa band with either a monoclonal anti-His antibody (FIG. 9A) or a monoclonal anti-gH antibody (FIG. 9B).

Example 7

Production of HCMV Protein Complex gB/gH/gL

HCMV entry into fibroblasts requires an HCMV envelope complex of trimeric gB, gH, and gL proteins, whereas the additional complexing of UL128/130/131A to gH/gL, in association with gB, is required for entry into endothelial, epithelial, and dendritic cells, and leukocytes (4, 5, 6).

Purified HCMV trimeric gB, as produced in Example 1, was mixed with purified monomeric gH/gL, as produced in Example 6, at a molecular ratio of 1:1, and incubated at room temperature for 2 hours. Subsequent analysis by Western blot under non-reducing conditions demonstrated a protein complex with a molecular weight of about 600 kDa (FIG. 10), consistent with a complex of one HCMV trimeric gB and two HCMV monomeric gH/gL heterodimers. There have been no reports demonstrating that these viral proteins, in their natural conformation, assemble into a native complex upon in vitro co-incubation. This may be due, in part, to the fact that it was previously not possible to produce a fully trimeric HCMV gB protein, which represents the HCMV gB in its natural conformation. This natural complex of HCMV proteins, which has not been previously expressed in vitro, represents a breakthrough in the design of prophylactic vaccines.

This protein complex vaccine also has implications beyond herpesvirus vaccines, as the same principle can be used to reconstitute protein complexes from the individual proteins of other viral or bacterial pathogens, which can, in turn, be used as vaccines to induce highly efficient neutralizing antibodies against conformational epitopes in the protein complex.

Example 8

Immunization Studies with HCMV Protein Complex gB/gH/gL

Mice.

Female BALB/c mice will be purchased from the National Cancer Institute (Frederick, Md.) and will be used at 7-10 weeks of age for all protein immunizations. Female BALB/c mice will be purchased from Harlan Laboratories (Indianapolis, Ind.) and will be used at 4-6 weeks of age for all plasmid DNA vaccinations. These studies will be conducted in accordance with the principles set forth in the Guide for Care and Use of Laboratory Animals (Institute of Laboratory Animal Resources, National Research Council, revised 1996), and will be approved by the Uniformed Services University of the Health Sciences and the University of Washington Institutional Animal Care and Use Committees.

Immunizations.

Female BALB/c mice will be immunized i.p. with 3 different doses (25, 5.0, and 1.0 g/mouse) of a HCMV gB/gH/gL protein complex as produced in Example 6. The HCMV gB/gH/gL protein complex will be adsorbed on 13 μg of alum adjuvant (Allhydrogel 2%, Brenntag Biosector, Denmark), and administered with or without 25 μg of a stimulatory 30 mer CpG-containing oligodeoxynucleotide (CpG-ODN). Serum samples for ELISA assays will be obtained from blood taken from the tail vein on days 0, 14, 28, and 42 for measurement of serum titers of gB, gH, and/or gL specific IgG.

Measurement of Serum Titers of gB/gH/gL-Specific IgG and IgG Isotypes by ELISA.

Immulon 4 ELISA plates (Dynex Technologies, Inc., Chantilly, Va.) will be coated (50 L/well) with HCMV gB/gH/gL protein complex (5 g/ml) in PBS overnight at 4° C. Plates will be washed 3× with PBS+0.1% Tween 20 and will be blocked with PBS+1% BSA for 1 h at 37° C. Threefold dilutions of serum samples from immunized mice, starting at a 1/50 serum dilution, in PBS+1% BSA will be added, incubated overnight at 4° C., and plates will be washed 3× with PBS+0.1% Tween 20. Alkaline phosphatase-conjugated polyclonal goat anti-mouse IgG, IgG3, IgG1, IgG2b, or IgG2a antibodies (SouthernBiotech, Birmingham, Ala.) (200 ng/ml final concentration) in PBS+1% BSA will then be added, and plates will be incubated at 37° C. for 1 h. Plates will then be washed 5× with PBS+0.1% Tween 20. Substrate (p-nitrophenyl phosphate, disodium; Sigma) at 1 mg/ml in TM buffer (1 M Tris+0.3 mM $MgCl_2$, pH 9.8) will then be added for color development. Color will be read at an absorbance of 405 nm on a Multiskan Ascent® ELISA reader (Labsystems, Finland).

CMV Neutralization Assay.

Neutralizing activities are determined by preparing 1:10 dilutions of each serum sample followed by additional 2-fold serial dilutions in culture medium. Each dilution is mixed with an equal volume of culture medium containing 4,000 pfu of HCMV (strain BADrUL131-Y4), incubated for 1 h at 37° C. then added to the wells of 384-well plates containing ARPE-19 (epithelial line, ATCC) or MRC-5 (fibroblast line, ATCC) monolayers. Each serum sample is assayed in triplicate and representative photomicrographs were taken using a Nikon Eclipse TS100 inverted UV microscope at four days post-infection. GFP fluorescence is measured seven days post-infection using a PerkinElmer Victor V1420 Multilable Counter. Fifty percent inhibitory concentration ($IC_{50}$) values and standard errors of the means are calculated using Prism software by plotting the means of triplicate GFP values for each serum dilution against $log_2$ serum concentration, calculating the best fit four-parameter equation for the data, and interpolating the serum dilution at the mid-point of the curve as the $IC_{50}$ neutralizing titer.

Statistics.

All studies will be repeated at least 1× for reproducibility. Serum titers will be expressed as geometric means+/− standard error of the mean, with significance determined by a two-tailed students t-test (p≤0.05 considered significant). We previously determined that 7 mice per group give adequate statistical power to these studies.

The following references are cited in the application and provide general information on the field of the invention and provide assays and other details discussed in the application. The following references are incorporated herein by reference in their entirety.

1. Spaete R R. 1991. A recombinant subunit vaccine approach to HCMV vaccine development. *Transplant Proc* 23: 90-6
2. Pass R F, Zhang C, Evans A, Simpson T, Andrews W, Huang M L, Corey L, Hill J, Davis E, Flanigan C, Cloud G. 2009. Vaccine prevention of maternal cytomegalovirus infection. *N Engl J Med* 360: 1191-9
3. Backovic M, Longnecker R, Jardetzky T S. 2009. Structure of a trimeric variant of the Epstein-Barr virus glycoprotein B. *Proc Natl Acad Sci USA* 106: 2880-5
4. Hahn G, Revello M G, Patrone M, Percivalle E, Campanini G, Sarasini A, Wagner M, Gallina A, Milanesi G, Koszinowski U, Baldanti F, Gerna G. 2004. Human cytomegalovirus UL131-128 genes are indispensable for virus growth in endothelial cells and virus transfer to leukocytes. *J Virol* 78: 10023-33
5 Akter P, Cunningham C, McSharry B P, Dolan A, Addison C, Dargan D J, Hassan-Walker A F, Emery V C, Griffiths P D, Wilkinson G W, Davison A J. 2003. Two novel spliced genes in human cytomegalovirus. *J Gen Virol* 84: 1117-22
6 Gerna G, Percivalle E, Lilleri D, Lozza L, Fornara C, Hahn G, Baldanti F, Revello M G. 2005. Dendritic-cell infection by human cytomegalovirus is restricted to strains carrying functional UL131-128 genes and mediates efficient viral antigen presentation to CD8+ T cells. *J Gen Virol* 86: 275-84

What is claimed:

1. A modified human herpesvirus glycoprotein B (gB) polypeptide, wherein the modified human herpesvirus gB polypeptide is a modified version of a human herpesvirus gB polypeptide that has a furin cleavage site in its extracellular domain, wherein the modified human herpesvirus gB polypeptide comprises a modified extracellular domain or fragment thereof, wherein the modified extracellular domain or fragment thereof comprises a peptide linker inserted into the furin cleavage site, wherein the peptide linker is 6 to about 70 amino acids in length, and wherein the modified human herpesvirus gB polypeptide is capable of forming a homotrimeric complex.

2. The modified human herpesvirus gB polypeptide of claim 1, wherein the human herpesvirus gB is selected from the group consisting of human cytomegalovirus (HCMV) gB, VZV (Varicella-Zoster Virus) gB, EBV (Epstein-Barr Virus) gB, and HSHV (Kaposi Sarcoma-related Herpes Virus) gB.

3. The modified human herpesvirus gB polypeptide of claim 2, wherein the human herpesvirus gB is HCMV gB or EBV gB.

4. The modified human herpesvirus gB polypeptide of claim 3, wherein the human herpesvirus gB is HCMV gB and wherein the modified extracellular domain comprises a peptide linker sequence inserted into the furin cleavage site of the wild type HCMV gB amino acid sequence SEQ ID NO: 2.

5. The modified human herpesvirus gB polypeptide of claim 1, wherein the human herpesvirus gB polypeptide does not include a transmembrane domain or an intracellular domain.

6. The modified human herpesvirus gB polypeptide of claim 1, wherein the peptide linker is 8 to about 70 amino acids in length.

7. The modified human herpesvirus gB polypeptide of claim 1, wherein the peptide linker is about 15 amino acids in length.

8. The modified human herpesvirus gB polypeptide of claim 1, wherein the peptide linker consists of the amino acid sequence GGGGSGGGGSGGGGS (SEQ ID NO: 5).

9. The modified human herpesvirus gB polypeptide of claim 1, further comprising a leader sequence at the N-terminus of the gB polypeptide, wherein the leader sequence is not the native gB polypeptide leader sequence.

10. The modified human herpesvirus gB polypeptide of claim 9, wherein the leader sequence has the amino acid sequence METDTLLLWVLLLWVPGSTGD (SEQ ID NO: 6).

11. The modified human herpesvirus gB polypeptide of claim 1, wherein the amino acid sequence of the human herpesvirus gB polypeptide comprises SEQ ID NO: 4.

12. A herpesvirus gB polypeptide homotrimer complex, wherein the homotrimer complex comprises three modified human herpesvirus gB polypeptides of claim 1.

13. The herpesvirus gB polypeptide homotrimer complex of claim 12, wherein the herpesvirus is HCMV and the homotrimer complex has a molecular weight (MW) of about 360 kDa.

14. A vaccine composition comprising the herpesvirus gB polypeptide homotrimer complex of claim 12 and a pharmaceutically acceptable excipient and/or an adjuvant.

15. The vaccine composition of claim 14, further comprising at least one human herpesvirus antigen.

16. The vaccine composition of claim 15, wherein the at least one human herpesvirus antigen is selected from the group consisting of glycoprotein H (gH), glycoprotein L (gL), glycoprotein 350 (gp350), UL128, UL130, UL131, and combinations thereof.

17. The vaccine composition of claim 16, wherein the at least one human herpesvirus antigen is a multimer.

18. The vaccine composition of claim 14, wherein at least 70% of the human herpesvirus gB polypeptides are homotrimers.

19. A protein complex comprising a herpesvirus gB polypeptide homotrimer complex, a herpesvirus glycoprotein H (gH), and a glycoprotein L (gL), wherein the homotrimer complex comprises three modified human herpesvirus gB polypeptides and each modified human herpesvirus gB polypeptide is a modified version of a human herpesvirus gB polypeptide that has a furin cleavage site in its extracellular domain, wherein the modified human herpesvirus gB polypeptide comprises a modified extracellular domain or fragment thereof, wherein the modified extracellular domain or fragment thereof comprises a peptide linker inserted into the furin cleavage site, wherein the peptide linker is from 6 to about 70 amino acids in length.

20. The protein complex of claim 19, wherein the herpesvirus gH and the herpesvirus gL form a herpesvirus gH/gL fusion protein.

21. The protein complex of claim 19, wherein the human herpesvirus gB is selected from the group consisting of human cytomegalovirus (HCMV) gB, HSV-1 (Herpes Simplex Virus-1) gB, HSV-2 (Herpes Simplex Virus-2) gB, VZV (Varicella-Zoster Virus) gB, EBV (Epstein-Barr Virus) gB, and HSHV (Kaposi Sarcoma-related Herpes Virus) gB.

22. The protein complex of claim 19, wherein the human herpesvirus gB is HCMV gB or EBV gB.

23. The protein complex of claim 19, wherein the human herpesvirus gB is HCMV gB and wherein the modified extracellular domain comprises a peptide linker sequence inserted into the furin cleavage site of the wild type HCMV amino acid sequence of SEQ ID NO: 2.

24. The protein complex of claim 19, wherein the human herpesvirus gB polypeptide does not include a transmembrane domain or an intracellular domain.

25. The protein complex of claim 19, wherein the peptide linker is from about 8 to about 70 amino acids in length.

26. The protein complex of claim 19, wherein the peptide linker is about 15 amino acids in length.

27. The protein complex of claim 19, wherein the peptide linker consists of the amino acid sequence GGGGSGGGGSGGGGS (SEQ ID NO: 5).

28. The protein complex of claim 19, wherein the human herpesvirus gB polypeptide further comprises a leader sequence at the N-terminus of the gB polypeptide, wherein the leader sequence is not the native gB polypeptide leader sequence.

29. The protein complex of claim 28, wherein the leader sequence has the amino acid sequence METDTLLLWV-LLLWVPGSTGD (SEQ ID NO: 6).

30. The protein complex of claim 20, wherein the herpesvirus gH/gL fusion protein comprises the amino acid sequence of SEQ ID NO:25.

31. The protein complex of claim 19, wherein the protein complex further comprises a herpesvirus UL128, UL130, and UL131 polypeptide.

32. A vaccine composition comprising the protein complex of claim 19 and a pharmaceutically acceptable excipient and/or an adjuvant.

33. A nucleic acid that encodes the modified human herpesvirus gB polypeptide of claim 1.

34. A recombinant vector comprising the nucleic acid of claim 33.

35. A method for inhibiting or treating a human herpesvirus infection in a patient comprising administering to the patient a therapeutically effective amount of a vaccine composition of claim 14, wherein the human herpesvirus infection comprises the same species of human herpesvirus used to prepare the vaccine composition.

36. A method for inducing immunity to a human herpesvirus infection in a subject comprising administering to the subject a vaccine composition of claim 14, wherein the human herpesvirus infection comprises the same species of human herpesvirus used to prepare the vaccine composition.

37. A method for inhibiting or treating a human herpesvirus infection in a patient comprising administering to the patient a protein complex of claim 19, wherein the human herpesvirus infection comprises the same species of human herpesvirus used to prepare the vaccine composition.

38. A method for inducing immunity to a human herpesvirus infection in a subject comprising administering to the subject a protein complex of claim 19, wherein the human herpesvirus infection comprises the same species of human herpesvirus used to prepare the protein complex.

39. The modified human herpesvirus gB polypeptide of claim 1, wherein the peptide linker is 10-25 amino acids in length.

40. The protein complex of claim 19, wherein the peptide linker is 10-25 amino acids in length.

41. The modified human herpesvirus gB polypeptide of claim 3, wherein the human herpesvirus gB is EBV gB and wherein the modified extracellular domain comprises a peptide linker sequence inserted into the furin cleavage site of the wild type EBV gB amino acid sequence.

42. The modified human herpesvirus gB polypeptide of claim 3, wherein the human herpesvirus gB is HCMV gB and wherein the modified extracellular domain comprises a peptide linker sequence inserted into the furin cleavage site of the wild type HCMV gB amino acid sequence.

43. The modified human herpesvirus gB polypeptide of claim 1, wherein the modified extracellular domain comprises a peptide linker sequence inserted into the furin cleavage site of a wild type gB polypeptide and wherein a part or all of the furin cleavage site of the wild type gB polypeptide is not deleted.

* * * * *